(12) United States Patent
Ma et al.

(10) Patent No.: US 12,145,924 B2
(45) Date of Patent: Nov. 19, 2024

(54) LYSOPHOSPHATIDIC ACID RECEPTOR 1 (LPAR1) INHIBITOR COMPOUNDS

(71) Applicant: Eli Lilly and Company, Indianapolis, IN (US)

(72) Inventors: Tianwei Ma, Carmel, IN (US); Liang Wu, Shanghai (CN); Xuejun Zhang, Shanghai (CN)

(73) Assignee: ELI LILLY AND COMPANY, Indianapolis, IN (US)

( * ) Notice: Subject to any disclaimer, the term of this patent is extended or adjusted under 35 U.S.C. 154(b) by 105 days.

(21) Appl. No.: 17/747,261

(22) Filed: May 18, 2022

(65) Prior Publication Data

US 2022/0281845 A1  Sep. 8, 2022

Related U.S. Application Data

(62) Division of application No. 16/633,371, filed as application No. PCT/US2018/048249 on Aug. 28, 2018, now Pat. No. 11,365,185.

(30) Foreign Application Priority Data

Sep. 4, 2017 (WO) ................ PCT/CN2017/100354

(51) Int. Cl.
| | |
|---|---|
| *A61P 1/16* | (2006.01) |
| *C07D 401/14* | (2006.01) |
| *C07D 403/12* | (2006.01) |
| *C07D 403/14* | (2006.01) |

(52) U.S. Cl.
CPC ............. *C07D 401/14* (2013.01); *A61P 1/16* (2018.01); *C07D 403/12* (2013.01); *C07D 403/14* (2013.01)

(58) Field of Classification Search
CPC ...................................................... A61P 1/16
See application file for complete search history.

(56) References Cited

U.S. PATENT DOCUMENTS

| | | |
|---|---|---|
| 9,272,990 B2 | 3/2016 | Seiders et al. |
| 2013/0253004 A1 | 9/2013 | Seiders et al. |
| 2018/0360803 A1 | 12/2018 | Nishikawa et al. |

FOREIGN PATENT DOCUMENTS

| | | |
|---|---|---|
| WO | 2010/077882 A2 | 7/2010 |
| WO | 2012/138648 A1 | 10/2012 |
| WO | 2012/138797 A1 | 10/2012 |

*Primary Examiner* — Brian E McDowell
(74) *Attorney, Agent, or Firm* — Thomas P. Weber

(57) ABSTRACT

The present invention provides a compound of formula

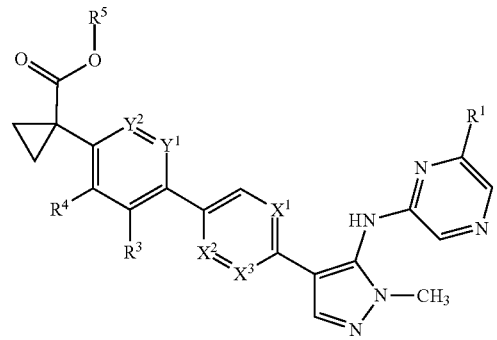

or a pharmaceutical salt thereof, use, methods for its preparation are described.

10 Claims, No Drawings

LYSOPHOSPHATIDIC ACID RECEPTOR 1 (LPAR1) INHIBITOR COMPOUNDS

This invention provides lysophosphatidic acid receptor 1 (LPAR1) inhibitor compounds and pharmaceutically acceptable salts thereof, and their use in therapy.

LPAR1 is the first high-affinty receptor identified for lysophosphatidic acids (LPA), which are small bioactive glycerophospholipids. LPA-mediated LPAR1 activation implicates numerous cellular responses including cell proliferation, migration, and survival.

Particularly, the LPA-LPAR1 pathway may contribute to the development of non-alcoholic steatohepatitis (NASH), which is a liver disease characterized by fat deposits, inflammation and tissue damage. NASH progression leads to the accumulation of scarring, or fibrosis, in the liver. If further advanced, NASH can cause cirrhosis and portal hypertension. About 2-5 percent of adult Americans and up to 20 percent of those who are obese may suffer from NASH. Beyond fibrosis and cirrhosis, NASH may progress to hepatocellular carcinoma and liver failure.

It has been suggested that inhibition of LPAR1 may be useful in treating inflammation, fibrosis, and other LPAR1-mediated diseases or disorders. For example, U.S. Pat. No. 9,272,990 discloses LPAR antagonists for treating fibrosis.

PCT Publication No. WO 2017/086430 discloses an a halogen-substituted thiophene compound as LPAR1 antagonist for the treatment and/or prophylaxis of NASH.

There is an unmet need for LPAR1 antagonist compounds that may be useful for treating NASH as well as other LPAR1-mediated diseases or disorders. Thus, the present invention provides compounds which display potent and selective LPAR1 antagonist activities in vitro, as well as efficacy in an animal model of liver inflammation and fibrosis. Further, the present invention provides ester prodrug of such LPAR1 antagonist compounds. Particularly, the present invention provides a compound of Formula I

I wherein,
$X^1$ and $X^2$ are each independently CH or N, and $X^3$ is C—$R^2$ or N, provided that when $X^1$ is CH, then $X^2$ is CH and $X^3$ is C—$R^2$, and provided that when $X^1$ is N, then no more than one of $X^2$ and $X^3$ may be N;
$Y^1$ and $Y^2$ are CH or N, provided that only one of $Y^1$ or $Y^2$ may be N;
$R^1$ is
  isopropyl,
  isobutyl,
  t-butyl,
  2-hydroxyprop-2-yl,
  cyclopropyl,
  cyclopropyloxy,
  t-butyloxy,
  cyclobutyloxy,
  3,3-difluorocyclobutyloxy,
  2-fluoroprop-2-yl,
  1,1-difluoroethyl,
  trifluoromethyl,
  isopropyloxy, or
  2-methoxyprop-2-yl;
$R^2$ is H or fluoro;
$R^3$ is H, halogen, $C_1$-$C_3$ alkyl, $C_1$-$C_3$ alkoxy, $C_1$-$C_3$ alkoxymethyl, $CF_3$, cyanomethyl or cyano;
$R^4$ is H, halogen, $C_1$-$C_3$ alkyl, $CF_3$ or cyano;
$R^5$ is H, methyl, ethyl, propyl, isopropyl, or cyclopropyl;
or a pharmaceutically acceptable salt thereof.

In one embodiment, $X^1$ is N.
In one embodiment, $X^1$ is CH.
In one embodiment, $Y^1$ is CH.
In one embodiment, $R^1$ is isopropyl.
In one embodiment, $R^1$ is cyclopropyloxy.
In one embodiment, $R^3$ is H, methyl, methoxymethyl, cyanomethyl or cyano.
In one embodiment, $R^4$ is H, methyl, $CF_3$, or cyano.
In one embodiment, $R^5$ is H.
In another embodiment, a compound of the present invention is any one of the compounds of the examples, or a pharmaceutically acceptable salt thereof.

In another aspect of the present invention there is provided a pharmaceutical composition, comprising a compound of Formula I, or a pharmaceutically acceptable salt thereof, and at least one pharmaceutically acceptable carrier, diluent, or excipient. This aspect of the invention also provides a pharmaceutical composition for treating NASH in a mammal, particularly a human, comprising a compound of Formula I, or a pharmaceutically acceptable salt thereof, and one or more pharmaceutically acceptable excipients, carriers, or diluents. Furthermore, this aspect of the present invention provides a pharmaceutical composition for treating fibrosis in a mammal, particularly a human, as for example pulmonary fibrosis, liver fibrosis, kidney fibrosis, heart fibrosis or skin fibrosis, comprising a compound of Formula I, or a pharmaceutically acceptable salt thereof, and one or more pharmaceutically acceptable excipients, carriers, or diluents. Furthermore, this aspect of the present invention provides a pharmaceutical composition for treating inflammatory diseases in a mammal, particularly a human, as for example chronic respiratory disease, chronic obstructive pulmonary disease (COPD), multiple sclerosis, rheumatoid arthritis, osteoarthritis, psoriasis, systemic lupus erythematosus, scleroderma, Sjorgen's syndrome, ulcerative colitis and Crohn's disease, comprising a compound of Formula I, or a pharmaceutically acceptable salt thereof, and one or more pharmaceutically acceptable excipients, carriers, or diluents.

In another aspect of the present invention there is provided a method of treating NASH in a mammal, particularly a human, comprising administering to a mammal in need of such treatment an effective amount of a compound of Formula I, or a pharmaceutically acceptable salt thereof.

In one embodiment of this aspect of the present invention provides a method of treating fibrosis in a mammal, particularly a human, as for example pulmonary fibrosis, liver fibrosis, kidney fibrosis, heart fibrosis or skin fibrosis, comprising administering to a mammal in need of such treatment an effective amount of a compound of Formula I, or a pharmaceutically acceptable salt thereof.

In another embodiment of this aspect of the present invention provides a method of treating inflammatory diseases in a mammal, particularly a human, as for example chronic respiratory disease, chronic obstructive pulmonary disease (COPD), multiple sclerosis, rheumatoid arthritis, osteoarthritis, psoriasis, systemic lupus erythematosus, scleroderma, Sjorgen's syndrome, ulcerative colitis and Crohn's disease, comprising administering to a mammal in need of such treatment an effective amount of a compound of Formula I, or a pharmaceutically acceptable salt thereof.

In another aspect of the present invention there is provided a compound of Formula I, or a pharmaceutically acceptable salt thereof for use in therapy. Within this aspect, the invention provides a compound of Formula I, or a pharmaceutically acceptable salt thereof, for use in the treatment of NASH in a mammal, particularly a human. The present invention also provides a compound of Formula I, or a pharmaceutically acceptable salt thereof, for use in the treatment of fibrosis in a mammal, particularly a human, as for example pulmonary fibrosis, liver fibrosis, kidney fibrosis, heart fibrosis or skin fibrosis. The present invention also provides a compound of Formula I, or a pharmaceutically acceptable salt thereof, for use in the treatment of inflammatory diseases in a mammal, particularly a human. In an embodiment of this aspect of the invention said inflammatory disease is selected from the group consisting of, but not limited to, chronic respiratory disease, chronic obstructive pulmonary disease (COPD), multiple sclerosis, rheumatoid arthritis, osteoarthritis, psoriasis, systemic lupus erythematosus, scleroderma, Sjorgen's syndrome, ulcerative colitis and Crohn's disease Another aspect of the present invention provides the use of a compound of Formula I, or a pharmaceutically acceptable salt thereof, in the manufacture of a medicament for the treatment of NASH in a mammal.

Another aspect of the present invention provides the use of a compound of Formula I, or a pharmaceutically acceptable salt thereof, in the manufacture of a medicament for the treatment of fibrosis in a mammal.

A further aspect of the present invention provides the use of a compound of Formula I, or a pharmaceutically acceptable salt thereof, in the manufacture of a medicament for the treatment of inflammatory diseases in a mammal. In an embodiment of this aspect of the invention said inflammatory disease is selected from the group consisting of, but not limited to, chronic respiratory disease, chronic obstructive pulmonary disease (COPD), multiple sclerosis, rheumatoid arthritis, osteoarthritis, psoriasis, systemic lupus erythematosus, scleroderma, Sjorgen's syndrome, ulcerative colitis and Crohn's disease.

As used herein, the term "effective amount" or "therapeutically effective amount" of a compound refers to an amount, or a dosage, which is effective in treating a disorder or a disease, such as NASH, fibrosis, inflammatory diseases, other LPAR1-mediated diseases or disorders as described herein. The attending diagnostician, as one skilled in the art, can readily determine an effective amount by the use of conventional techniques and by observing results obtained under analogous circumstances. In determining the effective amount or dose of a compound, a number of factors are considered, including but not limited to, the compound to be administered; the co-administration of other agents, if used; the species of mammal; its size, age, and general health; the degree of involvement or the severity of the disorder; the response of the individual patient; the mode of administration; the bioavailability characteristics of the preparation administered; the dose regimen selected; the use of other concomitant medication; and other relevant circumstances.

The terms "treatment" and "treating" as used herein are intended to refer to all processes wherein there may be a slowing, interrupting, arresting, controlling, or stopping of the progression of an existing disorder and/or symptoms thereof, but does not necessarily indicate a total elimination of all symptoms.

The term "pharmaceutically acceptable carrier, diluent, or excipients" means that the carrier, diluent, and excipients are pharmaceutically compatible with the other ingredients of the composition. In a particular embodiment, the pharmaceutical compositions are formulated as a tablet or capsule for oral administration. The tablet or capsule can include a compound of the present invention in an amount effective to treat fibrosis, inflammatory diseases, NASH, other LPAR1-mediated diseases or disorders.

As used herein, the term "fibrosis" refers to the formation or presence of excessive connective tissue in an organ or tissue. Fibrosis may occur as a repair or replacement response to a stimulus such as tissue injury or inflammation. A hallmark of fibrosis is the production of excessive extracellular matrix. The normal physiological response to injury results in the deposition of connective tissue as part of the healing process, but this connective tissue deposition may persist and become pathological, altering the architecture and function of the tissue. In exemplary embodiments, the fibrosis is pulmonary fibrosis, liver fibrosis, kidney fibrosis, heart fibrosis, or skin fibrosis.

While it is possible to administer compounds employed in the methods of this invention directly without any formulation, the compounds are usually administered in the form of pharmaceutical compositions comprising the compound of Formula I, or a pharmaceutically acceptable salt thereof, as an active ingredient and at least one pharmaceutically acceptable carrier, diluent and/or excipient. These compositions can be administered by a variety of routes including oral, sublingual, nasal, subcutaneous, intravenous, and intramuscular. Such pharmaceutical compositions and processes for preparing them are well known in the art. See, e.g., Remington: The Science and Practice of Pharmacy (University of the Sciences in Philadelphia, ed., 21$^{st}$ ed., Lippincott Williams & Wilkins Co., 2005).

Compounds of Formula I are generally effective over a wide dosage range. For example, dosages per day normally fall within the range of about 0.2 mg/kg to about 15 mg/kg, more usually from about 0.7 mg/kg to about 7.5 mg/kg, and as for example about 1.5 mg/kg of body weight. In some instances dosage levels below the lower limit of the aforesaid range may be more than adequate, while in other cases still larger doses may be employed without causing any harmful side effect, and therefore the above dosage ranges are not intended to limit the scope of the invention in any way. It may also be advantageous to administer the daily dose in parts over the course of each day (e.g. ½ dose twice a day or ⅓ dose three times a day). It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

The compositions are preferably formulated in a unit dosage form, each dosage containing from about 20 to about 2000 mg, more usually about 50 to about 500 mg, as for example about 200 mg of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient.

Compounds of this invention have basic and acidic moieties, and accordingly react with a number of organic and inorganic acids and bases to form pharmaceutically acceptable salts. Pharmaceutically acceptable salts of the compound of the present invention are contemplated within the scope of the present application. The term "pharmaceutically acceptable salt" as used herein, refers to any salt of the compound of the invention that is substantially non-toxic to living organisms. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008); and S. M. Berge, et al., "Pharmaceutical Salts", *Journal of Pharmaceutical Sciences*, Vol 66, No. 1, January 1977.

Abbreviations used herein are defined as follows:
"Brine" means saturated NaCl.
"BSA" means bovine serum albumin
"DAST" means diethylaminosulfur trifluoride
"DCM" means dichloromethane.
"DMF" means n,n-dimethylformamide
"DMSO" means dimethyl sulfoxide (perdeuterated [d6] if for NMR).
"EtOAc" means ethyl acetate.
"FLIPR" means fluorescence imaging plate reader.
"HBSS" means Hank's Buffered Salt Solution.
"HEPES" means 4-(2-hydroxyethyl)-1-piperazine ethanesulfonic acid.
"HPLC" means high pressure liquid chromatography.
"hr." or "h" means hour or hours.
"$IC_{50}$" means the concentration at which 50% of the maximum inhibition is achieved.
"LCMS" means liquid chromatography mass spectrometry.
"MeOH" means methanol.
"MS" means mass spectroscopy or mass spectrum.
"MTBE" means methyl tert-butyl ether.
"PE" means petroleum ether solvent.
"THF" means tetrahydrofuran.

A compound of Formula I may be prepared by processes known in the chemical arts or by a novel process described herein. A process for the preparation of a compound of Formula I and novel intermediates for the manufacture of a compound of Formula I, provide further features of the invention and are illustrated by the following procedures.

Generally, a compound of Formula I may be prepared from a compound of Formula II (Scheme 1). More specifically, a compound of Formula II is reacted with a compound of Formula III in the presence of a suitable transition metal catalysis such as tris(dibenylideneacetone)dipalladium and a base such as cesium carbonate in a suitable solvent to provide a compound of Formula I. Suitable solvents include dioxane. A compound of Formula III may be prepared by methods known in the chemical arts as well as methods provided in the Preparations and Examples.

Alternatively, a compound of Formula I may be prepared from a compound of Formula IV (Scheme 1). More specifically, a compound of Formula IV is reacted with a suitable $R^1$-boron reagent compound in the presence of a suitable transition metal catalysis such as tris(dibenylideneacetone) dipalladium and a base such as cesium carbonate in a suitable solvent to provide a compound of Formula I. Suitable solvents include dioxane. A suitable $R^1$-boron reagent compound may be prepared by methods known in the chemical arts as well as methods provided in the Preparations and Examples.

It is understood that certain functional groups employed during the preparation of a compound of Formula I may act as precursors to groups ultimately encompassed in a compound of Formula I. Such groups are known in the chemical arts and may be disclosed in the Preparations and Examples. For instance, the R5-O—(C=O)— group of a compound of Formula I may be acquired through chemical transformation a suitable precursor group such as cyano (—CN).

Scheme 1

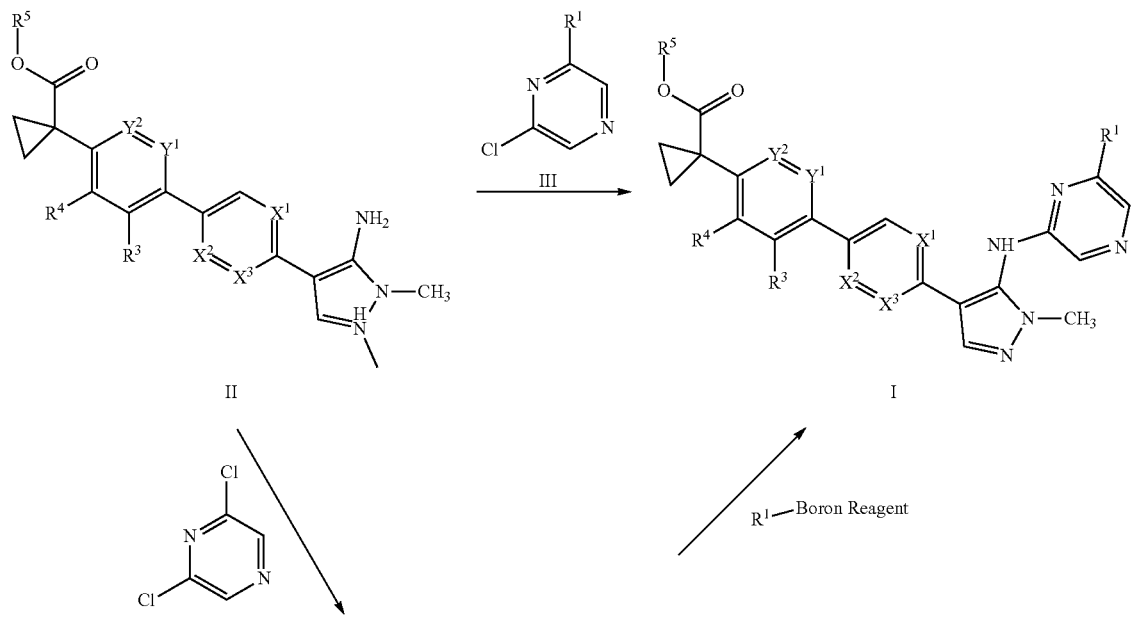

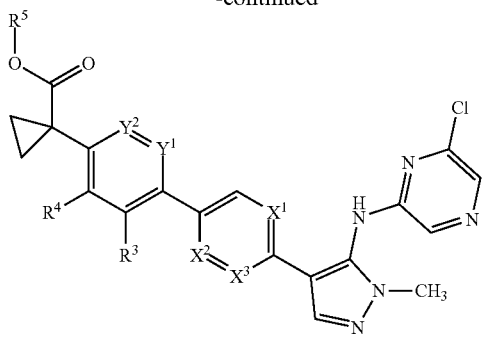

IV

Alternatively, a compound of Formula I may be prepared from a compound of Formula V and a compound of Formula VI (Scheme 2). More specifically, a compound of Formula VI is first reacted with bis(pinacolato)diboron in the presence of a suitable transition metal catalyst such as [1,1'-bis(diphenylphosphino) ferrocene]dichloropalladium in a suitable solvent such as dioxane to provide an intermediate pinacolatoboron compound which is further reacted compound of Formula V in the presence of a base such as sodium carbonate to provide a compound of Formula I. A compound of Formula V or a compound of Formula VI may be prepared by methods known in the chemical arts as well as methods provided in the Preparations and Examples.

Scheme 2

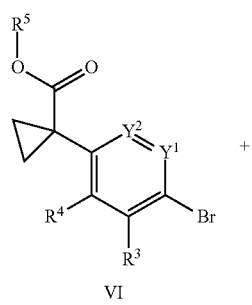

VI

+

V

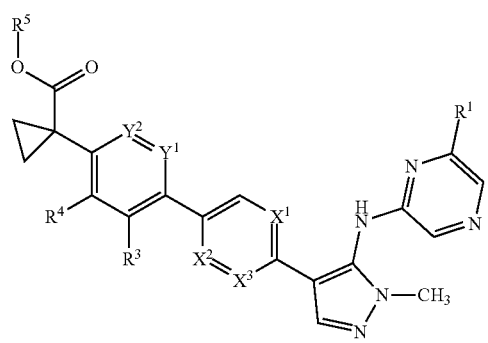

I

As shown in Scheme 3, compounds of Formula II may be prepared by reacting a compound of Formula VIII with a pinacolatoboron compound of Formula VII in the presence of a suitable transition metal catalysis such as [1,1'-bis(diphenylphosphino)ferrocene]dichloropalladium and a suitable base such as sodium carbonate in a suitable solvent. Suitable solvents include dioxane.

It is understood reacting groups suitable for coupling methods are known in the chemical arts as well as disclosed in the Preparations and Examples. For instance, the pinacolatoboron reacting group of a compound of Formula VII may be substituted with alternative coupling groups such as tributylstannyl.

Alternatively, a compound of Formula II may be prepared from a compound of Formula IX (Scheme 3). More specifically, a compound of Formula IX is reacted with 4-bromo-2-methyl-pyrazol-3-amine in the presence of a suitable transition metal catalysis such as tris(dibenylideneacetone)dipalladium and a base such as cesium carbonate in a suitable solvent to provide a compound of Formula II. Suitable solvents include dioxane.

A compound of Formula VII, Formula VIII or Formula IX may be prepared by methods known in the chemical arts as well as methods provided in the Preparations and Examples.

Scheme 3

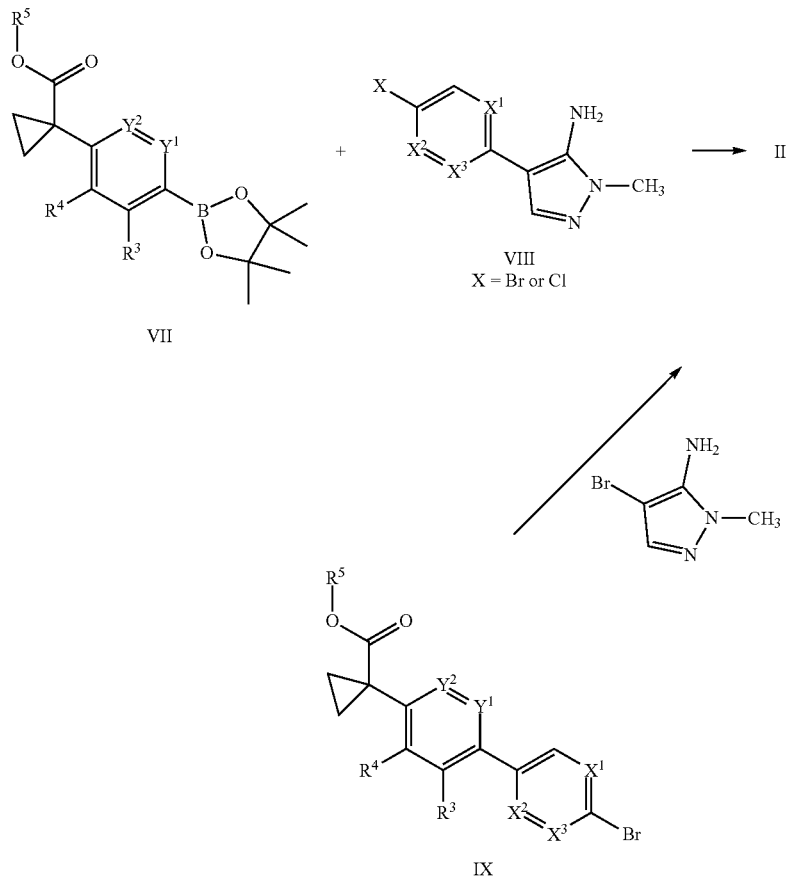

Preparation 1: 2-chloro-6-(cyclopropoxy)pyrazine

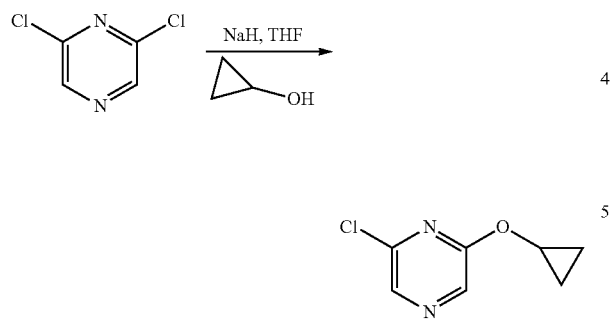

Add sodium hydride (1.36 g, 34.1 mmol, 60 mass %) to cyclopropanol (1.00 g, 17.0 mmol) in tetrahydrofuran (10 mL) at 0° C., and the reaction mixture is stirred at 20° C. for 30 min. Then 2,6-dichloropyrazine (2.57 g. 17.0 mmol) is added and the mixture is stirred at 20° C. for 12 h. The reaction mixture is poured into saturated NH₄Cl (30 mL). The resulting mixture is extracted with EtOAc (30 mL×3). The combined organic phases are washed with water (30 mL), brine (30 mL), dried over anhydrous sodium sulfate, filtered and concentrated to afford title compound (2.50 g, 81.7%) as a white solid. LCMS (m/z): 170.9 [M+H]⁺.

Preparation 2:
2-chloro-6-(1,1-difluoroethyl)pyrazine

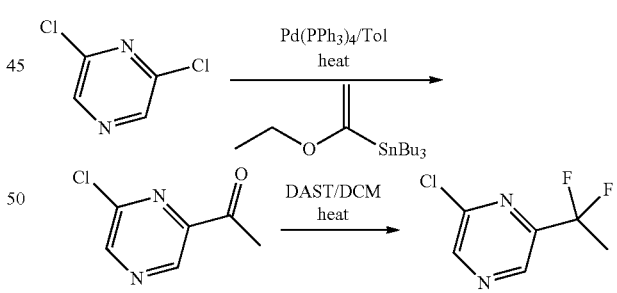

1. Synthesis of 1-(6-chloropyrazin-2-yl)ethanone

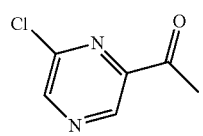

Add 2,6-dichloropyrazine (3.00 g, 20.1 mmol) and tetrakis(triphenylphosphine) palladium (2.33 g, 2.01 mmol) to tributyl(1-ethoxyvinyl)stannane (8.08 g, 22.2 mmol) in anhydrous toluene (100 mL) under N₂ atmosphere. Then the mixture is stirred at 100° C. under N₂ atmosphere for 16 hrs. After cooling to room temperature, the mixture is poured into a mixture of sat. KF aq. (300 mL) and MTBE/EtOAc (1/1, 200 mL) and stirred for 1 h. The solids are filtered on celite and washed with MTBE/EtOAc (1/1, 150 mL×2). The filtrate is separated. The aqueous layer is extracted with EtOAc (200 mL). The combined organic layer is concentrated under reduced pressure. The residue is taken up in acetone (200 mL) and treated with 1 N HCl aq. (120 mL), stirred at 10-15° C. for 1 h. The mixture is concentrated under reduced pressure to remove most acetone, and the residue is extracted with MTBE/EtOAc (1/1, 100 mL×3). The combined organic layer is washed with sat. NaHCO₃ (150 mL×2), brine (150 mL×2), dried over anhydrous Na₂SO₄, filtered, concentrated under reduced pressure, the residue is purified by column chromatography on silica gel eluting with 0-10% EtOAc in PE to afford title compound (1.0 g, 31.4%) as a yellow solid.

¹H NMR (400 MHz, CDCl₃): δ=9.14 (s, 1H), 8.80 (s, 1H), 2.74 (s, 3H).

2. Synthesis of 2-chloro-6-(1,1-difluoroethyl)pyrazine

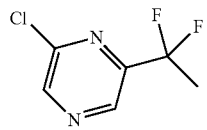

Add diethylaminosulfur trifluoride (2.81 g, 17.2 mmol) to 1-(6-chloropyrazin-2-yl)ethanone (540 mg, 1.15 mmol) in dichloromethane (30 mL) at 0° C. and the solution is stirred at 15° C. for 12 h. The reaction mixture is poured into ice water (30 mL), and aq. Na₂CO₃ (10% mass in water) is added dropwise to adjust pH=8. The reaction mixture is diluted with 30 mL water and extracted with DCM (40 mL×3). The organic layer is dried over Na₂SO₄, filtered and concentrated under reduced pressure to afford crude product (800 mg) as yellow oil. The crude product is purified by column chromatography on silica gel eluting with 0-30% EA in PE to give title compound (385 mg, 90 mass %, 56.3%) as a yellow oil.

¹H NMR (400 MHz, CDCl₃): δ=8.86 (s, 1H), 8.71 (s, 1H), 2.05 (t, J=18.4 Hz, 3H).

Preparation 3: 2-chloro-6-(1-fluoro-1-methyl-ethyl)pyrazine

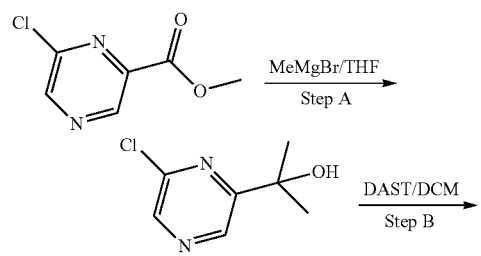

1. Synthesis of 2-(6-chloropyrazin-2-yl)propan-2-ol

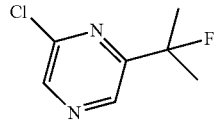

Add methyl 6-chloropyrazine-2-carboxylate (20.0 g, 116 mmol) in THF (100 mL) to methylmagnesium bromide (3.0 mol/L) in diethyl ether (120 g, 348 mmol, 3.0 mol/L) at 0° C. and the mixture is stirred at this temperature for 2 h. The reaction is quenched with 1.0M HCl solution (100 mL) and extracted with EtOAc (100 mL×3). The combined organic layers are washed with brine (100 mL), dried over anhydrous sodium sulfate, concentrated to afford a yellow oil. The yellow oil is purified by column chromatography on silica gel eluting with 0-30% EA in PE to afford title compound (3.80 g, 18.0%) as brown oil. LCMS (m/z): 172.8 [M+H]⁺.

2. Synthesis of 2-chloro-6-(1-fluoro-1-methyl-ethyl)pyrazine

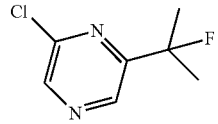

Add DAST (6.74 g, 41.8 mmol) to 2-(6-chloropyrazin-2-yl)propan-2-ol (3.80 g, 20.9 mmol) in CH₂Cl₂ (30 mL) at 0° C., then the reaction mixture is stirred at 0° C. for 1 h. The reaction is quenched with water (20 mL) and extracted with EtOAc (50 mL×3). The combined organic layers are washed with sat. NaHCO₃ (20 mL), 1 M HCl (20 mL) and brine (30 mL), and dried over anhydrous sodium sulfate and to afford a yellow oil. The crude product was purified column chromatography on silica gel eluting with 0-30% EA in PE to afford title compound (3.40 g, 84%) as yellow oil. LCMS (m/z): 174.9 [M+H]⁺.

¹H NMR (400 MHz, CDCl₃) δ=8.75 (s, 1H), 8.53 (s, 1H), 1.76 (d, J=22.4 Hz, 6H)

Preparation 4: 2-chloro-6-isopropoxy-pyrazine

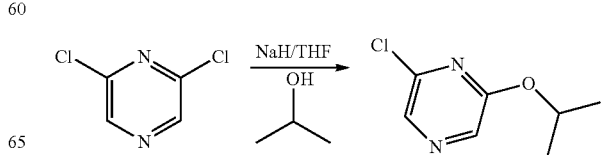

Add sodium hydride in oil (1.07 g, 26.8 mmol, 60 mass %) to propan-2-ol (0.807 g, 13.4 mmol) in THF (20 mL) at 0° C. and the mixture is stirred for 20 min at this temperature. Then 2,6-dichloropyrazine (2.00 g, 13.4 mmol) is added and the mixture is stirred at 20° C. for 18 hours. The reaction mixture is poured into a saturated NH$_4$Cl solution (100 mL) and extracted with EtOAc (50 mL×2). The combined organic layers are washed with brine, dried over sodium sulfate and concentrated to afford the title compound (2.20 g, 85.4%) as brown oil.

$^1$H NMR (400 MHz, CDCl$_3$) δ=7.93 (s, 1H), 7.88 (s, 1H), 5.25-5.04 (m, 1H), 1.21 (d, J=6.4 Hz, 6H).

Preparation 5: 2-chloro-6-isopropyl-pyrazine

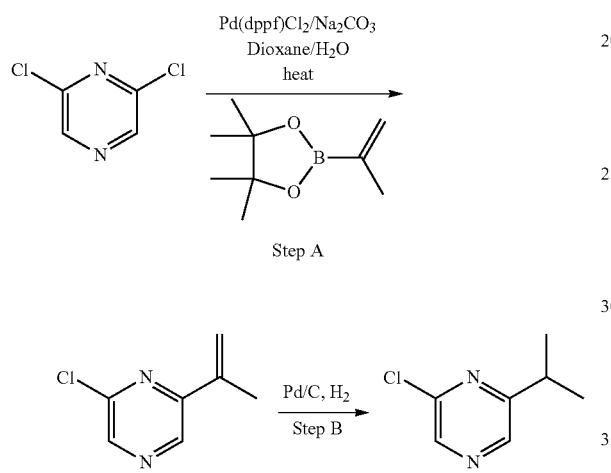

1. Synthesis of 2-chloro-6-isopropenyl-pyrazine

Add 2-isopropenyl-4,4,5,5-tetramethyl-1,3,2-dioxaborolane (6.00 g, 35.4 mmol), [1,1'-bis(diphenylphosphino)ferrocene] dichloropalladium(II) (1.32 g, 1.77 mmol) and sodium carbonate (9.37 g, 88.4 mmol) to 2,6-dichloropyrazine (10.6 g, 70.7 mmol) in 1,4-dioxane (80 mL) and water (20 mL) to under N$_2$. The mixture is stirred at 100° C. for 6 hours. The solid is filtered off. The mixture is diluted with water (100 mL) and extracted with EtOAc (200 mL×3). The combined organic layers are washed with brine (300 mL), dried over anhydrous Na$_2$SO$_4$, filtered and evaporated to afford the crude product. The crude product is purified by column chromatography on silica gel eluting with 0-50% EtOAc in PE to afford title compound (3.0 g, 54.9% Yield) as colorless oil.

$^1$H NMR (400 MHz, CDCl$_3$) δ=8.65 (s, 1H), 8.45 (s, 1H), 6.02 (s, 1H), 5.47 (s, 1H), 2.21 (s, 3H).

2. Synthesis of 2-chloro-6-isopropyl-pyrazine

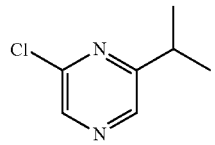

Add palladium on activated carbon (500 mg, 10 mass %) to 2-chloro-6-isopropenyl-pyrazine (5.00 g, 19.4 mmol, 60 mass %) in ethyl acetate (40 mL) under N$_2$. It is stirred at 20° C. under molecular hydrogen (15 psi) for 12 hours. The solid is filtered off. The mixture is evaporated to afford the crude. The residue is purified by flash chromatography eluting with petroleum ether:EtOAc (3:1) to afford title compound (1.56 g, 45% Yield) as colorless oil. LCMS (m/z): 156.8 [M+H]$^+$.

$^1$H NMR: (400 MHz, CDCl$_3$) δ=8.42 (s, 1H), 8.38 (s, 1H), 3.14-3.05 (m, 1H), 1.34 (d, J=7.2 Hz, 6H).

Preparation 6: 2-tert-butoxy-6-chloro-pyrazine

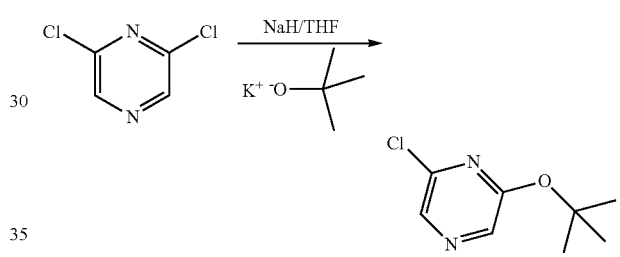

Add 2,6-dichloropyrazine (2.0 g, 13 mmol) in THF (20 mL) to potassium tert-butoxide (1.0 g, 8.8 mmol) at 0° C., the reaction mixture is stirred at 0° C. for 20 min, then the reaction mixture is stirred at 20° C. for 18 hours. The reaction mixture is poured into a saturated NH$_4$Cl solution (100 mL) and extracted with EtOAc (50 mL×2). The combined organic layers are washed with brine, dried over sodium sulfate and concentrated. The residue is purified by flash chromatography eluting with petroleum ether:EtOAc (3:1) to afford title compound (2.18 g, 86%) as white solid. LCMS (m/z): 131.2 [M-CH$_2$=C(CH$_3$)$_2$+H]$^+$.

Preparation 7: 2-chloro-6-(cyclobutoxy)pyrazine

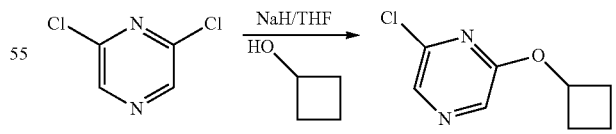

Add cyclobutanol (2.00 g, 17.0 mmol) to sodium hydride (0.5 g, 19.8 mmol, 60 mass %) in tetrahydrofuran (20 mL) at 0° C. and the reaction mixture is stirred at 20° C. for 30 min. then 2,6-dichloropyrazine (2.0 g, 13.0 mmol) is added and the mixture is stirred at 20° C. for 12 h. The reaction mixture is poured into saturated NH$_4$Cl (30 mL). The result mixture is extracted with EtOAc (30 mL×3). The combined organic phases are washed with water (30 mL), brine (30 mL), dried over anhydrous sodium sulfate, filtered and concentrated to afford title compound (2.1 g, 87%) as a white solid. LCMS (m/z): 185.2 [M+H]+.

Preparation 8:
2-chloro-6-(3,3-difluorocyclobutoxy)pyrazine

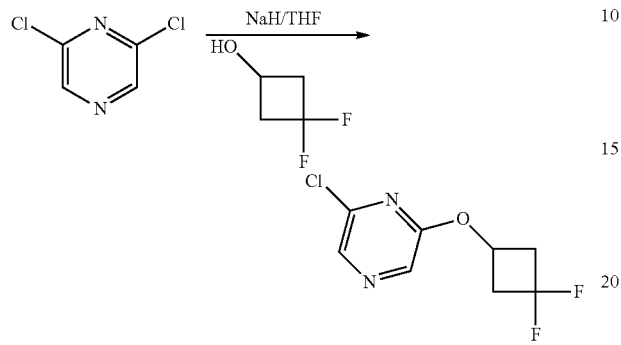

Add 3,3-difluorocyclobutanol (2.00 g, 17.0 mmol) to sodium hydride (0.5 g, 19.8 mmol, 60 mass %) in tetrahydrofuran (20 mL) at 0° C., then the mixture is stirred at 20° C. for 30 min, 2,6-dichloropyrazine (2.0 g, 13.0 mmol) is added and the mixture is stirred at 20° C. for 12 h. The reaction mixture is poured into saturated NH4Cl (30 mL). The result mixture is extracted with EtOAc (30 mL×3). The combined organic phases are washed with water (30 mL), brine (30 mL), dried over anhydrous sodium sulfate, filtered and concentrated to afford the title compound (2.4 g, 85%). LCMS (m/z): 221.1 [M+H]+.

Preparation 9:
2-chloro-6-(1-methoxy-1-methyl-ethyl)pyrazine

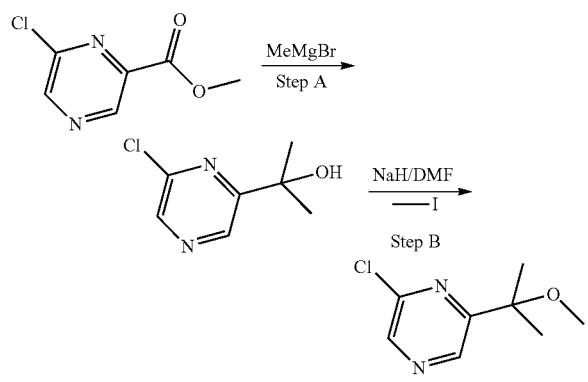

1. Synthesis of 2-(6-chloropyrazin-2-yl)propan-2-ol

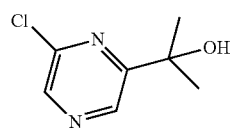

Add methylmagnesium bromide (3 mol/L) in ether (28.7 mL, 86.1 mmol, 3 mol/L) to a solution of methyl 6-chloropyrazine-2-carboxylate (5.00 g, 28.7 mmol) in tetrahydrofuran (40 mL) at 0° C. and the mixture is stirred at 0° C. for 2 hours. The reaction is quenched with 1.0 M HCl solution (50 mL) and extracted with EtOAc (50 mL×3). The combined organic layers are washed with brine (30 mL), dried over anhydrous sodium sulfate, concentrated to afford a yellow oil. The yellow oil was purified by flash chromatography eluting with petroleum ether/EtOAc (3:1) to afford title compound (600 mg, 11.5%) as brown oil.

2. Synthesis of
2-chloro-6-(1-methoxy-1-methyl-ethyl)pyrazine

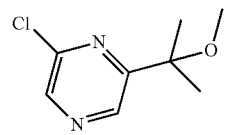

Add sodium hydride (0.0792 g, 1.98 mmol, 60 mass %) to a solution of 2-(6-chloropyrazin-2-yl)propan-2-ol (180 mg, 0.991 mmol) in DMF (1 mL) at 0° C., and the mixture is stirred for 30 min, then iodomethane (0.213 g, 1.49 mmol) is added to the solution and the mixture is stirred at 20° C. for 2 h. The reaction is quenched with water (20 mL) and extracted with EtOAc (20 mL×3). The combined organic layers are washed with brine (30 mL), dried over anhydrous sodium sulfate and concentrated to afford title compound (150 mg, 77.1%) as brown oil.

$^1$H NMR (400 MHz, CDCl$_3$) δ=8.75 (s, 1H), 8.48 (s, 1H), 3.25 (s, 3H), 1.57 (s, 6H).

Preparation 10: 4-(5-bromo-2-pyridyl)-2-methylpyrazol-3-amine

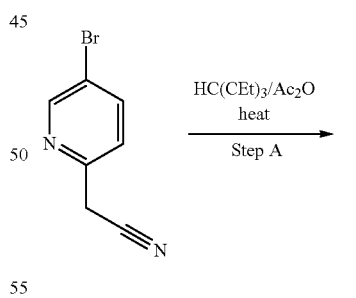

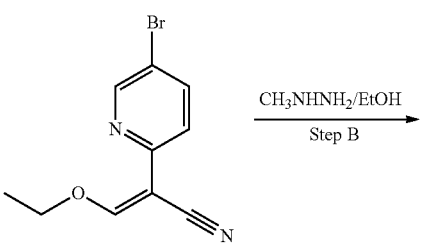

Preparation 11: N-[4-(5-bromo-2-pyridyl)-2-methyl-pyrazol-3-yl]-6-isopropoxy-pyrazin-2-amine

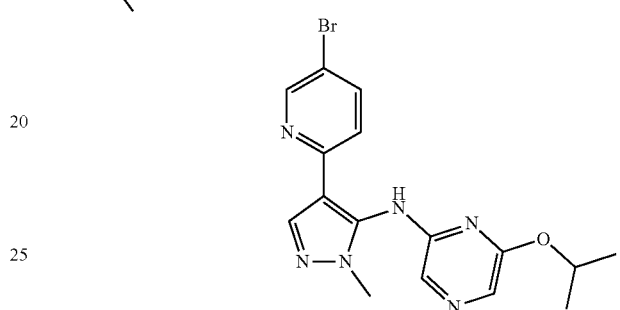

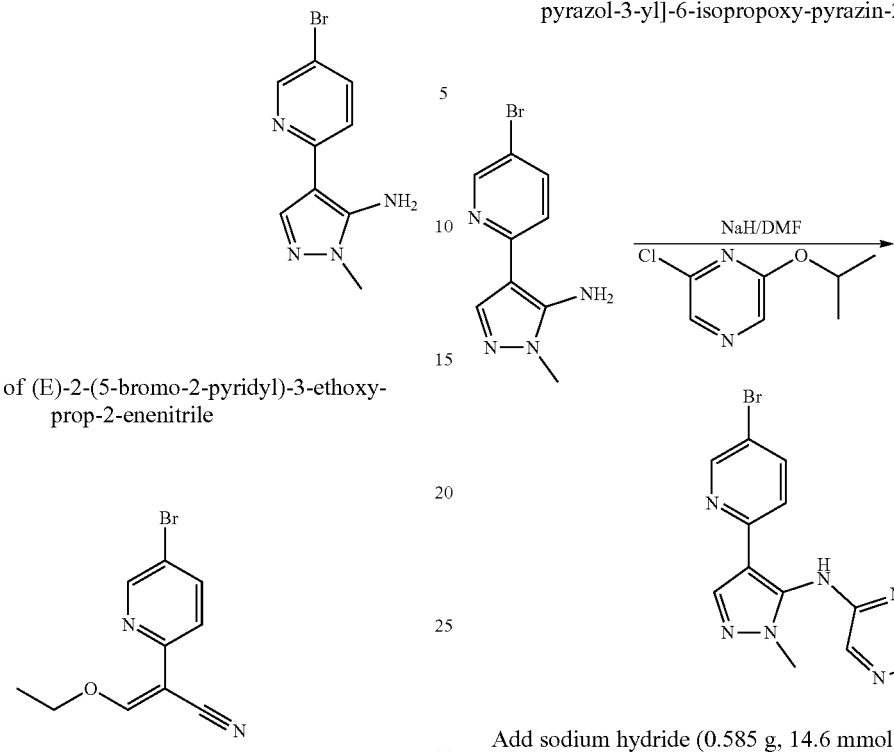

Add sodium hydride (0.585 g, 14.6 mmol, 60 mass %) to a solution of 4-(5-bromo-2-pyridyl)-2-methyl-pyrazol-3-amine (1.30 g, 4.88 mmol) in DMF (15 mL). The reaction mixture is heated to 50° C. and then 2-chloro-6-isopropoxy-pyrazine (0.975 g, 5.37 mmol) is added. The reaction mixture is stirred at 50° C. for 3 hours. The reaction mixture is poured into ammonium chloride solution (20 ml) and extracted with EtOAc (30 mL×2). The combined organic layers are washed with brine (20 mL×2), dried over sodium sulfate and concentrated to afford the crude. The residue is purified by column chromatography (0-80% EA in PE) to give title compound (1.20 g, 60.0%) as a yellow oil. LCMS (m/z): 389.0/390.8 [M+H, $Br^{79}/Br^{81}$]$^+$.

EXAMPLE 1A

Methyl 1-[4-[6-[5-[(6-tert-butoxypyrazin-2-yl)amino]-1-methyl-pyrazol-4-yl]-3-pyridyl]phenyl]cyclopropanecarboxylate 1. Synthesis of methyl 1-[4-[6-(5-amino-1-methyl-pyrazol-4-yl)-3-pyridyl]phenyl]cyclopropanecarboxylate

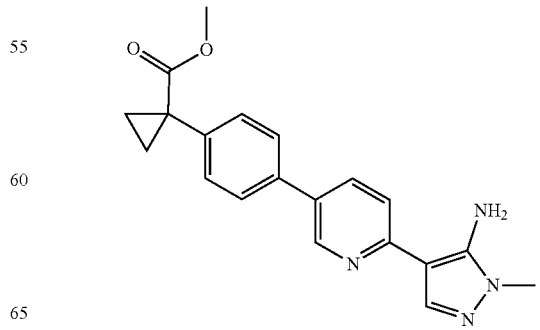

1. Synthesis of (E)-2-(5-bromo-2-pyridyl)-3-ethoxy-prop-2-enenitrile

Add 2-(5-bromo-2-pyridyl)acetonitrile (5.00 g, 25.1 mmol) in triethyl orthoformate (30 mL) to acetic anhydride (7.93 g, 75.4 mmol) and the mixture is stirred at 125° C. for 36 h. The reaction mixture is concentrated to afford the title compound (5.6 g, 88%) as a brown crude without further purification for next step. LCMS (m/z): 253.1 [M+H]$^+$.

2. Synthesis of 4-(5-bromo-2-pyridyl)-2-methyl-pyrazol-3-amine

Add (E)-2-(5-bromo-2-pyridyl)-3-ethoxy-prop-2-enenitrile (5.5 g, 21.8 mmol) in ethanol (10 mL) to methylhydrazine (10 mL). The reaction mixture is heated to 100° C. and stirred for 3 hours. Then the reaction mixture is concentrated and purified by flash chromatography eluting with petroleum ether:EtOAc (3:1) to afford title compound (3.15 g, 57.1%). LCMS (m/z): 254.8/256.8 [M+H, $Br^{79}/Br^{81}$]$^+$.

Add 4-(5-bromo-2-pyridyl)-2-methyl-pyrazol-3-amine (0.9 g, 3.56 mmol %), sodium carbonate (0.754 g, 7.11 mmol), 1-[4-(4,4,5,5-tetramethyl-1,3,2-dioxaborolan-2-yl)phenyl]cyclopropanecarboxylate (1.19 g, 3.73 mmol) in in 1,4-dioxane (10.0 mL) and water (2 mL) to [1,1'-bis(diphenylphosphino)ferrocene]dichloropalladium(II) (0.266 g, 0.356 mmol) under N$_2$. Then the reaction mixture is stirred at 100° C. for 4 h under N$_2$. The reaction mixture is concentrated to give a black solid, which is purified by flash chromatography eluting with EtOAc:CH$_2$Cl$_2$ (1:1) to afford title compound (1.1 g, 89.2%) as a brown solid. LCMS (m/z): 348.9 [M+H]$^+$.

2. Synthesis of methyl 1-[4-[6-[5-[(6-tert-butoxypyrazin-2-yl)amino]-1-methyl-pyrazol-4-yl]-3-pyridyl]phenyl]cyclopropanecarboxylate

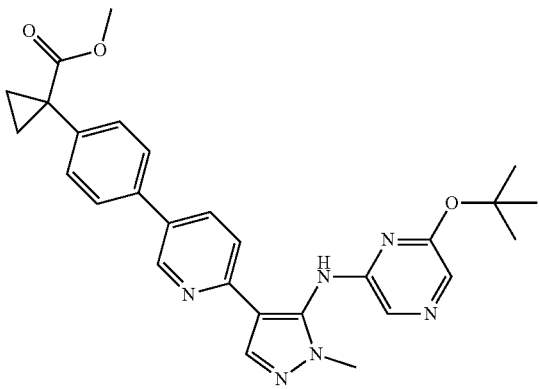 [SMILES: COC(=O)C1(c2ccc(-c3ccc(-c4cnn(C)c4Nc4cncc(OC(C)(C)C)n4)nc3)cc2)CC1]

Add tris(dibenzylideneacetone)dipalladium (116 mg, 0.123 mmol) and 4,5-bis(diphenylphosphino)-9,9-dimethylxanthene (110 mg, 0.185 mmol) to a solution of methyl 1-[4-[6-(5-amino-1-methyl-pyrazol-4-yl)-3-pyridyl]phenyl]cyclopropanecarboxylate (430 mg, 1.23 mmol), 2-tert-butoxy-6-chloro-pyrazine (254 mg, 1.23 mmol) and cesium carbonate (1.21 g, 3.7 mmol) in O$_2$-free 1,4-dioxane (4 mL) at 25° C. The mixture is then stirred at 100° C. for 6 hr. The mixture is filtered through a pad of silica gel and the filtrate is concentrated. The residue is purified by flash chromatograph eluting with PE/EtOAc (1:1) to afford the title compound (160 mg, 25%). LCMS (m/z): 499.3 [M+H]$^+$.

EXAMPLE 1B

1-[4-[6-[5-[(6-tert-butoxypyrazin-2-yl)amino]-1-methyl-pyrazol-4-yl]-3-pyridyl]phenyl]cyclopropanecarboxylic acid

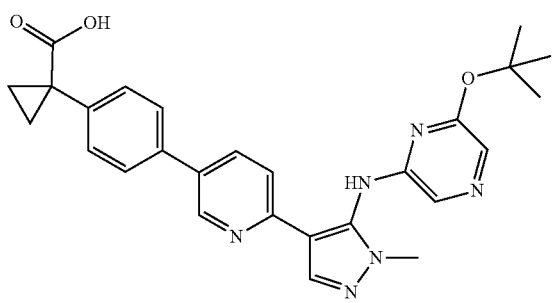 [SMILES: Cn1ncc(-c2ccc(-c3ccc(C4(C(=O)O)CC4)cc3)cn2)c1Nc1cncc(OC(C)(C)C)n1]

Add lithium hydroxide monohydrate (200 mg, 8.1 mmol) to methyl 1-[4-[6-[5-[(6-tert-butoxypyrazin-2-yl)amino]-1-methyl-pyrazol-4-yl]-3-pyridyl]phenyl]cyclopropanecarboxylate (160 mg, 0.32 mmol) in MeOH (3 mL) and water (3 mL). The resulting mixture is stirred for 12 hours 25° C. The mixture is concentrated and diluted with water (5 mL). The mixture is acidified with HCl (1M) to pH=4-6. The mixture is extracted with DCM (5 mL×5). The combined organic phases are washed with brine (10 mL), concentrated, purified by prep-HPLC [Column SunFire C18, 5 µm, 30×100 mm Condition: water (0.1% FA)-ACN Begin B 29 End B 44 Gradient Time (min) 10 100% B Hold Time (min) 9.0 FlowRate (ml/min) 30] to afford the title compound (100 mg, 64%) as yellow solid. LCMS (m/z): 485.3 [M+H]$^+$.

$^1$H NMR (500 MHz, DMSO-d6) δ 9.15 (s, 1H), 8.80 (s, 1H), 8.08 (s, 1H), 7.98 (m, 1H), 7.76 (s, 1H), 7.83 (s, 1H), 7.60-7.57 (m, 3H), 7.54 (s, 1H), 7.43-7.40 (m, 3H), 3.67 (s, 3H), 1.48 (m, 2H), 1.23-1.23 (s, 9H), 1.15 (m, 2H).

EXAMPLE 2A

Methyl 1-[4-[6-[5-[[6-(cyclobutoxy)pyrazin-2-yl]amino]-1-methyl-pyrazol-4-yl]-3-pyridyl]phenyl]cyclopropanecarboxylate

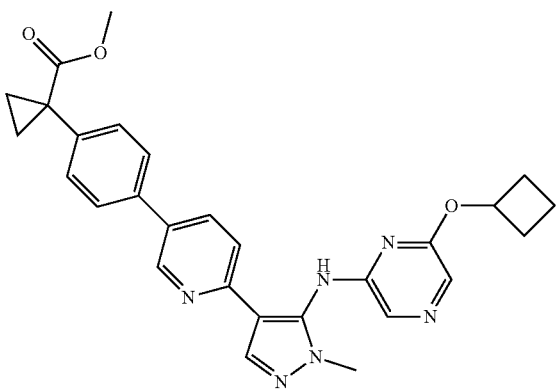 [SMILES: COC(=O)C1(c2ccc(-c3ccc(-c4cnn(C)c4Nc4cncc(OC5CCC5)n4)nc3)cc2)CC1]

Under O$_2$ free condition, add tris(dibenzylideneacetone)dipalladium (116 mg, 0.123 mmol) and 4,5-bis(diphenylphosphino)-9,9-dimethylxanthene (110 mg, 0.185 mmol) to the 1,4-dioxane (4 mL) solution of methyl 1-[4-[6-(5-amino-1-methyl-pyrazol-4-yl)-3-pyridyl]phenyl]cyclopropane carboxylate (430 mg, 1.23 mmol) (prepared according to Example 1A), 2-chloro-6-(cyclobutoxy)pyrazine (250 mg, 1.36 mmol) and cesium carbonate (1.21 g, 3.7 mmol)), stirred at 100° C. for 6 hr. The mixture is filtered through a pad of silica gel (200-300 mush) and the filtrate is concentrated. The residue is purified by flash chromatograph eluting with petroleum ether:EtOAc (1:1) to afford the title compound (260 mg, 41%). LCMS (m/z): 497.3 [M+H]$^+$.

EXAMPLE 2B

1-[4-[6-[5-[[6-(cyclobutoxy)pyrazin-2-yl]amino]-1-methyl-pyrazol-4-yl]-3-pyridyl]phenyl]cyclopropanecarboxylic acid

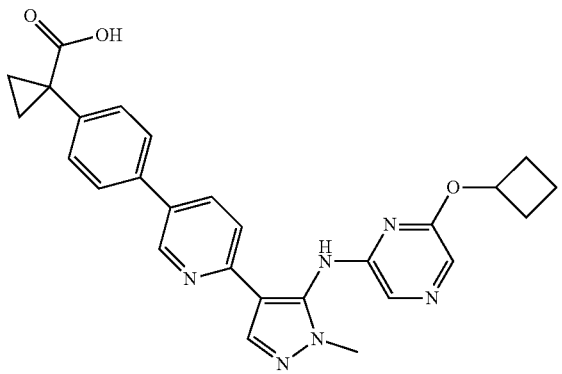 [SMILES: Cn1ncc(-c2ccc(-c3ccc(C4(C(=O)O)CC4)cc3)cn2)c1Nc1cncc(OC2CCC2)n1]

Add lithium hydroxide monohydrate (200 mg, 8.1 mmol) to a solution of methyl 1-[4-[6-[5-[[6-(cyclobutoxy)pyrazin-2-yl]amino]-1-methyl-pyrazol-4-yl]-3-pyridyl]phenyl]cyclopropanecarboxylate (260 mg, 0.51 mmol) in MeOH (3 mL) and water (3 mL) and the mixture is stirred for 12 hours 25° C. The mixture is concentrated and diluted with water (5 mL). The mixture is acidified with HCl (1M) to pH=4-6. The mixture is extracted with DCM (5 mL×5). The combined organic phases are washed with brine (10 mL), concentrated and then purified by prep-HPLC [Column SunFire C18, 5 μm, 30×100 mm Condition: water (0.1% FA)-ACN Begin B 29 End B 44 Gradient Time (min) 10 100% B Hold Time (min) 8.5 FlowRate (ml/min) 30] to afford the title compound (50 mg, 23%) as yellow solid. LCMS (m/z): 483.3 [M+H]$^+$.

$^1$H NMR (500 MHz, DMSO-d6) δ 9.32 (s, 1H), 8.80 (s, 1H), 8.80 (s, 1H), 8.08 (s, 1H), 8.00 (m, 1H), 7.79 (s, 1H), 7.63-7.57 (m, 3H), 7.54 (s, 1H), 7.41 (m, 2H), 4.63 (m, 1H) 3.68 (s, 3H), 2.11 (m, 2H), 2.02 (m, 2H). 1.68 (m, 1H), 1.49 (m, 1H), 1.46 (m, 2H), 1.14 (m, 2H).

EXAMPLE 3A

Methyl 1-[4-[6-[5-[[6-(cyclopropoxy)pyrazin-2-yl]amino]-1-methyl-pyrazol-4-yl]-5-fluoro-3-pyridyl]phenyl]cyclopropanecarboxylate

1. Synthesis of 2-(5-chloro-3-fluoro-2-pyridyl)acetonitrile

Add n-butyllithium in hexanes (110 g, 381 mmol, 2.5 mol/L) to a solution of acetonitrile (17.2 g, 419 mmol) in anhydrous THF (50 mL) at −78° C. under nitrogen. The mixture is stirred at −78° C. for 30 min. Then added with a solution of 5-chloro-2,3-difluoro-pyridine (60.0 g, 381 mmol) in THF (100 mL) and the mixture is stirred at −78° C. for 2 h. The reaction mixture is warmed to 20° C. and stirred for 1 h. The reaction mixture is quenched with sat. NH$_4$Cl (300 mL). The reaction mixture is extracted with EtOAc (200 mL×3). The combined organic phases are washed with water (100 mL), brine (100 mL), concentrated to afford a yellow residue, which is purified by column chromatography on silica gel eluting with PE:EtOAc (10:1) to afford title compound 2-(5-chloro-3-fluoro-2-pyridyl)acetonitrile (20.0 g, 30.8%) as a yellow oil. LCMS (m/z): 170.8 [M+H]$^+$.

2. Synthesis of (Z)-2-(5-chloro-3-fluoro-2-pyridyl)-3-ethoxy-prop-2-enenitrile

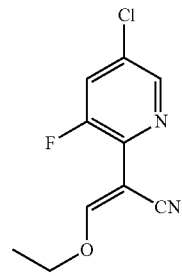

Add 2-(5-chloro-3-fluoro-2-pyridyl)acetonitrile (20.0 g, 117 mmol) in acetic anhydride (47.9 g, 469 mmol) to triethyl orthoformate (100 mL) and the mixture is stirred at 125° C. for 36 h. The reaction mixture is concentrated to afford title compound (Z)-2-(5-chloro-3-fluoro-2-pyridyl)-3-ethoxy-prop-2-enenitrile (45.7 g, 117 mmol, 58 mass %, 99.5%) as a brown oil. it is used for the next step directly without further purification. LCMS (m/z): 226.9 [M+H]$^+$.

3. Synthesis of 4-(5-chloro-3-fluoro-2-pyridyl)-2-methyl-pyrazol-3-amine

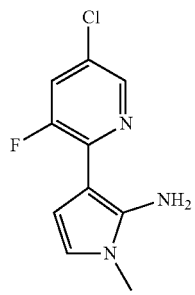

Add methylhydrazine (40.4 g, 351 mmol, 40 mass %) to a solution of 2-(5-chloro-3-fluoro-2-pyridyl)-3-ethoxy-prop-2-enenitrile (45.7 g, 117 mmol, 58 mass %) in ethanol (100 mL), and the reaction mixture is stirred at 100° C. for 3 h. The reaction mixture is concentrated and purified by column chromatography on silica gel eluting with PE:EtOAc (1:1) to afford title (5.50 g, 19.7%) as a brown solid. LCMS (m/z): 226.9 [M+H]$^+$.

4. Synthesis of methyl 1-[4-[6-(5-amino-1-methyl-pyrazol-4-yl)-5-fluoro-3-pyridyl]phenyl]cyclopropanecarboxylate

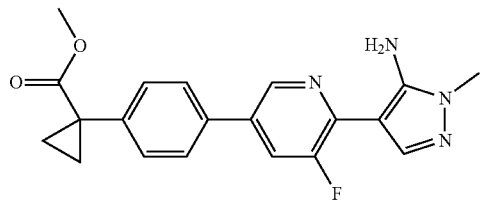 [SMILES: COC(=O)C1(c2ccc(-c3cnc(-c4cnn(C)c4N)c(F)c3)cc2)CC1]

Add Pd$_2$(dba)$_3$ (0.576 g, 0.629 mmol) and tricyclohexylphosphine (0.184 g, 0.629 mmol) to sodium carbonate (1.33 g, 12.6 mmol), methyl, 1-[4-(4,4,5,5-tetramethyl-1,3,2-dioxaborolan-2-yl)phenyl]cyclopropane carboxylate (1.55 g, 4.61 mmol, 90 mass %) and 4-(5-chloro-3-fluoro-2-pyridyl)-2-methyl-pyrazol-3-amine (1.00 g, 4.19 mmol) in 1,4-dioxane (16 mL) and water (4 mL), then the reaction mixture is stirred at 90° C. for 1 h under nitrogen. The reaction mixture is concentrated to afford a black residue, which is purified by column chromatography on silica gel eluting with PE:EtOAc (2:3) to afford title (1.20 g, 74.2%) as a brown solid. LCMS (m/z): 367.1 [M+H]$^+$.

5. Synthesis of methyl 1-[4-[6-[5-[[6-(cyclopropoxy)pyrazin-2-yl]amino]-1-methyl-pyrazol-4-yl]-5-fluoro-3-pyridyl]phenyl]cyclopropanecarboxylate

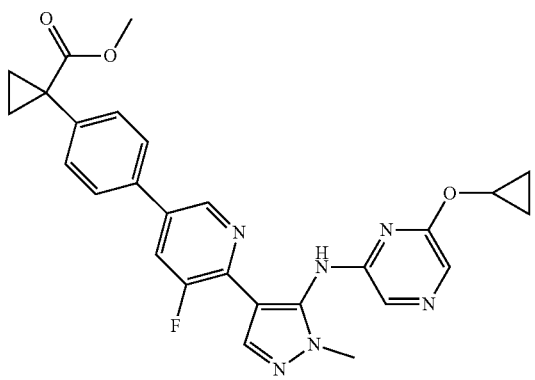 [SMILES: COC(=O)C1(c2ccc(-c3cnc(-c4cnn(C)c4Nc4cncc(OC5CC5)n4)c(F)c3)cc2)CC1]

Add Pd$_2$(dba)$_3$ (0.107 g, 0.117 mmol) and 4,5-bis(diphenylphosphino)-9,9-dimethylxanthene (0.0675 g, 0.117 mmol) to a solution of methyl 1-[4-[6-(5-amino-1-methyl-pyrazol-4-yl)-5-fluoro-3-pyridyl]phenyl]cyclopropanecarboxylate (300 mg, 0.778 mmol), 2-chloro-6-(cyclopropoxy)pyrazine (0.168 g, 0.933 mmol) and cesium carbonate (0.760 g, 2.33 mmol) in 1,4-dioxane (3 mL), then the reaction mixture is stirred at 90° C. for 1 h under nitrogen. The reaction mixture is concentrated and purified by column chromatography on silica gel eluting with PE:EtOAc (1:2) to afford title compound (320 mg, 87% mass, 71.5%) as a yellow solid. LCMS (m/z): 501.2 [M+H]$^+$.

EXAMPLE 3B

1-[4-[6-[5-[[6-(cyclopropoxy)pyrazin-2-yl]amino]-1-methyl-pyrazol-4-yl]-5-fluoro-3-pyridyl]phenyl]cyclopropanecarboxylic acid; hydrochloride

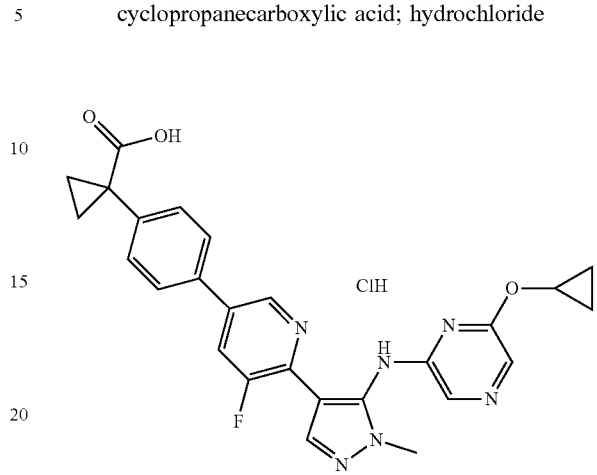

Add lithium hydroxide hydrate (0.0461 g, 1.04 mmol) to a solution of methyl 1-[4-[6-[5-[[6-(cyclopropoxy)pyrazin-2-yl]amino]-1-methyl-pyrazol-4-yl]-5-fluoro-3-pyridyl]phenyl]cyclopropanecarboxylate (300 mg, 0.521 mmol, 87 mass %) in methanol (1 mL) and water (1 mL), and the mixture is stirred at 60° C. for 1 h. then the reaction mixture is acidified by 1N HCl to pH=6 and removed the solvent. The crude product is purified by prep-HPLC [column: YMC-ActusTriart C18 150×30 mm×5 μm, condition: 55-85% B (A: water/0.05% HCl, B: CH3CN), flow rate: 25 mL/min] and lyophilized to afford title compound (153.0 mg, 55.3%) as a yellow solid. LCMS (m/z): 487.1 [M+H]$^+$.
$^1$H NMR (400 MHz, CD$_3$OD) δ=8.65 (s, 1H), 8.00 (d, J=2.0 Hz, 1H), 7.95 (br d, J=12.0 Hz, 1H), 7.83 (s, 1H), 7.63 (d, J=8.0 Hz, 2H), 7.60 (s, 1H), 7.49 (d, J=8.0 Hz, 2H), 3.99-3.92 (m, 1H), 3.86 (s, 3H), 1.64-1.58 (m, 2H), 1.25-1.20 (m, 2H), 0.70-0.58 (m, 4H).

EXAMPLE 4A

Methyl 1-[4-[5-fluoro-6-[5-[[6-(1-fluoro-1-methyl-ethyl)pyrazin-2-yl]amino]-1-methyl-pyrazol-4-yl]-3-pyridyl]phenyl]cyclopropanecarboxylate

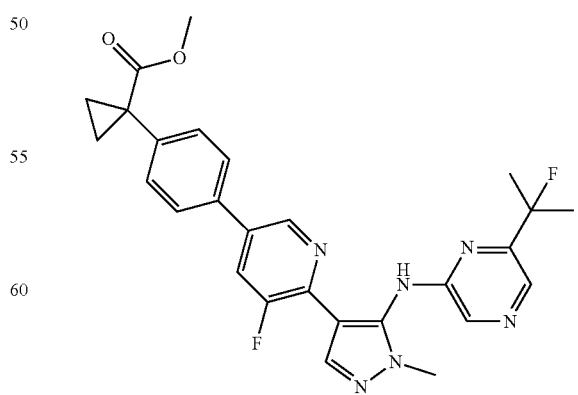

Add cesium carbonate (1.18 g, 3.63 mmol) and Pd$_2$(dba)$_3$ (85.7 mg, 0.0907 mmol) to methyl 1-[4-[6-(5-amino-1- methyl-pyrazol-4-yl)-5-fluoro-3-pyridyl]phenyl]cyclopropanecarboxylate (350 mg, 0.907 mmol) (prepared according to Example 3A), 2-chloro-6-(1-fluoro-1-methyl-ethyl)pyrazine (220 mg, 1.13 mmol, 90 mass %) and 4,5-bis(diphenylphosphino)-9,9-dimethylxanthene (81.0 mg, 0.136 mmol) in 1,4-dioxane (5 mL) under N$_2$. The mixture is stirred at 100° C. for 12 hours. The reaction is quenched with water (20 mL) and extracted with EtOAc (20 mL×3). The combined organic layers are washed with brine (30 mL), dried over anhydrous sodium sulfate and concentrated to afford crude product. The residue is purified by column chromatography eluting with 0-80% EtOAc in PE to afford title product (350 mg, 60 mass %, 45.9%) as brown oil. LCMS (m/z): 505.1 [M+H]$^+$.

EXAMPLE 4B

1-[4-[5-fluoro-6-[5-[[6-(1-fluoro-1-methyl-ethyl)pyrazin-2-yl]amino]-1-methyl-pyrazol-4-yl]-3-pyridyl]phenyl]cyclopropanecarboxylic acid hydrochloride

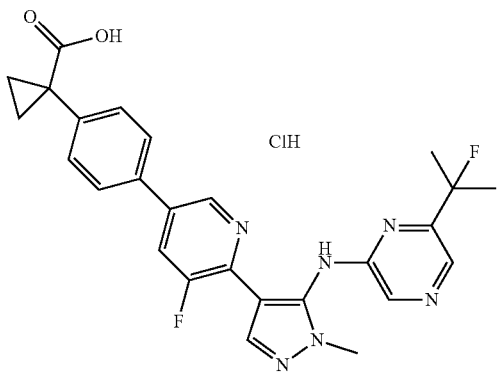 [SMILES: Cn1ncc(-c2ncc(-c3ccc(C4(C(=O)O)CC4)cc3)cc2F)c1Nc1cncc(C(C)(C)F)n1 ; Cl]

Add lithium hydroxide hydrate (53.5 mg, 1.25 mmol) to methyl 1-[4-[5-fluoro-6-[5-[[6-(1-fluoro-1-methyl-ethyl)pyrazin-2-yl]amino]-1-methyl-pyrazol-4-yl]-3-pyridyl]phenyl]cyclopropanecarboxylate (350 mg, 0.416 mmol, 60 mass %) in tetrahydrofuran (5 mL) and water (0.5 mL). The reaction is stirred at 50° C. for 14 hours. The mixture is adjusted to pH=5-6 with 1 N HCl, extracted with EtOAc (40 mL×3). The combined organic layers are washed with brine (30 mL), dried over Na$_2$SO$_4$, filtered and concentrated. The crude product is purified by prep-HPLC [Column YMC-Actus Triart C18 100×30 mm×5 m Condition: water (0.05% HCl)-ACN Begin B 50 End B 80 Gradient Time (min) 9.5 100% B Hold Time (min) 2.5 FlowRate (ml/min) 25] to afford the title product (116 mg, 51.6%) as a yellow solid. LCMS (m/z): 491.1 [M+H]$^+$.

$^1$H NMR (400 MHz, MeOD): δ=8.71 (d, J=1.6 Hz, 1H), 8.25 (s, 1H), 8.20 (dd, J=11.6, 2.0 Hz, 1H), 8.14 (s, 1H), 8.07 (d, J=2.0 Hz, 1H), 7.67 (d, J=8.4 Hz, 2H), 7.53 (d, J=8.4 Hz, 2H), 3.89 (s, 3H), 1.68-1.61 (m, 2H), 1.44 (d, J=22.0 Hz, 6H), 1.29-1.22 (m, 2H).

EXAMPLE 5A

Methyl 1-[4-[6-[5-[[6-(3,3-difluorocyclobutoxy)pyrazin-2-yl]amino]-1-methyl-pyrazol-4-yl]-3-pyridyl]phenyl]cyclopropanecarboxylate

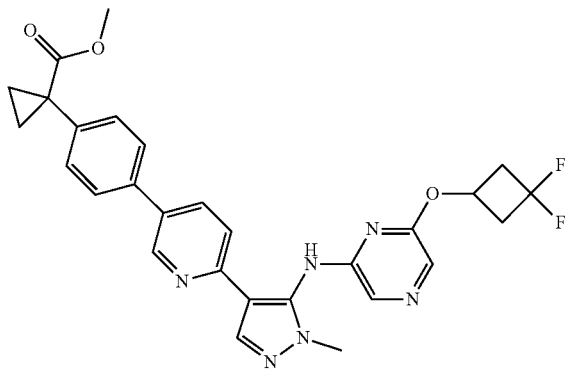 [SMILES: COC(=O)C1(c2ccc(-c3ccc(-c4cnn(C)c4Nc4cncc(OC5CC(F)(F)C5)n4)nc3)cc2)CC1]

Add tris(dibenzylideneacetone)dipalladium (116 mg, 0.123 mmol), 4,5-bis(diphenylphosphino)-9,9-dimethylxanthene (110 mg, 0.185 mmol)) and cesium carbonate (1.21 g, 3.7 mmol) to a solution of methyl 1-[4-[6-(5-amino-1-methyl-pyrazol-4-yl)-3-pyridyl]phenyl]cyclopropanecarboxylate (530 mg, 1.52 mmol) (prepared according to Example 1A) and 2-chloro-6-(cyclobutoxy)pyrazine (250 mg, 1.36 mmol) in O$_2$-free 1,4-dioxane (4 mL) at 25° C. The mixture is stirred at 100° C. for 6 hr. The mixture is filtered through a pad of silica gel (200-300 mush) and the filtrate is concentrated. The residue is purified by flash chromatograph eluting with petroleum ether:EtOAc (1:1) to afford the title compound (260 mg, 41%). LCMS (m/z): 497.3 [M+H]$^+$.

EXAMPLE 5B

1-[4-[6-[5-[[6-(3,3-difluorocyclobutoxy)pyrazin-2-yl]amino]-1-methyl-pyrazol-4-yl]-3-pyridyl]phenyl]cyclopropanecarboxylic acid

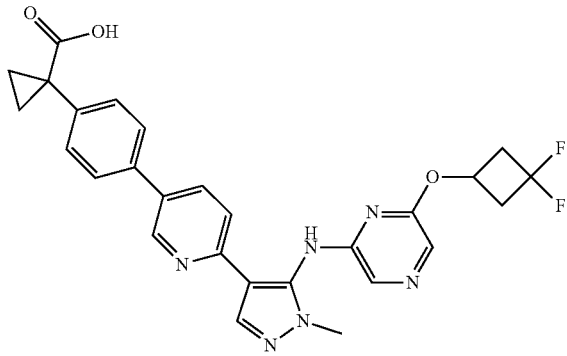 [SMILES: Cn1ncc(-c2ccc(-c3ccc(C4(C(=O)O)CC4)cc3)cn2)c1Nc1cncc(OC2CC(F)(F)C2)n1]

Add lithium hydroxide monohydrate (200 mg, 8.1 mmol) to a solution of methyl 1-[4-[6-[5-[[6-(3,3-difluorocyclobutoxy)pyrazin-2-yl]amino]-1-methyl-pyrazol-4-yl]-3-pyridyl]phenyl]cyclopropanecarboxylate (260 mg, 0.51 mmol) in MeOH (3 mL) and water (3 mL). The resulting mixture is stirred for 12 hours 25° C. The mixture is concentrated and diluted with water (5 mL). The mixture is acidified with HCl (1M) to pH=4-6 and extracted with DCM (5 mL×5). The combined organic phases are washed with brine (10 mL), concentrated, and purified by prep-HPLC [Column SunFire C18, 5 μm, 30×100 mm Condition: water (0.1% FA)-ACN Begin B 29 End B 44 Gradient Time (min) 10 100% B Hold Time (min) 8.5 FlowRate (ml/min) 30] to afford the title compound (50 mg, 23%) as yellow solid. LCMS (m/z): 483.3 [M+H]$^+$.

$^1$H NMR (500 MHz, DMSO-d6)=9.41 (s, 1H), 8.79 (m, 1H), 8.80 (s, 1H), 8.10 (s, 1H), 7.99 (m, 1H), 7.86 (s, 1H), 7.63-7.58 (m, 4H), 7.43 (m, 2H), 4.61 (m, 1H) 3.69 (s, 3H), 2.79 (m, 2H), 2.57 (m, 2H). 1.45 (m, 2H), 1.14 (m, 2H).

EXAMPLE 6A

Methyl 1-[4-[6-[5-[[6-(1-methoxy-1-methyl-ethyl) pyrazin-2-yl]amino]-1-methyl-pyrazol-4-yl]-3-pyridyl]phenyl]cyclopropanecarboxylate

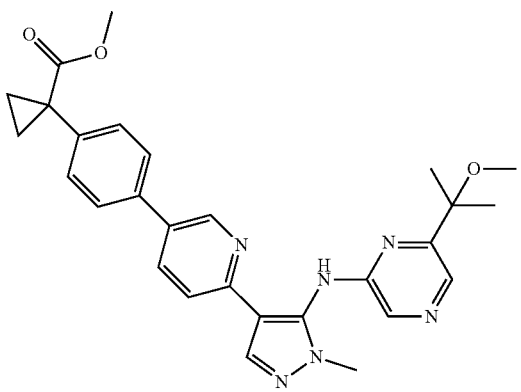 [SMILES: COC(=O)C1(c2ccc(-c3ccc(-c4cnn(C)c4Nc4cncc(C(C)(C)OC)n4)nc3)cc2)CC1]

Add tris(dibenzylideneacetone)dipalladium (0.0384 g, 0.0407 mmol), 4,5-bis(diphenylphosphino)-9,9-dimethyl-xanthene (0.0364 g, 0.0611 mmol) and cesium carbonate (0.398 g, 1.22 mmol) to a solution of methyl 1-[4-[6-(5-amino-1-methyl-pyrazol-4-yl)-3-pyridyl]phenyl]cyclopropanecarboxylate (0.142 g, 0.387 mmol), 2-chloro-6-(1-methoxy-1-methyl-ethyl)pyrazine (80.0 mg, 0.407 mmol) in 1,4-dioxane (4 mL) under N$_2$. The mixture is stirred at 100° C. for 4 hours. The reaction is quenched with water (20 mL) and extracted with EtOAc (20 mL×3). The combined organic layers are washed with brine (30 mL), dried over anhydrous sodium sulfate and concentrated to afford crude. The residue is purified by flash chromatography eluting with petroleum ether/EtOAc (1:5) to afford title compound (90 mg, 44.3%) as brown oil. LCMS (m/z): 521.1[M+Na]$^+$.

EXAMPLE 6B

1-[4-[6-[5-[[6-(1-methoxy-1-methyl-ethyl)pyrazin-2-yl]amino]-1-methyl-pyrazol-4-yl]-3-pyridyl]phenyl] cyclopropanecarboxylic acid; hydrochloride

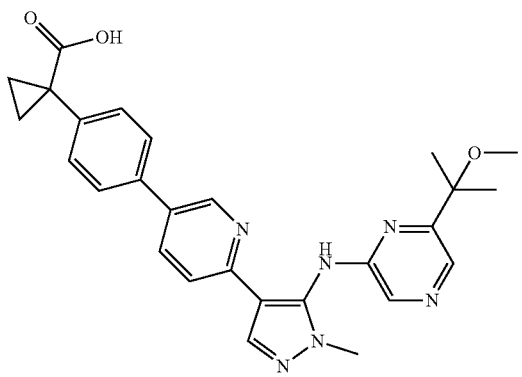 [SMILES: COC(C)(C)c1cncc(Nc2c(-c3ccc(-c4ccc(C5(C(=O)O)CC5)cc4)cn3)cnn2C)n1]

Add lithium hydroxide (11.4 mg, 0.271 mmol) to a solution of methyl 1-[4-[6-[5-[[6-(1-methoxy-1-methyl-ethyl)pyrazin-2-yl]amino]-1-methyl-pyrazol-4-yl]-3-pyridyl]phenyl]cyclopropanecarboxylate (90 mg, 0.181 mmol) in tetrahydrofuran (4 mL) and water (4 mL) at room temperature. The mixture is stirred at 60° C. for 2 hours. The mixture is extracted with EtOAc (10 mL×3) and the aqueous is adjusted to pH=5-7 with HCl (1M). The mixture is extracted with EtOAc (30 mL×3). The combined organic layers are washed with brine (30 mL), dried over anhydrous Na$_2$SO$_4$, filtered and evaporated to afford the crude. It is purified by pre-HPLC [Column Boston Green ODS 150*30, 5 μm, Condition water (0.05% HCl)-ACN Begin B 35 End B 65 Gradient Time (min) 3 100% B Hold Time (min) 1.66 FlowRate (ml/min) 25] to afford title compound (44.1 mg, 45.3%) as a yellow solid. LCMS (m/z): 485.2 [M+H]$^+$.

$^1$H NMR (DMSO-d6, 400 MHz) δ=9.99 (s, 1H), 8.85 (s, 1H), 8.43 (d, J=7.2 Hz, 1H), 8.27 (d, J=4.4 Hz, 2H), 8.09 (s, 1H), 7.81 (d, J=8.4 Hz, 1H), 7.68 (d, J=8.4 Hz, 2H), 7.46 (d, J=8.0 Hz, 2H), 3.78 (s, 3H), 2.92 (s, 3H), 1.52-1.45 (m, 2H), 1.22-1.09 (m, 2H), 1.09 (s, 6H).

EXAMPLE 7A

Ethyl 1-[4-[6-[5-[(6-isopropoxypyrazin-2-yl)amino]-1-methyl-pyrazol-4-yl]-3-pyridyl]-2-methyl-phenyl] cyclopropanecarboxylate 1. Synthesis of ethyl 2-(4-bromo-2-methyl-phenyl)acetate

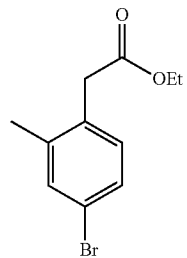

Add sulfuric acid (3.68 g, 2 mL) to a mixture of 2-(4-bromo-2-methyl-phenyl)acetic acid (2.00 g, 8.73 mmol) in ethanol (20 mL), then the reaction mixture is stirred at 80° C. for 2 h. The reaction mixture is cooled to 20° C. and poured into water (100 mL). The resulting mixture is neutralized by sat. Na$_2$CO$_3$ to pH=8. The mixture is extracted with EtOAc (30 mL×3). The combined organic phases are washed with water (20 mL) and brine (20 mL), dried over anhydrous sodium sulfate, concentrated to afford title compound (2.30 g, 97.3%) as a yellow oil.

$^1$H NMR (400 MHz, CHLOROFORM-d) δ=7.34 (s, 1H), 7.29 (dd, J=2.0, 8.4 Hz, 1H), 7.07 (d, J=8.4 Hz, 1H), 4.16 (q, J=7.2 Hz, 2H), 3.58 (s, 2H), 2.30 (s, 3H), 1.25 (t, J=7.2 Hz, 3H)

2. Synthesis of ethyl 1-(4-bromo-2-methyl-phenyl)cyclopropanecarboxylate

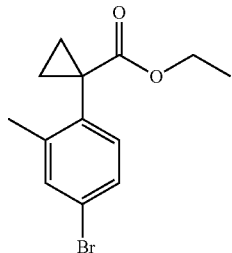 [SMILES: CCOC(=O)C1(c2ccc(Br)cc2C)CC1]

Add sodium hydride (60 mass %) in oil (0.296 g, 7.39 mmol, 60 mass %) to a mixture of ethyl 2-(4-bromo-2-methyl-phenyl)acetate (1.00 g, 3.69 mmol) in DMF (5 mL). The mixture is stirred at 20° C. for 0.5 h, then 1,2-dibromoethane (0.764 g, 4.06 mmol) is added and stirred at 20° C. for 2 h. The reaction mixture is quenched with sat. NH$_4$Cl (10 mL). The result mixture is extracted with EtOAc (10 mL×3). The combined organic phases are washed with water (20 mL), dried over anhydrous sodium sulfate, filtered and concentrated, then purified by column chromatography on silica gel eluting with PE:EtOAc (10:1) to afford title compound (100 mg, 9.08%) as a colorless oil.

$^1$H NMR (400 MHz, CDCl$_3$) δ=7.32 (d, J=1.6 Hz, 1H), 7.27 (dd, J=1.6, 8.4 Hz, 1H), 7.10 (d, J=8.4 Hz, 1H), 4.10 (q, J=7.2 Hz, 2H), 2.30 (s, 3H), 1.70-1.65 (m, 2H), 1.16 (t, J=7.2 Hz, 3H), 1.14-1.09 (m, 2H)

3. Synthesis of ethyl 1-[4-[6-[5-[(6-isopropoxy-pyrazin-2-yl)amino]-1-methyl-pyrazol-4-yl]-3-pyridyl]-2-methyl-phenyl]cyclopropanecarboxylate

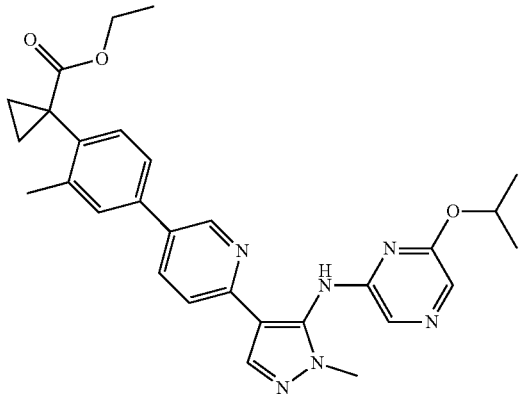 [SMILES: CCOC(=O)C1(c2ccc(-c3ccc(-c4cnn(C)c4Nc4cncc(OC(C)C)n4)nc3)cc2C)CC1]

Add Pd(dppf)Cl$_2$ (0.0225 g, 0.0302 mmol) and potassium acetate (0.0916 g, 0.906 mmol) to a solution of ethyl 1-(4-bromo-2-methyl-phenyl)cyclopropanecarboxylate (90.0 mg, 0.302 mmol), bis(pinacolato)diboron (0.0861 g, 0.332 mmol) in 1,4-dioxane (0.5 mL), then the reaction mixture is stirred at 90° C. for 1 h under nitrogen. N-[4-(5-bromo-2-pyridyl)-2-methyl-pyrazol-3-yl]-6-isopropoxy-pyrazin-2-amine (0.136 g, 0.332 mmol), sodium carbonate (0.0960 g, 0.906 mmol) and water (0.1 mL) is added to above solution and stirred at 90° C. for 1 h under nitrogen. The reaction mixture is concentrated to afford a black residue, which is purified by column chromatography on silica gel eluting with PE:EtOAc (1:1) to afford title compound (90 mg, 58.0%) as a yellow oil. LCMS (m/z): 513.2 [M+H]$^+$.

EXAMPLE 7B

1-[4-[6-[5-[(6-isopropoxypyrazin-2-yl)amino]-1-methyl-pyrazol-4-yl]-3-pyridyl]-2-methyl-phenyl]cyclopropanecarboxylic acid; hydrochloride

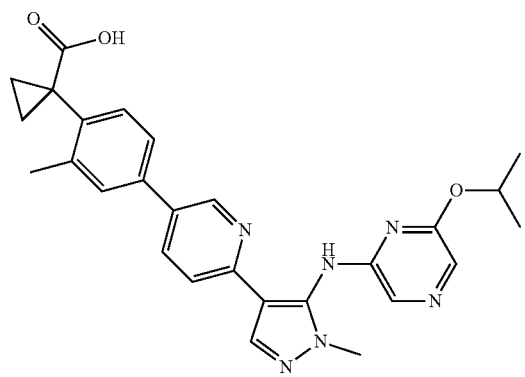 [SMILES: Cc1cc(-c2ccc(-c3cnn(C)c3Nc3cncc(OC(C)C)n3)nc2)ccc1C1(C(=O)O)CC1]

Add lithium hydroxide hydrate (0.0137 g, 0.323 mmol) to a mixture of ethyl 1-[4-[6-[5-[(6-isopropoxypyrazin-2-yl)amino]-1-methyl-pyrazol-4-yl]-3-pyridyl]-2-methyl-phenyl]cyclopropanecarboxylate (90 mg, 0.162 mmol) in methanol (1 mL) and water (1 mL), then the reaction mixture is stirred at 60° C. for 2 h. The reaction mixture is acidified by 1 N HCl to pH=6 and extracted with EtOAc (30 mL×3), dried over anhydrous sodium sulfate, filtered and concentrated. The crude product is purified by prep-HPLC [column: YMC-ActusTriart C18 150×30 mm×5 μm, condition: 30-60% B (A: water/0.05% HCl, B: CH3CN), flow rate: 25 mL/min] and lyophilized to afford title compound (17.9 mg, 20.5%) as a yellow solid. LCMS (m/z): 485.2 [M+H]$^+$.

$^1$H NMR (400 MHz, CD$_3$OD) δ=8.90 (d, J=2.0 Hz, 1H), 8.71 (dd, J=2.0, 8.8 Hz, 1H), 8.27 (s, 1H), 8.11 (d, J=8.8 Hz, 1H), 7.81 (br s, 1H), 7.62-7.57 (m, 2H), 7.54 (dd, J=2.0, 8.0 Hz, 1H), 7.44 (d, J=8.0 Hz, 1H), 4.78-4.67 (m, 1H), 3.87 (s, 3H), 2.46 (s, 3H), 1.74-1.66 (m, 2H), 1.25-1.17 (m, 2H), 1.12 (d, J=6.4 Hz, 6H).

EXAMPLE 8A

Ethyl 1-[4-[6-[5-[[6-(cyclopropoxy)pyrazin-2-yl]amino]-1-methyl-pyrazol-4-yl]-3-pyridyl]-2-(trifluoromethyl)phenyl]cyclopropanecarboxylate 1. Synthesis of 2-[4-bromo-2-(trifluoromethyl)phenyl]acetic acid

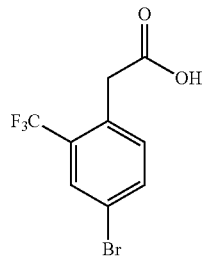 [SMILES: O=C(O)Cc1ccc(Br)cc1C(F)(F)F]

Add hydrochloric acid (2 mL, 12 M) to a solution of 2-[4-bromo-2-(trifluoromethyl)phenyl]acetonitrile (600 mg, 2.25 mmol) in acetic acid (2 mL), the mixture is stirred at 100° C. for 2 h under nitrogen. The reaction mixture is concentrated to afford title compound (600 mg, 89.5%) as colorless oil.

$^1$H NMR (400 MHz, CDCl$_3$) δ=7.82 (d, J=1.6 Hz, 1H), 7.67 (dd, J=1.6, 8.4 Hz, 1H), 7.29 (s, 1H), 3.83 (s, 2H).

2. Synthesis of ethyl 2-[4-bromo-2-(trifluoromethyl)phenyl]acetate

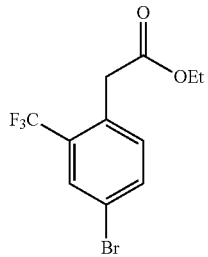

Add sulfuric acid (3.68 g, 2 mL) to a solution of 2-[4-bromo-2-(trifluoromethyl)phenyl]acetic acid (600 mg, 2.0 mmol) in ethanol (10 mL), the mixture is stirred at 80° C. for 3 h under nitrogen. The reaction mixture is diluted with water (20 mL) and extracted with EtOAc (20 mL×2). The combined organic layers are washed with sat. NaHCO$_3$ (20 mL), brine (20 mL×2), dried over sodium sulfate and concentrated to afford title compound (600 mg, 91.0%) as colorless oil.

$^1$H NMR (400 MHz, CDCl$_3$) δ=7.80 (d, J=1.6 Hz, 1H), 7.66 (dd, J=1.6, 8.0 Hz, 1H), 7.28 (d, J=9.2 Hz, 1H), 4.17 (q, J=7.2 Hz, 2H), 3.77 (s, 2H), 1.25 (t, J=7.2 Hz, 3H).

3. Synthesis of ethyl 1-[4-bromo-2-(trifluoromethyl)phenyl]cyclopropane carboxylate

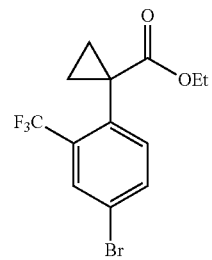 [SMILES: CCOC(=O)C1(c2ccc(Br)cc2C(F)(F)F)CC1]

Add sodium hydride in paraffin oil (0.148 g, 3.69 mmol, 60 mass %) to a solution of ethyl 2-[4-bromo-2-(trifluoromethyl)phenyl]acetate (550 mg, 1.68 mmol) in DMF (5 mL), then the mixture is heated to 50° C. for 1 hour. 1,2-dibromoethane (0.335 g, 1.76 mmol) is added and the reaction is stirred at 50° C. for 2 hours. The reaction is quenched with saturated NH$_4$Cl solution (30 mL) and extracted with EtOAc (30 mL×3). The combined organic layers are washed with brine (30 mL), dried over anhydrous sodium sulfate, filtered and concentrated. The residue is purified by flash chromatography eluting with petroleum ether/EtOAc (20:1) to afford the crude. The crude is purified by pre-HPLC [column: Boston Green ODS 150×30, 5 μm. condition: 35-65% B (A:water (0.05% HCl), B:ACN), flow rate: 25 mL/min] to afford title compound (0.150 g, 25.2%) as colorless oil. LCMS (m/z): 336.9/338.8 [M+H, Br$^{79}$/Br$^{81}$]$^+$.

$^1$H NMR (400 MHz, CDCl$_3$) δ=7.78 (d, J=2.0 Hz, 1H), 7.63 (dd, J=1.6, 8.4 Hz, 1H), 7.34 (d, J=8.4 Hz, 1H), 4.13-3.96 (m, 2H), 1.65-1.58 (m, 2H), 1.33-1.19 (m, 2H), 1.12 (t, J=7.2 Hz, 3H).

4. Synthesis of ethyl 1-[4-[6-(5-amino-1-methyl-pyrazol-4-yl)-3-pyridyl]-2-(trifluoromethyl)phenyl]cyclopropanecarboxylate

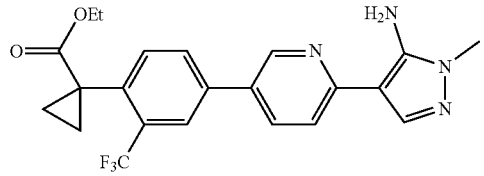 [SMILES: CCOC(=O)C1(c2ccc(-c3ccc(-c4cnn(C)c4N)nc3)cc2C(F)(F)F)CC1]

Add Pd(dppf)Cl$_2$ (0.0316 g, 0.0423 mmol) and potassium acetate (0.128 g, 1.27 mmol) to a solution of ethyl 1-[4-bromo-2-(trifluoromethyl)phenyl]cyclopropanecarboxylate (150 mg, 0.423 mmol), bis(pinacolato)diboron (0.120 g, 0.465 mmol) in 1,4-dioxane (4 mL), then the reaction mixture is stirred at 90° C. for 1 h under nitrogen. Then 4-(5-bromo-2-pyridyl)-2-methyl-pyrazol-3-amine (0.124 g, 0.465 mmol), sodium carbonate (0.134 g, 1.27 mmol) and water (1 mL) is added to above solution and stirred at 90° C. for 1 h under nitrogen. The reaction mixture is concentrated to afford a black residue, which is purified by column chromatography on silica gel eluting with PE:EtOAc (1:1) to afford title compound (140 mg, 77.6%) as a yellow oil. LCMS (m/z): 431.1 [M+H]$^+$.

5. Synthesis of ethyl 1-[4-[6-[5-[[6-(cyclopropoxy)pyrazin-2-yl]amino]-1-methyl-pyrazol-4-yl]-3-pyridyl]-2-(trifluoromethyl)phenyl]cyclopropanecarboxylate

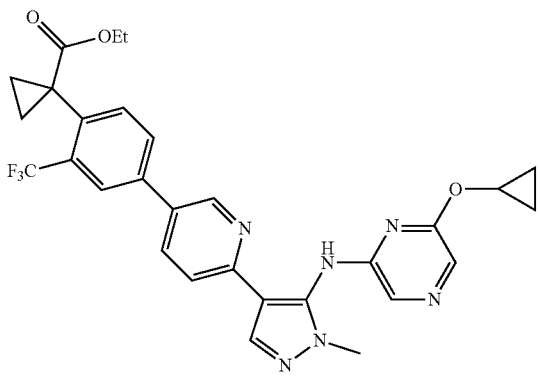 [SMILES: CCOC(=O)C1(c2ccc(-c3ccc(-c4cnn(C)c4Nc4cncc(OC5CC5)n4)nc3)cc2C(F)(F)F)CC1]

Add tris(dibenzylideneacetone)dipalladium (0.0300 g, 0.0328 mmol), 4,5-bis(diphenylphosphino)-9,9-dimethylxanthene (0.0190 g, 0.0328 mmol) and cesium carbonate (0.320 g, 0.984 mmol) to a mixture of ethyl 1-[4-[6-(5-amino-1-methyl-pyrazol-4-yl)-3-pyridyl]-2-(trifluoromethyl)phenyl]cyclopropanecarboxylate (140 mg, 0.328 mmol), 2-chloro-6-(cyclopropoxy)pyrazine (0.0706 g, 0.393 mmol) in 1,4-dioxane (5 mL), then the reaction mixture is stirred at 95° C. for 2 h under nitrogen. The reaction mixture is concentrated and purified by column chromatography on silica gel eluting with PE:EtOAc (4:1) to afford title compound (133 mg, 72.0%) as a yellow solid. LCMS (m/z): 565.1 [M+H]$^+$.

EXAMPLE 8B

1-[4-[6-[5-[[6-(cyclopropoxy)pyrazin-2-yl]amino]-1-methyl-pyrazol-4-yl]-3-pyridyl]-2-(trifluoromethyl)phenyl]cyclopropanecarboxylic acid; hydrochloride

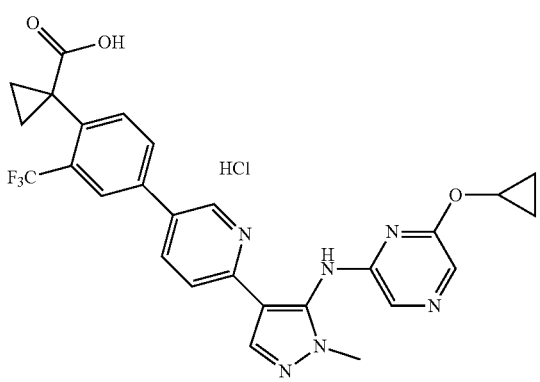 [SMILES: Cn1ncc(-c2ccc(-c3ccc(C4(C(=O)O)CC4)c(C(F)(F)F)c3)cn2)c1Nc1cncc(OC2CC2)n1 ; Cl]

Add lithium hydroxide hydrate (0.0187 g, 0.446 mmol) to a mixture of ethyl 1-[4-[6-[5-[[6-(cyclopropoxy)pyrazin-2-yl]amino]-1-methyl-pyrazol-4-yl]-3-pyridyl]-2-(trifluoromethyl)phenyl]cyclopropanecarboxylate (133 mg, 0.223 mmol) in methanol (2 mL) and water (2 mL), then the reaction mixture is stirred at 60° C. for 1 h. The reaction mixture is acidified by 1N HCl to pH=6, then purified by prep-HPLC [column: YMC-Actus Triart C18 150*30 mm*5 μm, condition: 40-70% B (A: water/0.05% HCl, B: CH3CN), flow rate: 25 mL/min] and lyophilized to afford title compound (34.4 mg, 25.3%) as a white solid. LCMS (m/z): 537.0 [M+H]$^+$.

$^1$H NMR (400 MHz, CD$_3$OD) δ=9.01 (d, J=2.0 Hz, 1H), 8.76 (dd, J=2.4, 8.8 Hz, 1H), 8.27 (s, 1H), 8.15 (d, J=8.4 Hz, 1H), 8.09 (s, 1H), 8.00 (dd, J=1.6, 8.0 Hz, 1H), 7.92 (s, 1H), 7.77 (d, J=8.0 Hz, 1H), 7.70 (s, 1H), 3.91-3.84 (m, 4H), 1.97-1.54 (m, 2H), 1.54-1.08 (m, 2H), 0.65-0.55 (m, 4H)

EXAMPLE 9A

Ethyl 1-[2-cyano-4-[6-[5-[[6-(cyclopropoxy)pyrazin-2-yl]amino]-1-methyl-pyrazol-4-yl]-3-pyridyl]phenyl]cyclopropanecarboxylate 1. Synthesis of 2-(4-bromo-2-cyano-phenyl)acetate

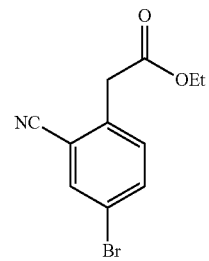 [SMILES: CCOC(=O)Cc1ccc(Br)cc1C#N]

Add chlorotrimethylsilane (0.233 g, 2.10 mmol) to a mixture of zinc (2.55 g, 39.0 mmol) in tetrahydrofuran (20 mL) at 15° C. The mixture is stirred for 15 min and then a solution of ethyl bromoacetate (5.11 g, 30.0 mmol) in tetrahydrofuran (10 mL) is added dropwise. The reaction is heated to 40° C. for 30 min. The mixture is cooled to 20° C. and the supernatant liquid is used as title compound bromo-(2-ethoxy-2-oxo-ethyl)zinc (30 mmol, 1 mol/L, 100%) in the next step directly. Add bromo-(2-ethoxy-2-oxo-ethyl)zinc (15.4 mL, 15.4 mmol, 1 mol/L) to a mixture of 5-bromo-2-iodo-benzonitrile (4.00 g, 12.9 mmol), bis(dibenzylideneacetone)palladium (0.187 g, 0.322 mmol,) and 4,5-bis(diphenylphosphino)-9,9-dimethylxanthene (0.188 g, 0.322 mmol) in tetrahydrofuran (10 mL) under nitrogen. The reaction is heated to 65° C. for 12 hours. The reaction is quenched with saturated NH$_4$Cl solution (30 mL) and extracted with EtOAc (30 mL×3). The combined organic layers are washed with brine (30 mL), dried over anhydrous sodium sulfate, filtered and concentrated. The residue is purified by flash chromatography eluting with petroleum ether/EtOAc (10:1) to the title compound (0.520 g, 14.3%) as a light grey solid.

$^1$H NMR (400 MHz, CDCl$_3$) δ=7.80 (d, J=2.0 Hz, 1H), 7.70 (dd, J=2.0, 8.4 Hz, 1H), 7.32 (d, J=8.0 Hz, 1H), 4.21 (q, J=7.2 Hz, 2H), 3.84 (s, 2H), 1.29 (t, J=7.2 Hz, 3H).

2. Synthesis of ethyl 1-(4-bromo-2-cyano-phenyl)cyclopropanecarboxylate

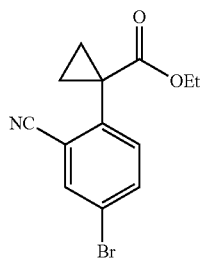

Add sodium hydride in paraffin oil (0.162 g, 4.05 mmol, 60 mass %) to a solution of ethyl 2-(4-bromo-2-cyano-phenyl)acetate (0.520 g, 1.84 mmol) in DMF (10 mL), and the mixture is heated to 50° C. for 1 hour. Then 1,2-dibromoethane (0.367 g, 1.93 mmol) is added and the reaction is stirred at 50° C. for 3 hours. The reaction is quenched with saturated NH₄Cl solution (30 mL) and extracted with EtOAc (30 mL×3). The combined organic layers are washed with brine (30 mL), dried over anhydrous sodium sulfate, filtered and concentrated. The residue is purified by flash chromatography eluting with petroleum ether/EtOAc (20:1) to afford title compound (0.370 g, 64.9%) as a grey solid.

$^1$H NMR (400 MHz, CDCl₃) δ=7.79 (d, J=2.0 Hz, 1H), 7.67 (dd, J=2.0, 8.4 Hz, 1H), 7.28 (d, J=8.4 Hz, 1H), 4.14 (q, J=7.2 Hz, 2H), 1.85-1.79 (m, 2H), 1.29-1.24 (m, 2H), 1.20 (t, J=7.2 Hz, 3H).

3. Synthesis of ethyl 1-[4-[6-(5-amino-1-methyl-pyrazol-4-yl)-3-pyridyl]-2-cyano-phenyl]cyclopropanecarboxylate

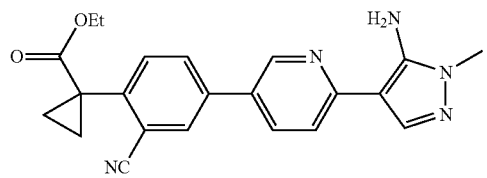 [SMILES: CCOC(=O)C1(c2ccc(-c3ccc(-c4cnn(C)c4N)nc3)cc2C#N)CC1]

Add [1,1'-bis(diphenylphosphino)ferrocene]dichloropalladium(II) (0.0482 g, 0.0646 mmol) to a mixture of ethyl 1-(4-bromo-2-cyano-phenyl)cyclopropanecarboxylate (200 mg, 0.646 mmol), bis(pinacolato)diboron (0.184 g, 0.711 mmol) and potassium acetate (0.196 g, 1.94 mmol) in 1,4-dioxane (4 mL), then the reaction mixture is stirred at 90° C. for 1 h under nitrogen. Then 4-(5-bromo-2-pyridyl)-2-methyl-pyrazol-3-amine (0.189 g, 0.711 mmol), sodium carbonate (0.205 g, 1.94 mmol) and water (1 mL) are added to above solution and stirred at 90° C. for 1 h under nitrogen. The reaction mixture is concentrated to afford a black residue, which is purified by column chromatography on silica gel eluting with PE:EtOAc (1:1) to afford title compound (230 mg, 87.3%) as a yellow solid. LCMS (m/z): 388.1 [M+H]⁺.

$^1$H NMR (400 MHz, CDCl₃) δ=8.68 (d, J=2.4 Hz, 1H), 7.86 (d, J=1.6 Hz, 1H), 7.80 (dd, J=2.4, 8.4 Hz, 1H), 7.76-7.71 (m, 2H), 7.49 (dd, J=1.6, 8.4 Hz, 2H), 5.62 (br s, 2H), 4.17 (q, J=7.2 Hz, 2H), 3.71 (s, 3H), 1.88-1.81 (m, 2H), 1.36-1.30 (m, 2H), 1.22 (t, J=7.2 Hz, 3H).

4. Synthesis of ethyl 1-[2-cyano-4-[6-[5-[[6-(cyclopropoxy)pyrazin-2-yl]amino]-1-methyl-pyrazol-4-yl]-3-pyridyl]phenyl]cyclopropanecarboxylate

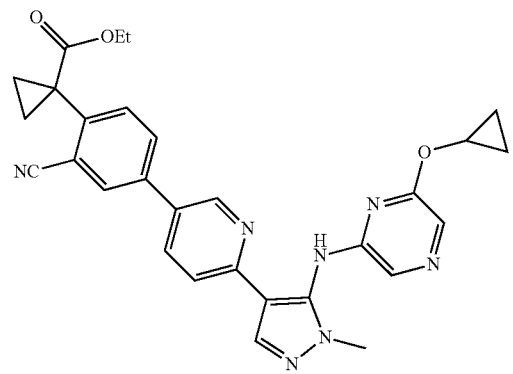 [SMILES: CCOC(=O)C1(c2ccc(-c3ccc(-c4cnn(C)c4Nc4cncc(OC5CC5)n4)nc3)cc2C#N)CC1]

Add tris(dibenzylideneacetone)dipalladium(0) (0.0695 g, 0.0736 mmol) and 4,5-bis(diphenylphosphino)-9,9-dimethylxanthene (0.0434 g, 0.0736 mmol) to a mixture of ethyl 1-[4-[6-(5-amino-1-methyl-pyrazol-4-yl)-3-pyridyl]-2-cyano-phenyl]cyclopropanecarboxylate (200 mg, 0.490 mmol), 2-chloro-6-(cyclopropoxy)pyrazine (0.106 g, 0.589 mmol) and cesium carbonate (0.479 g, 1.47 mmol,) in 1,4-dioxane (5 mL, then the reaction mixture is stirred at 95° C. for 2 h under nitrogen. The reaction mixture is concentrated to afford a black residue, which is purified by column chromatography on silica gel eluting with PE:EtOAc (1:4) to afford title compound (200 mg, 63 mass %, 49.3%) as a yellow solid. LCMS (m/z): 522.1 [M+H]⁺.

EXAMPLE 9B

1-[2-cyano-4-[6-[5-[[6-(cyclopropoxy)pyrazin-2-yl]amino]-1-methyl-pyrazol-4-yl]-3-pyridyl]phenyl]cyclopropanecarboxylic acid; hydrochloride

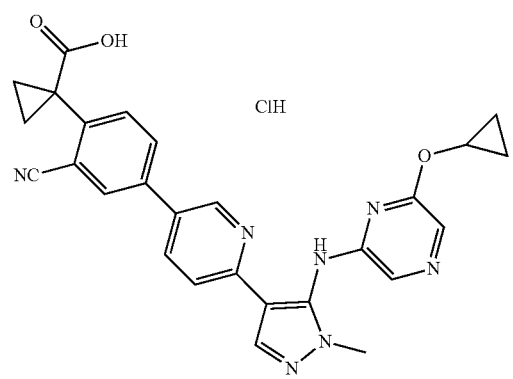 [SMILES: Cn1ncc(-c2ccc(-c3ccc(C4(C(=O)O)CC4)c(C#N)c3)cn2)c1Nc1cncc(OC2CC2)n1 ; Cl]

Add lithium hydroxide hydrate (0.0203 g, 0.483 mmol) to a mixture of ethyl 1-[2-cyano-4-[6-[5-[[6-(cyclopropoxy)pyrazin-2-yl]amino]-1-methyl-pyrazol-4-yl]-3-pyridyl]phenyl]cyclopropanecarboxylate (200 mg, 0.242 mmol, 63 mass %) in methanol (2 mL) and water (2 mL), then the reaction mixture is stirred at 60° C. for 1 h. The reaction mixture is acidified by 1N HCl to pH=6 and is concentrated. Then purified by prep-HPLC [column: YMC-Actus Triart C18 150×30 mm×5 μm, condition: 35-65% B (A: water/0.05% HCl, B: CH₃CN), flow rate: 25 mL/min] and lyophilized to afford title compound (49.6 mg, 92.44 mass %, 35.8%) as a yellow solid. LCMS (m/z): 494.1 [M+H]⁺.

¹H NMR (400 MHz, CDCl₃) δ=9.02 (s, 1H), 8.77 (d, J=7.2 Hz, 1H), 8.28 (s, 1H), 8.22 (s, 1H), 8.18 (d, J=8.4 Hz, 1H), 8.05 (d, J=7.2 Hz, 1H), 7.96 (s, 1H), 7.79-7.67 (m, 2H), 3.99-3.80 (m, 4H), 1.86-1.75 (m, 2H), 1.45-1.34 (m, 2H), 0.71-0.54 (m, 4H).

EXAMPLE 10A

Methyl 1-[4-[6-[5-[[6-(cyclopropoxy)pyrazin-2-yl]amino]-1-methyl-pyrazol-4-yl]-3-pyridyl]phenyl]cyclopropanecarboxylate

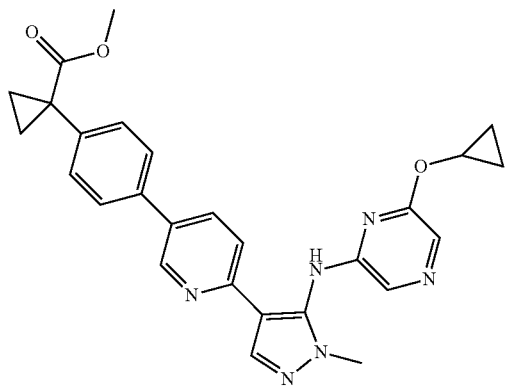 [SMILES: COC(=O)C1(c2ccc(-c3ccc(-c4cnn(C)c4Nc4cncc(OC5CC5)n4)nc3)cc2)CC1]

Add methyl 1-[4-[6-(5-amino-1-methyl-pyrazol-4-yl)-3-pyridyl]phenyl]cyclo propanecarboxylate (530 mg, 1.377 mmol) (prepared according to Example 1A), 2-chloro-6-(cyclopropoxy)pyrazine (300 mg, 1.758 mmol) and cesium carbonate (1.0 g, 3.1 mmol) in O₂-free 1,4-dioxane (10 mL) to tris(dibenzylideneacetone)dipalladium (300 mg, 0.33 mmol) and 4,5-bis(diphenylphosphino)-9,9-dimethylxanthene (280 mg, 0.483 mmol) at 25° C. The mixture is then stirred at 100° C. for 6 hr. The mixture is filtered through a pad of silica gel (200-300 mush) and the filtrate is concentrated. The residue is purified by flash chromatograph eluting with petroleum ether:EtOAc (1:1) to afford the title compound (300 mg, 45.2%) as light yellow oil. LCMS (m/z): 483.2 [M+H]⁺.

EXAMPLE 10B

1-[4-[6-[5-[[6-(cyclopropoxy)pyrazin-2-yl]amino]-1-methyl-pyrazol-4-yl]-3-pyridyl]phenyl]cyclopropanecarboxylic acid

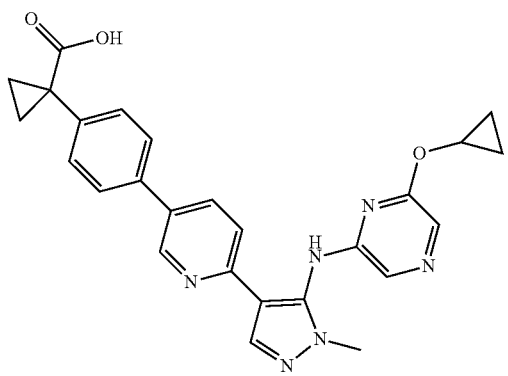 [SMILES: Cn1ncc(-c2ccc(-c3ccc(C4(C(=O)O)CC4)cc3)cn2)c1Nc1cncc(OC2CC2)n1]

Add methyl 1-[4-[6-[5-[[6-(cyclopropoxy)pyrazin-2-yl]amino]-1-methyl-pyrazol-4-yl]-3-pyridyl]phenyl]cyclopropanecarboxylate (300 mg, 0.621 mmol) in THF (4 mL) and water (2 mL) to lithium hydroxide monohydrate (200 mg, 8.1 mmol). The resulting mixture is stirred for 12 hours 25° C. The mixture is concentrated and diluted with water (5 mL). The mixture is acidified with HCl (1M) to pH=4-6. The mixture is extracted with DCM (5 mL×5). The combined organic phases are washed with brine (10 mL), concentrated, purified by prep-HPLC [Column SunFire C18, 5 μm, 30×100 mm Condition: water (0.1% FA)-ACN Begin B 29 End B 44 Gradient Time (min) 10 100% B Hold Time (min) 7.5 FlowRate (ml/min) 30] to afford the title compound (50 mg, 42.1%) as yellow solid. LCMS (m/z): 469.2 [M+H]⁺.

¹H NMR (500 MHz, DMSO-d6) δ 9.41 (s, 1H), 8.80 (d, J=2.0 Hz, 1H), 8.10-7.98 (M, 2H), 7.81 (s, 1H), 7.68 (s, 1H), 7.62-7.60 (m, 3H), 3.94 (m, 1H), 3.70 (s, 3H), 1.45 (m, 2H), 1.13 (m, 2H), 0.60 (d, J=6.0 Hz, 4H).

EXAMPLE 11A

Methyl 1-[4-[5-fluoro-6-[5-[(6-isopropoxypyrazin-2-yl)amino]-1-methyl-pyrazol-4-yl]-3-pyridyl]phenyl]cyclopropanecarboxylate

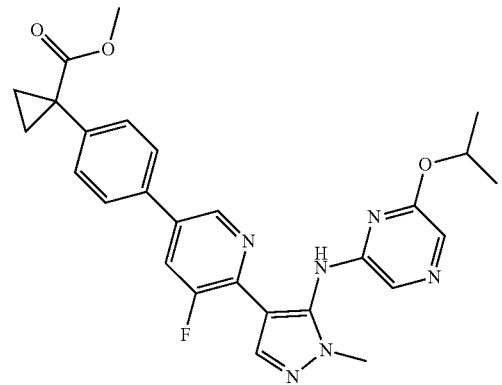 [SMILES: COC(=O)C1(c2ccc(-c3cnc(-c4cnn(C)c4Nc4cncc(OC(C)C)n4)c(F)c3)cc2)CC1]

Add tris(dibenzylideneacetone)dipalladium (0.0712 g, 0.0778 mmol), 4,5-bis(diphenylphosphino)-9,9-dimethyl-xanthene (0.0450 g, 0.0778 mmol) and cesium carbonate (0.507 g, 31.56 mmol) to a solution of methyl 1-[4-[6-(5-amino-1-methyl-pyrazol-4-yl)-5-fluoro-3-pyridyl]phenyl] cyclopropanecarboxylate (200 mg, 0.519 mmol) (prepared according to Example 3A), 2-chloro-6-isopropoxy-pyrazine (0.113 g, 0.622 mmol) in 1,4-dioxane (3 mL), then the reaction mixture is stirred at 90° C. for 1 h under nitrogen. The reaction mixture is concentrated and purified by column chromatography on silica gel eluting with PE:EtOAc (1:2) to afford title compound (130 mg, 49.9%) as a yellow solid. LCMS (m/z): 503.2 [M+H]$^+$.

EXAMPLE 11B

1-[4-[5-fluoro-6-[5-[(6-isopropoxypyrazin-2-yl) amino]-1-methyl-pyrazol-4-yl]-3-pyridyl]phenyl] cyclopropanecarboxylic acid; hydrochloride

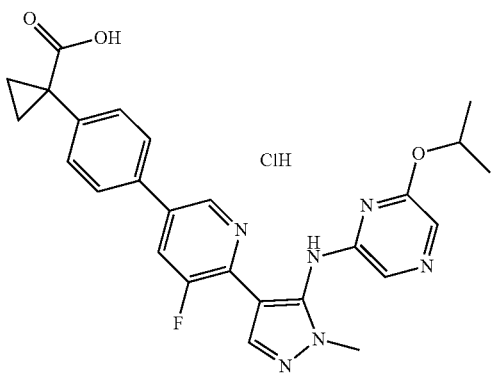 [SMILES: CC(C)Oc1cncc(Nc2c(-c3ncc(-c4ccc(C5(C(=O)O)CC5)cc4)cc3F)cnn2C)n1 ; Cl]

Add hydroxide lithium hydrate (0.0217 g, 0.517 mmol) to a mixture of methyl 1-[4-[5-fluoro-6-[5-[(6-isopropoxy-pyrazin-2-yl)amino]-1-methyl-pyrazol-4-yl]-3-pyridyl]phenyl]cyclopropanecarboxylate (200 mg, 0.259 mmol, 65 mass %) in methanol (1 mL) and water (1 mL) was added, then the reaction mixture is stirred at 60° C. for 1 h. The reaction mixture was acidified by 1N HCl to pH=6. The result mixture is concentrated and purified by prep-HPLC [column: YMC-ActusTriart C18 150×30 mm×5 μm, condition: 48-78% B (A: water/0.05% HCl, B: CH$_3$CN), flow rate: 25 mL/min] and lyophilized to afford title compound (101.6 mg, 99.69 mass %, 74.6%) as a yellow solid. LCMS (m/z): 489.1 [M+H]$^+$.

$^1$H NMR (400 MHz, CDCl$_3$) δ=8.60 (s, 1H), 8.00 (d, J=2.8 Hz, 1H), 7.84 (dd, J=2.0, 12.0 Hz, 1H), 7.69 (s, 1H), 7.60 (d, J=8.4 Hz, 2H), 7.47 (d, J=8.4 Hz, 2H), 7.45 (br s, 1H), 4.86-4.83 (m, 1H), 3.84 (s, 3H), 1.63-1.59 (m, 2H), 1.25-1.20 (m, 2H), 1.16 (d, J=6.4 Hz, 6H)

EXAMPLE 12A

Methyl 1-[4-[6-[5-[[6-(1,1-difluoroethyl)pyrazin-2-yl]amino]-1-methyl-pyrazol-4-yl]-3-pyridyl]phenyl] cyclopropanecarboxylate

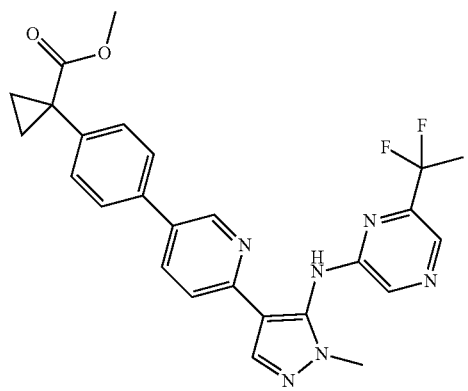 [SMILES: COC(=O)C1(c2ccc(-c3ccc(-c4cnn(C)c4Nc4cncc(C(C)(F)F)n4)nc3)cc2)CC1]

Add to tris(dibenzylideneacetone)dipalladium (0.103 g, 0.109 mmol) and 4,5-bis(diphenylphosphino)-9,9-dimethyl-xanthene (0.0976 g, 0.164 mmol) to methyl 1-[4-[6-(5-amino-1-methyl-pyrazol-4-yl)-3-pyridyl]phenyl]cyclopropanecarboxylate (0.400, 1.09 mmol) (prepared according to Example 1A), 2-chloro-6-(1,1-difluoroethyl)pyrazine (0.325 g, 1.64 mmol, 90 mass %) and cesium carbonate (1.42 g, 4.36 mmol) in 1,4-dioxane (8 mL) under N$_2$. The mixture is stirred at 100° C. for 12 hours. The mixture is diluted with water (40 mL) and extracted with EtOAc (50 mL×3). The combined organic layers are washed with brine (50 mL), dried over anhydrous sodium sulfate, filtered and concentrated. The residue is purified by column chromatography on silica gel EtOAc:PE (1:1) to afford title (361 mg, 68.1%). LCMS (m/z): 491.1 [M+H]$^+$.

EXAMPLE 12B

1-[4-[6-[5-[[6-(1,1-difluoroethyl)pyrazin-2-yl] amino]-1-methyl-pyrazol-4-yl]-3-pyridyl]phenyl] cyclopropanecarboxylic acid; hydrochloride

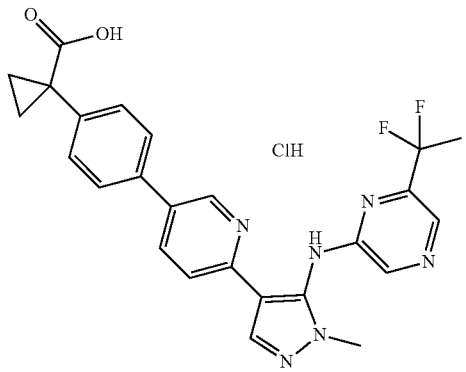 [SMILES: Cn1ncc(-c2ccc(-c3ccc(C4(C(=O)O)CC4)cc3)cn2)c1Nc1cncc(C(C)(F)F)n1 ; Cl]

Add lithium hydroxide hydrate (91.0 mg, 2.12 mmol) to a solution of methyl 1-[4-[6-[5-[[6-(1,1-difluoroethyl)pyrazin-2-yl]amino]-1-methyl-pyrazol-4-yl]-3-pyridyl]phenyl]cyclopropanecarboxylate (360 mg, 0.706 mmol) in tetrahydrofuran (5 mL) and water (0.5 mL). The reaction is stirred at 50° C. for 14 hours. The mixture is adjusted to pH=5-6 with 1 N HCl, extracted with EtOAc (40 mL×3). The combined organic layers are washed with brine (30 mL), dried over Na₂SO₄, filtered and concentrated. The crude product is purified by prep-HPLC [Column YMC-Actus Triart C18 100×30 mm×5 m Condition: water (0.05% HCl)-ACN Begin B 30 End B 60 Gradient Time (min) 9.5 100% B Hold Time (min) 2.5 FlowRate (ml/min) 25] to afford title compound (80.0 mg, 21.0%) as a yellow solid. LCMS (m/z): 477.0 [M+H]⁺.

¹H NMR (400 MHz, DMSO-d6) δ=10.06 (br s, 1H), 8.78 (s, 1H), 8.43 (s, 1H), 8.23-8.16 (m, 3H), 7.73 (d, J=8.4 Hz, 1H), 7.65 (d, J=8.4 Hz, 2H), 7.44 (d, J=8.0 Hz, 2H), 3.75 (s, 3H), 1.65 (t, J=18.8 Hz, 3H), 1.50-1.43 (m, 2H), 1.23-1.15 (m, 2H).

EXAMPLE 13A

Methyl 1-[4-[6-[5-[[6-(1-fluoro-1-methyl-ethyl)pyrazin-2-yl]amino]-1-methyl-pyrazol-4-yl]-3-pyridyl]phenyl]cyclopropanecarboxylate

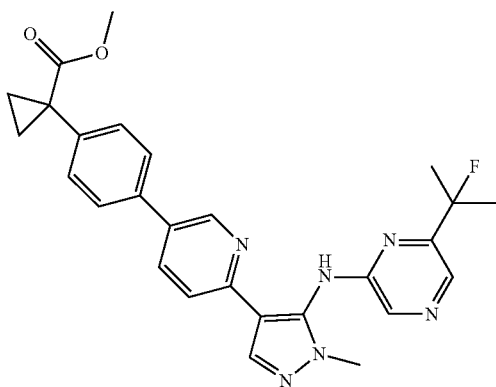 [SMILES: COC(=O)C1(c2ccc(-c3ccc(-c4cnn(C)c4Nc4cncc(C(C)(C)F)n4)nc3)cc2)CC1]

Add Pd₂(dba)₃ (1.10 g, 1.20 mmol), 4,5-bis(diphenylphosphino)-9,9-dimethylxanthene (1.04 g, 1.80 mmol) and cesium carbonate (9.80 g, 30.1 mmol) to 2-chloro-6-(1-fluoro-1-methyl-ethyl)pyrazine (2.50 g, 12.0 mmol, 84 mass %), methyl 1-[4-[6-(5-amino-1-methyl-pyrazol-4-yl)-3-pyridyl]phenyl]cyclopropanecarboxylate (4.19 g, 10.8 mmol, 90 mass %) (Prepared according to Example 1A) in 1,4-dioxane (60 mL), then the reaction mixture is stirred at 100° C. for 5 h under nitrogen. The reaction mixture is concentrated to afford a black residue, which is purified by column chromatography on silica gel eluting with PE/EtOAc (1:1) to afford the title compound (3.10 g, 50.3%) as yellow solid. LCMS (m/z): 487.2 [M+H]⁺.

EXAMPLE 13B

1-[4-[6-[5-[[6-(1-fluoro-1-methyl-ethyl)pyrazin-2-yl]amino]-1-methyl-pyrazol-4-yl]-3-pyridyl]phenyl]cyclopropanecarboxylic acid; hydrochloride

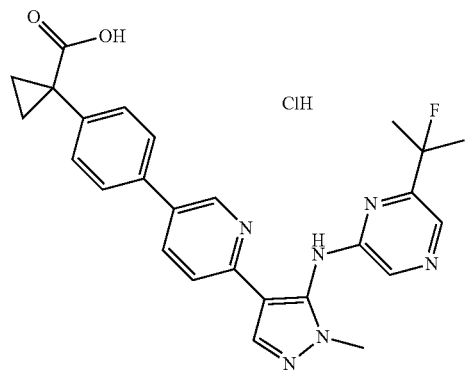 [SMILES: Cn1ncc(-c2ccc(-c3ccc(C4(C(=O)O)CC4)cc3)cn2)c1Nc1cncc(C(C)(C)F)n1 ; Cl]

Add lithium hydroxide hydrate (0.750 g, 17.9 mmol) to methyl 1-[4-[6-[5-[[6-(1-fluoro-1-methyl-ethyl)pyrazin-2-yl]amino]-1-methyl-pyrazol-4-yl]-3-pyridyl]phenyl]cyclopropanecarboxylate (6.10 g, 11.9 mmol) in THF (30 mL) and water (30 mL), then the reaction mixture is stirred at 60° C. for 1 h. The aqueous is acidified by 1N HCl to pH=6, then extracted with EtOAc (60 mL×3), the combined organic phases are concentrated to afford crude product. The crude product is purified by prep-HPLC [column: Phenomenexluna C18 250×50 mm×10 μm, condition: 20-45% B (A: water/0.05% HCl, B: CH3CN), flow rate: 25 mL/min] and lyophilized to afford title compound (2.7380 g, 37.8%) as a yellow solid. LCMS (m/z): 473.1 [M+H]⁺.

¹H NMR (400 MHz, CD₃OD) δ=8.88 (d, J=2.0 Hz, 1H), 8.67 (dd, J=2.4, 8.8 Hz, 1H), 8.36-8.28 (m, 1H), 8.26-8.22 (m, 1H), 8.19 (s, 1H), 8.12-8.05 (m, 1H), 7.71 (d, J=8.4 Hz, 2H), 7.56 (d, J=8.4 Hz, 2H), 3.91-3.85 (m, 3H), 1.67-1.62 (m, 2H), 1.40-1.29 (m, 5H), 1.27-1.22 (m, 2H), 1.19 (s, 1H)

EXAMPLE 14A methyl 1-[4-[6-[5-[(6-isopropylpyrazin-2-yl)amino]-1-methyl-pyrazol-4-yl]-3-pyridyl]-3-(methoxymethyl)phenyl]cyclopropanecarboxylate 1. Synthesis of ethyl 2-(4-bromo-3-methyl-phenyl)acetate

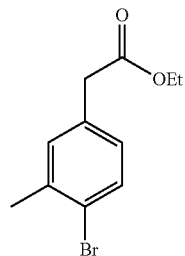

Add sulfuric acid (9.2 g, 5 mL) to a mixture of 2-(4-bromo-3-methyl-phenyl)acetic acid (5.00 g, 20.7 mmol) in ethanol (50 mL) and the reaction is heated to 80° C. for 3 hours. The mixture is cooled to 20° C. and poured into saturated NaHCO₃ solution (30 mL). The mixture is extracted with EtOAc (30 mL×3). The combined organic layers are washed with brine (30 mL), dried over anhydrous sodium sulfate and concentrated to afford title compound (5.30 g, 94.4%) as colorless oil.

¹H NMR (400 MHz, CDCl₃) δ=7.48 (d, J=8.0 Hz, 1H), 7.16 (s, 1H), 6.98 (dd, J=2.0, 8.0 Hz, 1H), 4.16 (q, J=7.2 Hz, 2H), 3.54 (s, 2H), 2.39 (s, 3H), 1.26 (t, J=7.2 Hz, 3H).

2. Synthesis of ethyl 1-(4-bromo-3-methyl-phenyl)cyclopropanecarboxylate

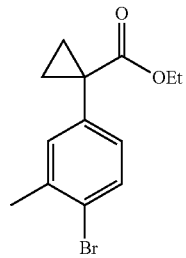 [SMILES: CCOC(=O)C1(c2ccc(Br)c(C)c2)CC1]

Add NaH (1.63 g, 40.6 mmol, 60 mass %) to a mixture of ethyl 2-(4-bromo-3-methyl-phenyl)acetate (5.00 g, 18.5 mmol) in DMF (50 mL) at 20° C. and the mixture is stirred at 50° C. for 1 hour. Then 1,2-dibromoethane (3.68 g, 19.4 mmol) is added and the reaction is stirred at 50° C. for 12 hours. The reaction is quenched with saturated NH₄Cl solution (30 mL) and extracted with EtOAc (30 mL×3). The combined organic layers are washed with brine (30 mL), dried over anhydrous sodium sulfate and concentrated. The residue is purified by flash chromatography eluting with petroleum ether/EtOAc (50:1) to afford the title compound (550 mg, 9.99%) as colorless oil.

¹H NMR (400 MHz, CDCl₃) δ=7.46 (d, J=8.4 Hz, 1H), 7.21 (d, J=2.0 Hz, 1H), 7.03 (dd, J 2.0, 8.4 Hz, 1H), 4.11 (q, J=7.2 Hz, 2H), 2.39 (s, 3H), 1.63-1.56 (m, 2H), 1.22-1.11 (m, 5H).

3. Synthesis of ethyl 1-[4-bromo-3-(bromomethyl) phenyl]cyclopropanecarboxylate

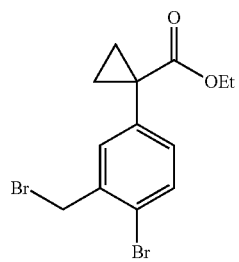 [SMILES: CCOC(=O)C1(c2ccc(Br)c(CBr)c2)CC1]

Add NBS (0.369 g, 2.03 mmol) and 2,2'-azobis(2-methylpropionitrile) (31.0 mg, 0.184 mmol) in carbon tetrachloride (10 mL) to a mixture of ethyl 1-(4-bromo-3-methyl-phenyl)cyclopropanecarboxylate (550 mg, 1.84 mmol) in carbon tetrachloride (10 mL) and the mixture is heated to 70° C. for 12 hours. The mixture is diluted with water (20 mL) and extracted with EtOAc (30 mL×3). The combined organic layers are washed with brine (30 mL), dried over anhydrous sodium sulfate and concentrated. The residue is purified by flash chromatography eluting with petroleum ether/EtOAc (20:1) to afford the title compound (500 mg, 71.1%) as colorless oil.

¹H NMR (400 MHz, CDCl₃) δ=7.51 (d, J=8.4 Hz, 1H), 7.44 (d, J=2.0 Hz, 1H), 7.16 (dd, J 2.0, 8.4 Hz, 1H), 4.59 (s, 2H), 4.10 (q, J=7.2 Hz, 2H), 1.65-1.60 (m, 2H), 1.21-1.13 (m, 5H).

4. Synthesis of methyl 1-[4-bromo-3-(methoxymethyl)phenyl]cyclopropane carboxylate

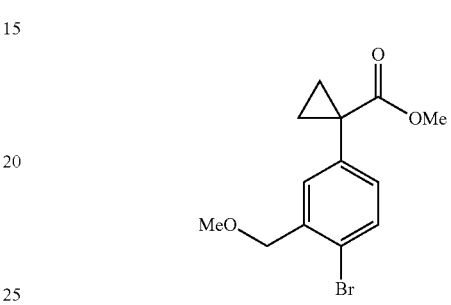

Add sodium methoxide (0.0515 g, 0.944 mmol) to a solution of ethyl 1-[4-bromo-3-(bromomethyl)phenyl]cyclopropanecarboxylate (300 mg, 0.787 mmol) in methanol (5 mL) at 20° C. and the reaction is stirred at 50° C. for 2 hours. The mixture is diluted with water (20 mL) and extracted with EtOAc (30 mL×3). The combined organic layers are washed with brine (30 mL), dried over anhydrous sodium sulfate, filtered and concentrated. The residue is purified by flash chromatography eluting with petroleum ether/EtOAc (20:1) to afford the title compound (200 mg, 80.7%) as colorless oil.

¹H NMR (400 MHz, CDCl₃) δ=7.48 (d, J=8.0 Hz, 1H), 7.44 (d, J=1.6 Hz, 1H), 7.14 (dd, J 2.0, 8.0 Hz, 1H), 4.51 (s, 2H), 3.63 (s, 3H), 3.49 (s, 3H), 1.65-1.58 (m, 2H), 1.22-1.14 (m, 2H).

5. Synthesis of N-[4-(5-bromo-2-pyridyl)-2-methylpyrazol-3-yl]-6-isopropyl-pyrazin-2-amine

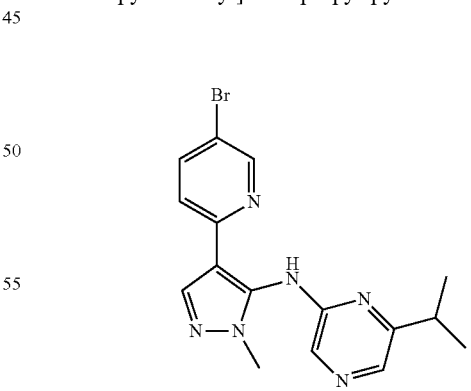

Add sodium hydride in oil (1.26 g, 31.5 mmol, 60 mass %) to a suspension of 4-(5-bromo-2-pyridyl)-2-methyl-pyrazol-3-amine (1.68 g, 6.31 mmol) in DMF (8 mL). The reaction mixture is heated to 50° C. and then 2-chloro-6-isopropyl-pyrazine (1.12 g, 6.94 mmol) is added. The reaction mixture is stirred at 50° C. for 1 hour. The reaction mixture is poured into saturated ammonium chloride solution (20 mL) and extracted with EtOAc (30 mL*2). The combined organic layers are washed with brine (20 mL×2), dried over sodium sulfate and filtered and concentrated to afford the residue. The residue is purified by column chromatography on silica gel (0-30% EtOAc in PE) to afford title compound (850 mg, 34.3%) as a yellow solid. LCMS (m/z): 373.0 [M+H]⁺.

6. Synthesis of methyl 1-[4-[6-[5-[(6-isopropylpyrazin-2-yl)amino]-1-methyl-pyrazol-4-yl]-3-pyridyl]-3-(methoxymethyl)phenyl]cyclopropanecarboxylate

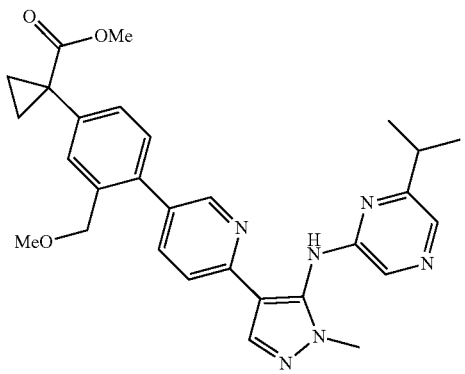 [SMILES: COCc1cc(C2(C(=O)OC)CC2)ccc1-c1ccc(-c2cnn(C)c2Nc2cncc(C(C)C)n2)nc1]

Add [1,1'-bis(diphenylphosphino)ferrocene]dichloropalladium(II) (0.0356 g, 0.0476 mmol) to a mixture of methyl 1-[4-bromo-3-(methoxymethyl)phenyl]cyclo propanecarboxylate (150 mg, 0.476 mmol), bis(pinacolato)diboron (0.128 g, 0.500 mmol) and potassium acetate (0.142 g, 1.43 mmol) in 1,4-dioxane (5 mL) under nitrogen. The reaction is heated to 100° C. for 1 hour. The mixture is cooled to 20° C. and then N-[4-(5-bromo-2-pyridyl)-2-methyl-pyrazol-3-yl]-6-isopropyl-pyrazin-2-amine (0.196 g, 0.500 mmol), [1,1'-bis(diphenylphosphino)ferrocene]dichloropalladium (II) (0.0356 g, 0.0476 mmol), sodium carbonate (0.153 g, 1.43 mmol) and water (0.5 mL) are added under nitrogen. The reaction is heated to 100° C. for 12 hours. The mixture is diluted with EtOAc (30 mL) and the solid is filtered off. The filtrate is diluted with water (30 mL) and extracted with EtOAc (30 mL×3). The combined organic layers are washed with brine (30 mL), dried over anhydrous sodium sulfate and concentrated. The residue is purified by flash chromatography eluting with petroleum ether/EtOAc (1:2) to afford title compound (153 mg, 62.7%) as yellow oil. LCMS (m/z): 513.3 [M+H]⁺.

¹H NMR (400 MHz, CDCl₃) δ=9.38 (s, 1H), 8.54 (d, J=1.6 Hz, 1H), 8.07 (s, 1H), 7.98 (s, 1H), 7.92 (s, 1H), 7.74 (dd, J=2.0, 8.0 Hz, 1H), 7.54 (d, J=8.4 Hz, 1H), 7.51 (d, J=1.6 Hz, 1H), 7.38 (dd, J=2.0, 8.0 Hz, 1H), 7.25 (d, J=7.6 Hz, 1H), 4.31 (s, 2H), 3.87 (s, 3H), 3.66 (s, 3H), 3.37 (s, 3H), 3.00-2.92 (m, 1H), 1.68-1.63 (m, 2H), 1.27-1.25 (m, 8H).

EXAMPLE 14B

1-[4-[6-[5-[(6-isopropylpyrazin-2-yl)amino]-1-methyl-pyrazol-4-yl]-3-pyridyl]-3-(methoxymethyl)phenyl]cyclopropanecarboxylic acid; hydrochloride

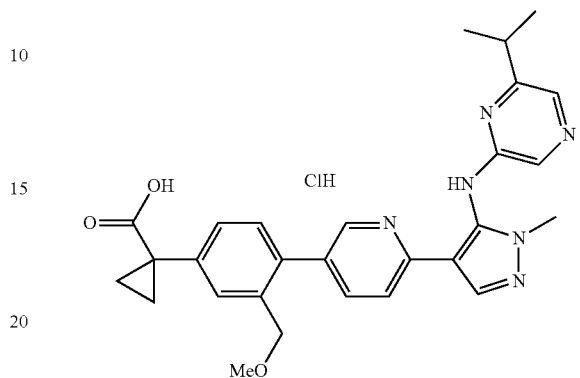

Add lithium hydroxide hydrate (0.0380 g, 0.895 mmol) to a mixture of methyl 1-[4-[6-[5-[(6-isopropylpyrazin-2-yl)amino]-1-methyl-pyrazol-4-yl]-3-pyridyl]-3-(methoxymethyl)phenyl]cyclopropanecarboxylate (0.170 g, 0.298 mmol, 90 mass %) in THF (3 mL) and water (0.5 mL) and the mixture is heated to 50° C. for 12 hours. The mixture is adjusted pH to 5-6 with 1.0M HCl solution and the mixture is extracted with EtOAc (30 mL×3). The combined organic layers are washed with brine (30 mL), dried over anhydrous sodium sulfate, filtered and concentrated. The mixture is purified by prep-HPLC (column: YMC-Actus Triart C18 100×30 mm×5 μm, Gradient: 32-62% B (A=water/0.05% HCl, B=acetonitrile), Flow rate: 25 mL/min). The desired fractions are lyophilized to afford title compound (59.5 mg, 36.9%) as a white solid. LCMS (m/z): 499.1 [M+H]⁺.

¹H NMR (400 MHz, DMSO-d6) δ=10.09 (br s, 1H), 8.64 (br s, 1H), 8.36 (br s, 1H), 8.31-8.19 (m, 2H), 7.97-7.80 (m, 2H), 7.50 (br s, 1H), 7.42 (br d, J=7.2 Hz, 1H), 7.30 (d, J 8.0 Hz, 1H), 4.27 (br s, 2H), 3.78 (br s, 3H), 3.22 (s, 3H), 2.77-2.63 (m, 1H), 1.56-1.42 (m, 2H), 1.24-1.09 (m, 2H), 0.93 (d, J=6.4 Hz, 6H).

EXAMPLE 15A

Ethyl 1-[3-(cyanomethyl)-4-[6-[5-[(6-isopropylpyrazin-2-yl)amino]-1-methyl-pyrazol-4-yl]-3-pyridyl]phenyl]cyclopropanecarboxylate 1. Synthesis of ethyl 1-[4-bromo-3-(cyanomethyl)phenyl]cyclopropanecarboxylate

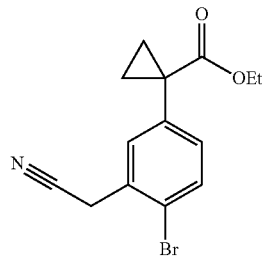 [SMILES: CCOC(=O)C1(c2ccc(Br)c(CC#N)c2)CC1]

Add trimethylsilyl cyanide (0.0637 g, 0.630 mmol) and tetrabutylammonium fluoride (1.0 mol/L) in THF (0.63 mL, 0.630 mmol, 1.0 mol/L) to a solution of ethyl 1-[4-bromo-3-(bromomethyl)phenyl]cyclopropanecarboxylate (0.200 g, 0.525 mmol) (prepared according to Example 14A) in THF (5 mL), and the reaction is stirred at 20° C. for 3 hours. The mixture is diluted with water (20 mL) and extracted with EtOAc (30 mL×3). The combined organic layers are washed with brine (30 mL), dried over anhydrous sodium sulfate and concentrated. The residue is purified by flash chromatography eluting with petroleum ether/EtOAc (20:1) to afford title compound (100 mg, 58.7%) as colorless oil.

$^1$H NMR (400 MHz, CDCl$_3$) δ=7.54 (d, J=8.4 Hz, 1H), 7.51 (d, J=2.0 Hz, 1H), 7.21 (dd, J=2.0, 8.4 Hz, 1H), 4.11 (q, J=7.2 Hz, 2H), 3.84 (s, 2H), 1.69-1.61 (m, 2H), 1.24-1.14 (m, 5H).

2. Synthesis of ethyl 1-[3-(cyanomethyl)-4-[6-[5-[(6-isopropylpyrazin-2-yl)amino]-1-methyl-pyrazol-4-yl]-3-pyridyl]phenyl]cyclopropanecarboxylate

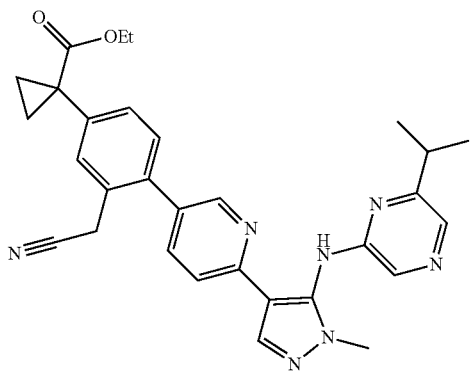 [SMILES: CCOC(=O)C1(c2ccc(-c3ccc(-c4cnn(C)c4Nc4cncc(C(C)C)n4)nc3)c(CC#N)c2)CC1]

Add Pd(dppf)Cl$_2$ (0.023 g, 0.031 mmol) potassium acetate (0.0917 g, 0.925 mmol) to a mixture of ethyl 1-[4-bromo-3-(cyanomethyl)phenyl]cyclopropanecarboxylate (0.100 g, 0.308 mmol), bis(pinacolato)diboron (0.083 g, 0.324 mmol) and potassium acetate (0.0917 g, 0.925 mmol) in 1,4-dioxane (3 mL) under nitrogen. The reaction is heated to 100° C. for 3 hours. The mixture is cooled to 20° C. and then N-[4-(5-bromo-2-pyridyl)-2-methyl-pyrazol-3-yl]-6-isopropyl-pyrazin-2-amine (0.127 g, 0.324 mmol) (prepared according to Example 14A), Pd(dppf)Cl$_2$ (0.0230 g, 0.0308 mmol), sodium carbonate (0.0990 g, 0.925 mmol) and water (0.3 mL) are added. The reaction is heated to 100° C. for 3 hours. The solid is filtered off and the filtrate was diluted with water (20 mL). The mixture is extracted with EtOAc (30 mL×3). The combined organic layers ware washed with brine (30 mL), dried over anhydrous sodium sulfate, filtered and concentrated. The residue is purified by flash chromatography eluting with petroleum ether/EtOAc (1:2) to afford title compound (81.0 mg, 50.4%) as a light yellow solid. LCMS (m/z): 522.1 [M+H]$^+$.

EXAMPLE 15B

1-[3-(cyanomethyl)-4-[6-[5-[(6-isopropylpyrazin-2-yl)amino]-1-methyl-pyrazol-4-yl]-3-pyridyl]phenyl] cyclopropanecarboxylic acid; hydrochloride

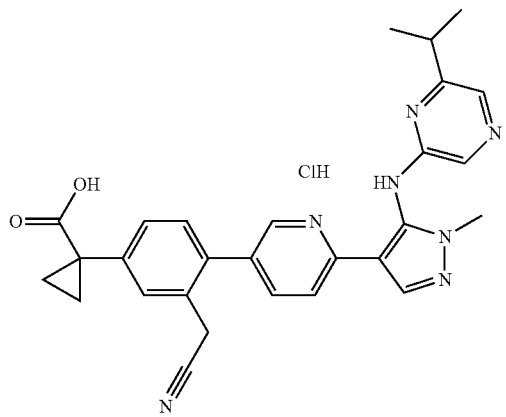 [SMILES: CC(C)c1cncc(Nc2c(-c3ccc(-c4ccc(C5(C(=O)O)CC5)cc4CC#N)cn3)cnn2C)n1 ; Cl]

Add lithium hydroxide hydrate (0.0079 g, 0.186 mmol) to a mixture of ethyl 1-[3-(cyanomethyl)-4-[6-[5-[(6-isopropylpyrazin-2-yl)amino]-1-methyl-pyrazol-4-yl]-3-pyridyl] phenyl]cyclopropanecarboxylate (90.0 mg, 0.155 mmol, 90 mass %) in THF (2 mL) and water (0.2 mL) and the mixture is heated to 50° C. for 12 hours. The mixture is adjusted pH to 5-6 with 1.0M HCl solution and the mixture is extracted with EtOAc (30 mL×3). The combined organic layers are washed with brine (30 mL), dried over anhydrous sodium sulfate, filtered and concentrated. The mixture is purified by prep-HPLC (column: YMC-Actus Triart C18 100×30 mm×5 μm, Gradient: 35-65% B (A=water/0.05% HCl, B=acetonitrile), Flow rate: 25 mL/min). The desired fractions were lyophilized to afford title compound (27.6 mg, 33.2%) as a white solid. LCMS (m/z): 494.1 [M+H]$^+$.

$^1$H NMR (400 MHz, DMSO-d6) δ=9.91 (br s, 1H), 8.62 (d, J=1.6 Hz, 1H), 8.30 (s, 1H), 8.20-8.12 (m, 2H), 7.92 (s, 1H), 7.88 (d, J=8.4 Hz, 1H), 7.53 (s, 1H), 7.43 (dd, J=1.6, 8.0 Hz, 1H), 7.27 (d, J=7.6 Hz, 1H), 4.00 (s, 2H), 3.75 (s, 3H), 2.81-2.70 (m, 1H), 1.57-1.45 (m, 2H), 1.24-1.14 (m, 2H), 0.98 (d, J=6.8 Hz, 6H).

EXAMPLE 16A

Ethyl 1-[3-cyano-4-[6-[5-[(6-isopropylpyrazin-2-yl) amino]-1-methyl-pyrazol-4-yl]-3-pyridyl]phenyl] cyclopropanecarboxylate; hydrochloride 1. Synthesis of ethyl 2-(4-bromo-3-cyano-phenyl)acetate

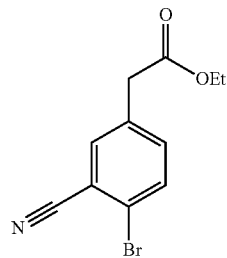 [SMILES: CCOC(=O)Cc1ccc(Br)c(C#N)c1]

Add bromo-(2-ethoxy-2-oxo-ethyl)zinc (2.97 g, 12.7 mmol) (prepared according to Example 9A) to a mixture of 2-bromo-5-iodo-benzonitrile (2.60 g, 8.44 mmol), bis(dibenzylideneacetone)palladium (0.121 g, 0.211 mmol) and 4,5-bis(diphenylphosphino)-9,9-dimethylxanthene (0.122 g, 0.211 mmol) in THF (20 mL), then the reaction mixture is stirred at 65° C. for 1 h under nitrogen. The reaction mixture is quenched with water (10 mL). The result mixture is extracted with EtOAc (10 mL×3). The combined organic phases are washed with water (10 mL), concentrated to afford a black residue, which is purified by column chromatography on silica gel eluting with PE:EtOAc (20:1) to afford the title compound (1.00 g, 42.0% Yield) as a yellow solid.

$^1$H NMR (400 MHz, CDCl$_3$) δ=7.65 (d, J=8.4 Hz, 1H), 7.60 (d, J=2.0 Hz, 1H), 7.39 (dd, J=2.0, 8.4 Hz, 1H), 4.18 (q, J=7.2 Hz, 2H), 3.61 (s, 2H), 1.28 (t, J=7.2 Hz, 3H)

2. Synthesis of ethyl 1-(4-bromo-3-cyano-phenyl)cyclopropanecarboxylate

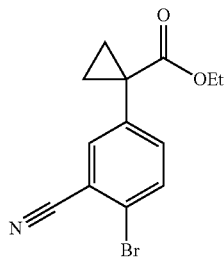 [SMILES: CCOC(=O)C1(c2ccc(Br)c(C#N)c2)CC1]

Add sodium hydride in oil (0.142 g, 3.54 mmol, 60 mass %) to a solution of ethyl 2-(4-bromo-3-cyano-phenyl)acetate (500 mg, 1.77 mmol) in DMF (5 mL), the mixture is stirred at 20° C. for 1 h, then 1,2-dibromoethane (0.333 g, 1.77 mmol) is added to above solution and stirred at 20° C. for 2 h. The reaction mixture is quenched with MeOH (5 mL), diluted with EtOAc (20 mL). The result mixture is washed with water (10 mL×2), concentrated to afford a light yellow residue, which is purified by column chromatography on silica gel eluting with PE:EtOAc (20:1) to afford title compound (260 mg, 47.4%) as a yellow solid.

$^1$H NMR (400 MHz, CHLOROFORM-d) δ=7.68-7.58 (m, 2H), 7.44 (dd, J=2.0, 8.4 Hz, 1H), 4.11 (q, J=7.2 Hz, 2H), 1.70-1.65 (m, 2H), 1.21-1.15 (m, 5H)

3. Synthesis of ethyl 1-[4-[6-(5-amino-1-methyl-pyrazol-4-yl)-3-pyridyl]-3-cyano-phenyl]cyclopropanecarboxylate

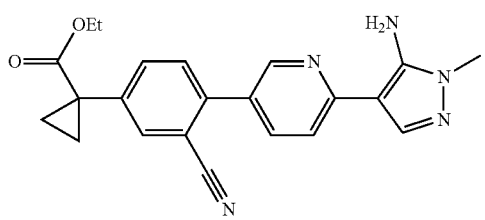 [SMILES: CCOC(=O)C1(c2ccc(-c3ccc(-c4cnn(C)c4N)nc3)c(C#N)c2)CC1]

Add [1,1'-bis(diphenylphosphino)ferrocene]dichloropalladium(II) (0.0482 g, 0.0646 mmol) to a solution of ethyl 1-(4-bromo-3-cyano-phenyl)cyclopropanecarboxylate (200 mg, 0.646 mmol), 4,4,5,5-tetramethyl-2-(4,4,5,5-tetramethyl-1,3-dioxolan-2-yl)-1,3,2-dioxaborolane (0.182 g, 0.711 mmol) and potassium acetate (0.190 g, 1.94 mmol) in 1,4-dioxane (4 mL), then the reaction mixture is stirred at 90° C. for 1 h under nitrogen. The reaction mixture is cooled to 20° C., then 4-(5-bromo-2-pyridyl)-2-methyl-pyrazol-3-amine (0.189 g, 0.711 mmol), sodium carbonate (0.205 g, 1.94 mmol) and water (1 mL) are added to above solution and stirred at 90° C. for 1 h under nitrogen. The reaction mixture is concentrated to afford a black residue, which is purified by column chromatography on silica gel eluting with EtOAc to afford title compound (130 mg, 46.7%) as a yellow oil. LCMS (m/z): 388.1 [M+H]$^+$.

4. Synthesis of ethyl 1-[3-cyano-4-[6-[5-[(6-isopropylpyrazin-2-yl)amino]-1-methyl-pyrazol-4-yl]-3-pyridyl]phenyl]cyclopropanecarboxylate; hydrochloride

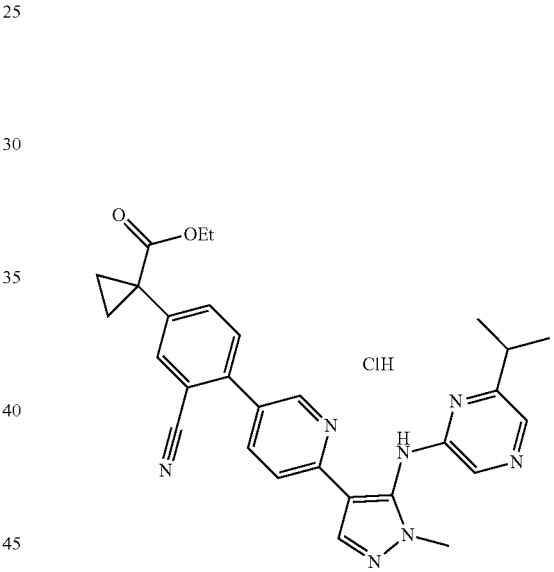

Add tris(dibenzylideneacetone)dipalladium (0.0277 g, 0.0302 mmol) and 4,5-bis(diphenylphosphino)-9,9-dimethylxanthene (0.0262 g, 0.0453 mmol) to a suspensions of ethyl 1-[4-[6-(5-amino-1-methyl-pyrazol-4-yl)-3-pyridyl]-3-cyano-phenyl]cyclopro-panecarboxylate (130 mg, 0.302 mmol), 2-chloro-6-isopropyl-pyrazine (0.0585 g, 0.362 mmol) and cesium carbonate (0.295 g, 0.906 mmol) in 1,4-dioxane (5 mL), then the reaction mixture is stirred at 100° C. for 3 h under nitrogen. The reaction mixture is concentrated to afford a black residue, which is purified by column chromatography on silica gel eluting with EtOAc to afford crude product, which is purified by prep-HPLC [column: YMC-ActusTriart C18 150×30 mm×5 μm, condition: 45-75% B (A: water/0.05% HCl, B: CH3CN), flow rate: 25 mL/min] to afford title compound (60.0 mg, 35.1%) as a yellow solid. LCMS (m/z): 508.2 [M+H]$^+$.

EXAMPLE 16B

1-[3-cyano-4-[6-[5-[(6-isopropylpyrazin-2-yl) amino]-1-methyl-pyrazol-4-yl]-3-pyridyl]phenyl] cyclopropanecarboxylic acid; hydrochloride

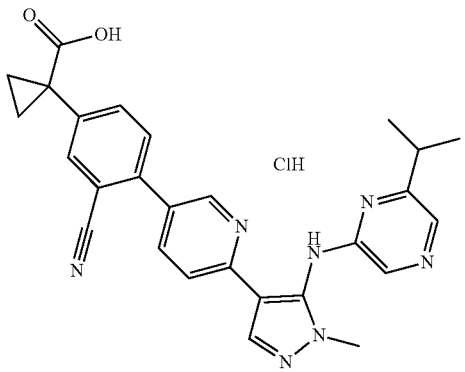 [SMILES: CC(C)c1cncc(Nc2c(-c3ccc(-c4ccc(C5(C(=O)O)CC5)cc4C#N)cn3)cnn2C)n1 ; Cl]

Add lithium hydroxide hydrate (4.4 mg, 0.106 mmol) to a solution of ethyl 1-[3-cyano-4-[6-[5-[(6-isopropylpyrazin-2-yl)amino]-1-methyl-pyrazol-4-yl]-3-pyridyl]phenyl]cyclopropanecarboxylate; hydrochloride (60.0 mg, 0.106 mmol) in methanol (1 mL) and water (1 mL), then the reaction mixture is stirred at 60° C. for 1 h. The reaction mixture is diluted with water (10 mL), acidified by 1N HCl to pH=4. The precipitate is filtered and dried over vacuo to afford the title compound (29.5 mg, 96.9 mass %, 52.3%) as a white solid. LCMS (m/z): 480.1 [M+H]$^+$.

$^1$H NMR (400 MHz, CDCl$_3$) δ=8.65 (s, 1H), 8.10 (s, 1H), 8.02 (s, 1H), 7.92 (d, J=8.0 Hz, 1H), 7.85 (s, 2H), 7.74 (d, J=8.0 Hz, 1H), 7.67 (d, J=8.0 Hz, 1H), 7.53 (d, J=8.0 Hz, 1H), 3.80 (s, 3H), 2.89-2.80 (m, 1H), 1.67-1.60 (m, 2H), 1.28-1.20 (m, 2H), 1.10 (d, J=7.2 Hz, 6H)

EXAMPLE 17

1-[4-[4-[5-[(6-isobutylpyrazin-2-yl)amino]-1-methyl-pyrazol-4-yl]phenyl]phenyl]cyclopropanecarboxylic acid

1. Synthesis of methyl 1-(4-bromophenyl)cyclopropanecarboxylate

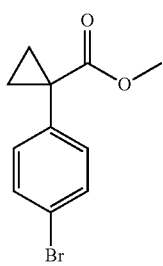

Add 1-(4-bromophenyl)cyclopropanecarboxylic acid (10.0 g, 41.5 mmol) in DMF (50.0 mL, 646 mmol) to potassium carbonate (11.5 g., 83.0 mmol) and iodomethane (11.7 g, 83.0 mmol). Then the reaction mixture is stirred at 20° C. for 0.5 h. the reaction mixture is added with water (50 mL) and the result mixture is extracted with EtOAc (50 mL×3), then the combined organic phases is washed with water (30 mL×2), dried over anhydrous sodium sulfate, filtered and concentrated to give the title compound (10.0 g, 94.5%) as a colorless oil. LCMS (m/z): 254.8/256.8 [M+H, Br$^{79}$/Br$^{81}$]$^+$.

2. Synthesis of methyl 1-[4-(4,4,5,5-tetramethyl-1,3,2-dioxaborolan-2-yl)phenyl]cyclo propanecarboxylate

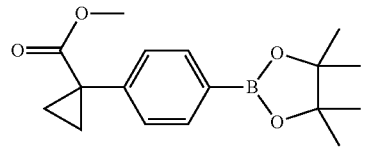 [SMILES: COC(=O)C1(c2ccc(B3OC(C)(C)C(C)(C)O3)cc2)CC1]

Add methyl 1-(4-bromophenyl)cyclopropanecarboxylate (10.0 g, 39.2 mmol) and 4,4,5,5-tetramethyl-2-(4,4,5,5-tetramethyl-1,3,2-dioxaborolan-2-yl)-1,3,2-dioxaborolane (10.5 g., 41.2 mmol) in dioxane (50.0 mL) to potassium acetate (18.9 g, 137 mmol) and [1,1'-bis(diphenylphosphino)ferrocene]dichloropalladium (2.9 g, 3.92 mmol). Then the reaction mixture is stirred at 100° C. for 2 h under N$_2$. To the reaction mixture is added water (50 mL) and EtOAc (100 mL). The solution is separated and the aqueous is extracted with EtOAc (50 mL×3). The combined organic phases are washed with brine (50 mL×2), water (50 mL), dried over anhydrous sodium sulfate, filtered and concentrated to give the title compound (10.0 g, 84.4%) as a white solid. LCMS (m/z): 303.1 [M+H]$^+$.

3. Synthesis of methyl 1-[4-(4-bromophenyl)phenyl]cyclopropanecarboxylate

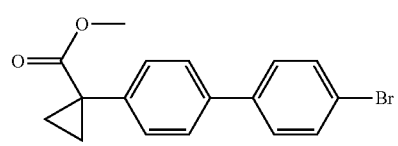 [SMILES: COC(=O)C1(c2ccc(-c3ccc(Br)cc3)cc2)CC1]

Add 1-[4-(4,4,5,5-tetramethyl-1,3,2-dioxaborolan-2-yl)phenyl]cyclo propanecarboxylate (10.0 g, 33.1 mmol), 1-bromo-4-iodo-benzene (10.5 g, 34.7 mmol) in dioxane (50.0 mL) and water (10.0 mL) to potassium carbonate (9.1 g., 66.2 mmol) and [1,1'-bis(diphenylphosphino)ferrocene]dichloropalladium (2.4 g, 3.31 mmol). The reaction mixture is stirred at 100° C. for 2 h under N$_2$. The reaction mixture is concentrated to give a black solid, which was purified by column chromatography (PE:EtOAc=10:1) to give the title compound (10.0 g, 91.2%) as a white solid.

$^1$H NMR (400 MHz, CDCl$_3$) δ=7.56-7.40 (m, 8H), 3.65 (s, 3H), 1.64 (m, 2H), 1.22 (m, 2H).

4. Synthesis of methyl 1-[4-[4-(4,4,5,5-tetramethyl-1,3,2-dioxaborolan-2-yl)phenyl]phenyl]cyclopropanecarboxylate

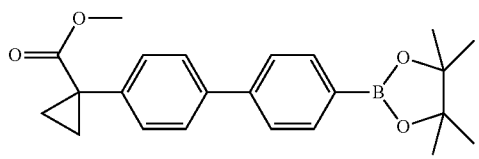 [SMILES: COC(=O)C1(c2ccc(-c3ccc(B4OC(C)(C)C(C)(C)O4)cc3)cc2)CC1]

Add methyl 1-[4-(4-bromophenyl)phenyl]cyclopropanecarboxylate (10.0 g, 30.2 mmol), 4,4,5,5-tetramethyl-2-(4,4,5,5-tetramethyl-1,3,2-dioxaborolan-2-yl)-1,3,2-dioxaborolane (8.1 g, 31.7 mmol,) in 1,4-dioxane (50.0 mL) to potassium acetate (14.6 g, 106 mmol) and [1,1'-bis(diphenylphosphino)ferrocene]dichloropalladium (2.2 g, 3.02 mmol). Then the reaction mixture is stirred at 100° C. for 2 h under $N_2$. The reaction mixture is concentrated to give a black solid. The black solid is purified by column chromatography (PE:EtOAc=10:1) to give the title compound (8.00 g, 70.0%) as a light yellow solid.

$^1$H NMR (400 MHz, CDCl$_3$) δ=7.87 (m, 2H), 7.61-7.57 (m, 4H), 7.41 (m, 2H), 3.65 (s, 3H), 1.64 (m, 2H), 1.22 (m, 2H).

5. Synthesis of methyl 1-[4-[4-(5-amino-1-methyl-pyrazol-4-yl)phenyl]phenyl]cyclopropanecarboxylate

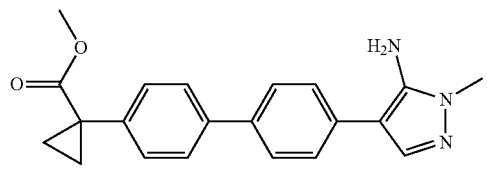 [SMILES: COC(=O)C1(c2ccc(-c3ccc(-c4cnn(C)c4N)cc3)cc2)CC1]

Add 1-[4-[4-(4,4,5,5-tetramethyl-1,3,2-dioxaborolan-2-yl)phenyl]phenyl]cyclopropanecarboxylate (2.00 g, 5.29 mmol), 4-bromo-2-methyl-pyrazol-3-amine (1.1 g, 6.34 mmol), tetrakis(triphenylphosphine)palladium (0.60 g, 0.529 mmol) in ethanol (4.00 mL), toluene (20.0 mL) and water (3.00 mL) to sodium carbonate (2.3 g, 21.1 mmol). The mixture is stirred at 110° C. for 4 h under N2. The reaction mixture is concentrated to give a yellow residue. The residue is purified by column chromatography (DCM:MeOH=10:1) to give the title compound (1.12 g, 61.0%) as a yellow solid. LCMS (m/z): 347.9 [M+H]$^+$.

6. Synthesis of 1-[4-[4-[5-[(6-chloropyrazin-2-yl)amino]-1-methyl-pyrazol-4-yl]phenyl]phenyl]cyclopropanecarboxylic acid

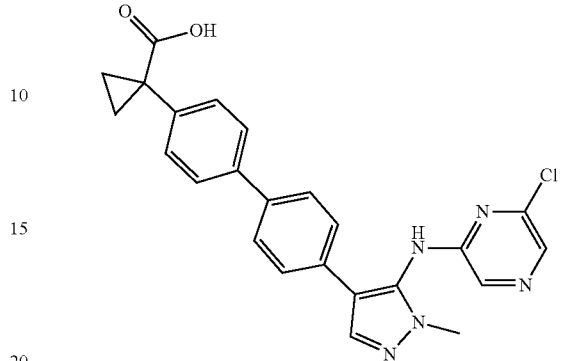

Add sodium hydride (60 mass %) in oil (0.131 g, 3.28 mmol, 60 mass %) to the solution of methyl 1-[4-[4-(5-amino-1-methyl-pyrazol-4-yl)phenyl]phenyl]cyclopropanecarboxylate (300 mg, 0.820 mmol) in DMF (3 mL). The reaction mixture is heated to 50° C. and then 2,6-dichloropyrazine (0.123 g, 0.820 mmol) is added. The reaction mixture is stirred at 50° C. for 2 hours. The reaction mixture is poured into ammonium chloride solution (50 ml) and extracted with EtOAc (50 mL×2). The combined organic layers are washed with brine (40 mL×3), dried over sodium sulfate, filtered and concentrated to afford the crude product. The crude product is purified by prep-HPLC (column: Phenomenex Gemini 150*25 mm*10 m, Gradient: 36-66% B (A=water/0.05% HCl, B=acetontrile), Flow rate: 25 mL/min) to afford the title product (75.0 mg, 20.8%) as a yellow solid. LCMS (m/z) 446.0 [M+H]$^+$.

7. Synthesis of 1-[4-[4-[1-methyl-5-[[6-(2-methylprop-1-enyl)pyrazin-2-yl]amino]pyrazol-4-yl]phenyl]phenyl]cyclopropanecarboxylic acid

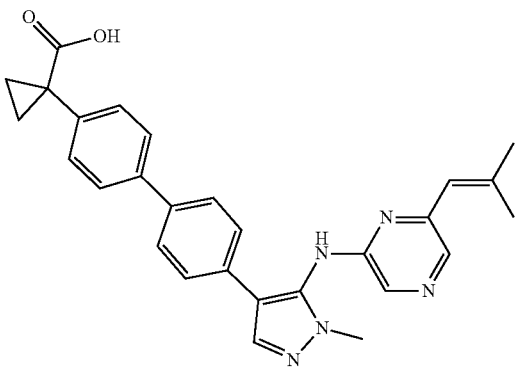 [SMILES: CC(C)=Cc1cncc(Nc2c(-c3ccc(-c4ccc(C5(C(=O)O)CC5)cc4)cc3)cnn2C)n1]

Add [1,1'-bis(diphenylphosphino)ferrocene]dichloropalladium (0.0127 g, 0.0170 mmol) to a solution of 4,4,5,5-tetramethyl-2-(2-methylprop-1-enyl)-1,3,2-dioxaborolane (0.0329 g, 0.179 mmol), sodium carbonate (0.0361 g, 0.341 mmol) and 1-[4-[4-[5-[(6-chloropyrazin-2-yl)amino]-1-methyl-pyrazol-4-yl]phenyl]phenyl]cyclopropanecarboxylic acid (75.0 mg, 0.170 mmol) in 1,4-dioxane (6 mL) and water (1 mL) under N$_2$. Then the reaction mixture is stirred at 100° C. for 2 h under N$_2$. The mixture is diluted with water (30 mL) and extracted with EtOAc (40 mL×3). The combined organic layers were washed with brine (40 mL), dried over anhydrous Na$_2$SO$_4$, filtered and evaporated to afford the title product (63.0 mg 79.4%) as a yellow solid. LCMS: (m/z) 466.2 [M+H]$^+$.

8. Synthesis of 1-[4-[4-[5-[(6-isobutylpyrazin-2-yl)amino]-1-methyl-pyrazol-4-yl]phenyl]phenyl]cyclopropanecarboxylic acid

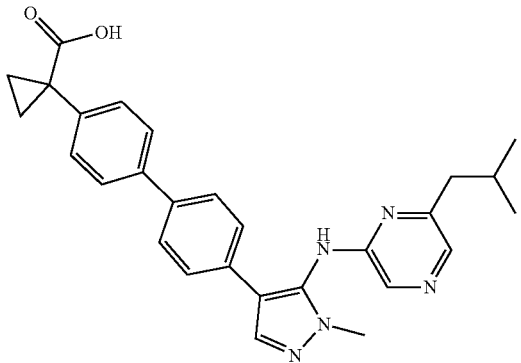 [SMILES: CC(C)Cc1cncc(Nc2c(-c3ccc(-c4ccc(C5(C(=O)O)CC5)cc4)cc3)cnn2C)n1]

Add palladium on activated carbon (10.0 mg, 10 mass %) to a solution of 1-[4-[4-[1-methyl-5-[[6-(2-methylprop-1-enyl)pyrazin-2-yl]amino]pyrazol-4-yl]phenyl]phenyl]cyclopropanecarboxylic acid (70.0 mg, 0.135 mmol, 90 mass %) in methanol (5 mL). Then the reaction mixture is stirred under molecular hydrogen (15 psi, balloon) at 25° C. for 1 h. The mixture is filtered and the filtrate is concentrated to afford the crude product. The crude product is purified by prep-HPLC [Column:YMC-Actus Triart C18 150×30 5 φm; Condition: 43-73% B (A=0.05% HCl, B=acetonitrile); FlowRate: 25 mL/min] to afford the title product (22.0 mg, 34.8%) as a yellow solid. LCMS: (m/z) 468.4 [M+H]$^+$.

$^1$H NMR: (400 MHz, DMSO-d6) δ=9.17 (s, 1H), 7.92-7.85 (m, 2H), 7.78 (s, 1H), 7.58-7.51 (m, 6H), 7.40-7.32 (m, 2H), 3.65 (s, 3H), 2.34 (d, J=6.8 Hz, 2H), 1.87-1.74 (m, 1H), 1.50-1.42 (m, 2H), 1.18-1.11 (m, 2H), 0.75 (d, J=6.8 Hz, 6H).

EXAMPLE 18A

Methyl 1-[4-[2-[5-[(6-isopropylpyrazin-2-yl)amino]-1-methyl-pyrazol-4-yl]pyrimidin-5-yl]phenyl]cyclopropanecarboxylate 1. Synthesis of (E)-2-(5-bromopyrimidin-2-yl)-3-ethoxy-prop-2-enenitrile

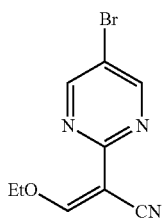 [SMILES: CCO/C=C(/C#N)c1ncc(Br)cn1]

Add acetic anhydride (2.50 g, 23.7 mmol) to a solution of 2-(5-bromopyrimidin-2-yl)acetonitrile (950 mg, 4.75 mmol) and triethyl orthoformate (3 mL, 17.7 mmol), the reaction mixture is stirred at 120° C. for 5 h. The reaction mixture is concentrated to afford title compound (0.96 g, 79.6%) as brown crude. LCMS (m/z): 255.9 [M+H]$^+$.

2. Synthesis of 4-(5-bromopyrimidin-2-yl)-2-methyl-pyrazol-3-amine

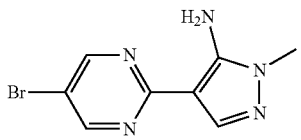

Add methylhydrazine (2.18 g, 18.9 mmol, 40 mass %) to a solution of (E)-2-(5-bromopyrimidin-2-yl)-3-ethoxy-prop-2-enenitrile (0.96 g, 3.78 mmol) is dissolved in ethanol (3 mL). The reaction mixture is heated to 100° C. for 2 hours. The reaction mixture is concentrated, and purified by flash chromatography eluting with petroleum ether:EtOAc (3:1) to afford title compound (0.7 g, 72.9%) as a brown crude.

$^1$H NMR (DMSO-d6, 400 MHz) δ=8.74 (s, 2H), 8.02 (s, 1H), 7.70 (s, 1H), 6.50 (br s, 2H), 4.87-4.72 (m, 1H), 4.79 (br s, 1H), 3.57 (s, 3H), 2.90 (s, 2H).

3. Synthesis of N-[4-(5-bromopyrimidin-2-yl)-2-methyl-pyrazol-3-yl]-6-isopropyl-pyrazin-2-amine

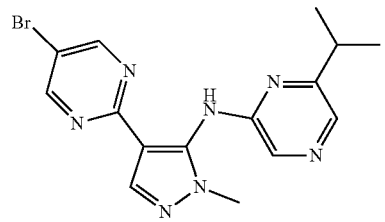 [SMILES: CC(C)c1cncc(Nc2c(-c3ncc(Br)cn3)cnn2C)n1]

Add sodium hydride in oil (0.165 g, 4.13 mmol, 60 mass %) to the suspension of 4-(5-bromopyrimidin-2-yl)-2-methyl-pyrazol-3-amine (210 mg, 0.826 mmol) in N,N-dimethylformamide (3 mL). The reaction mixture is heated to 50° C. and then 2-chloro-6-isopropyl-pyrazine (0.140 g, 0.909 mmol) is added. The reaction mixture is stirred at 50° C. for 3 hours. The reaction mixture is poured into ammonium chloride solution (50 ml) and extracted with EtOAc (50 mL×2). The combined organic layers are washed with brine (20 mL), dried over sodium sulfate and concentrated to afford the crude product. The crude product is purified by flash chromatography eluting with petroleum ether:EtOAc (1:3) to afford title compound (140 mg, 45.3%) as a yellow solid. LCMS (m/z): 374.0 [M+H]$^+$.

4. Synthesis of methyl 1-[4-[2-[5-[(6-isopropylpyrazin-2-yl)amino]-1-methyl-pyrazol-4-yl]pyrimidin-5-yl]phenyl]cyclopropanecarboxylate

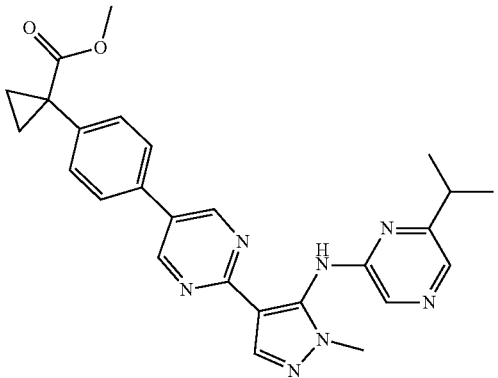 [SMILES: COC(=O)C1(c2ccc(-c3cnc(-c4cnn(C)c4Nc4cncc(C(C)C)n4)nc3)cc2)CC1]

Add [1,1'-bis(diphenylphosphino)ferrocene]dichloropalladium(II) (0.0140 g, 0.0187 mmol) to a suspensions of methyl 1-[4-(4,4,5,5-tetramethyl-1,3,2-dioxaborolan-2-yl) phenyl]cyclopropanecarboxylate (0.125 g, 0.393 mmol), sodium carbonate (0.0793 g, 0.748 mmol) and N-[4-(5-bromopyrimidin-2-yl)-2-methyl-pyrazol-3-yl]-6-isopropyl-pyrazin-2-amine (200 mg, 0.374 mmol, 70 mass %) in 1,4-dioxane (4 mL) and water (1 mL) under $N_2$. Then the reaction mixture is stirred at 100° C. for 3 h under $N_2$. The reaction mixture is concentrated to give a black solid. The mixture is diluted with water (20 mL) and extracted with EA (30 mL×3). The combined organic layers are washed with brine (20 mL), dried over anhydrous $Na_2SO_4$, filtered and evaporated to afford the crude product. The crude product is purified by flash chromatography eluting with petroleum ether:EtOAc (1:2) to afford title compound (90 mg, 51.2%) as a yellow solid, LCMS (m/z): 470.2 [M+H]$^+$.

EXAMPLE 18B

1-[4-[2-[5-[(6-isopropylpyrazin-2-yl)amino]-1-methyl-pyrazol-4-yl]pyrimidin-5-yl]phenyl]cyclopropanecarboxylic acid

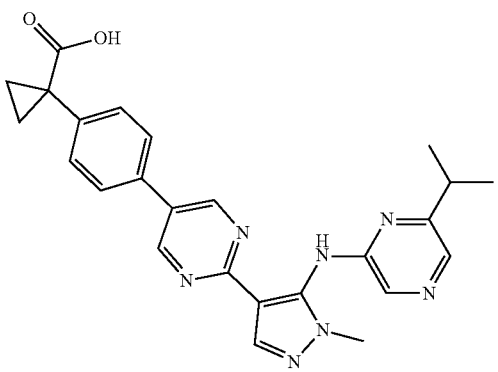 [SMILES: CC(C)c1cncc(Nc2c(-c3ncc(-c4ccc(C5(C(=O)O)CC5)cc4)cn3)cnn2C)n1]

Add lithium hydroxide hydrate (0.0205 g, 0.479 mmol) to a solution of methyl 1-[4-[2-[5-[(6-isopropylpyrazin-2-yl) amino]-1-methyl-pyrazol-4-yl]pyrimidin-5-yl]phenyl]cyclopropanecarboxylate (90 mg, 0.192 mmol,) in THF (4 mL) and water (2 mL). The reaction mixture is stirred at 50° C. for 12 hours. The mixture is adjusted to pH=5-6 with 1 N HCl, extracted with EtOAc (40 mL×3). The combined organic layers are washed with brine (30 mL), dried over $Na_2SO_4$, filtered and concentrated. The crude product is purified by prep-HPLC [Column:YMC-Actus Triart C18 150×30, 5 μm; Condition: 36-66% B (A=0.05% HCl, B=acetonitrile); FlowRate: 25 mL/min] to afford the title compound (44.3 mg, 50.7% Yield) as a white solid, LCMS (m/z): 456.2 [M+H]$^+$.

$^1$H NMR (400 MHz, DMSO-d6) δ=9.43 (s, 1H), 8.92 (s, 2H), 8.12 (s, 1H), 8.09 (s, 1H), 7.87 (s, 1H), 7.64 (d, J=8.0 Hz, 2H), 7.42 (d, J=8.0 Hz, 2H), 3.71 (s, 3H), 2.79-2.71 (m, 1H), 1.49-1.43 (m, 2H), 1.18-1.13 (m, 2H), 0.98 (d, J=6.8 Hz, 6H).

EXAMPLE 19A

Methyl 1-[4-[5-[5-[(6-isopropylpyrazin-2-yl)amino]-1-methyl-pyrazol-4-yl]pyrazin-2-yl]phenyl]cyclopropanecarboxylate 1. Synthesis of methyl 1-[4-(5-chloropyrazin-2-yl) phenyl]cyclopropanecarboxylate

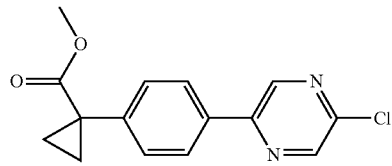 [SMILES: COC(=O)C1(c2ccc(-c3cnc(Cl)cn3)cc2)CC1]

Add [1,1'-bis(diphenylphosphino)ferrocene]dichloropalladium(II) (0.445 g, 0.596 mmol) to the suspensions of methyl 1-[4-(4,4,5,5-tetramethyl-1,3,2-dioxaborolan-2-yl) phenyl]cyclo propanecarboxylate (2.00 g, 5.4 mmol,), sodium carbonate (1.26 g, 11.9 mmol) and 2,5-dichloropyrazine (8.93 mmol) in 1,4-dioxane (20 mL) and water (4 mL) under $N_2$. Then the reaction mixture is stirred at 100° C. for 3 h under $N_2$. The reaction mixture is concentrated to give a black solid. The mixture is diluted with water (20 mL) and extracted with EtOAc (30 mL×3). The combined organic layers are washed with brine (20 mL), dried over anhydrous $Na_2SO_4$, filtered and evaporated to afford the crude product. The crude product is purified by flash chromatography eluting with petroleum ether:EtOAc (1:2) to afford title compound (1.0 g 57.6%) as a yellow solid, LCMS (m/z): 288.9 [M+H]$^+$.

$^1$H NMR (400 MHz, CDCl$_3$) δ=8.80 (d, J=1.2 Hz, 1H), 8.65 (d, J=1.2 Hz, 1H), 7.96 (d, J=8.4 Hz, 2H), 7.51 (d, J=8.4 Hz, 2H), 3.67 (s, 3H), 1.72-1.66 (m, 2H), 1.28-1.23 (m, 2H).

2. Synthesis of methyl 1-[4-(5-tributylstannylpyrazin-2-yl)phenyl]cyclopropanecarboxylate

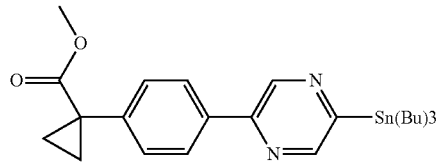

Add tetrakis(triphenylphosphine)palladium(0) (0.108 g, 0.0935 mmol) and tricyclohexylphosphine (0.0535 g, 0.187 mmol) to a solution of methyl 1-[4-(5-chloropyrazin-2-yl)phenyl]cyclopropanecarboxylate (540 mg, 1.87 mmol), hexabutylditin (1.71 g, 2.81 mmol) and lithium chloride (0.481 g, 11.2 mmol) in 1,4-dioxane (3 mL) under N₂. The mixture is stirred at 100° C. for 12 hours. The solid is filtered off. The mixture is diluted with sat. KF (20 mL) and extracted with EtOAc (30 mL×3). The combined organic layers are washed with brine (30 mL), dried over anhydrous Na₂SO₄, filtered and evaporated to afford the crude product. The crude product is purified by flash chromatography eluting with petroleum ether:EtOAc (3:1) to afford title compound (288 mg, 28.3%) as a brown solid, LCMS (m/z): 545.1 [M+H]⁺.

3. Synthesis of methyl 1-[4-[5-[5-(tert-butoxycarbonylamino)-1-methyl-pyrazol-4-yl]pyrazin-2-yl]phenyl]cyclopropanecarboxylate

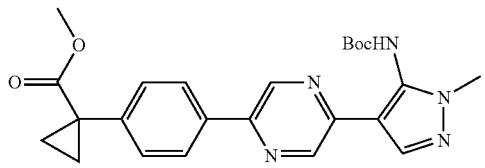 [SMILES: COC(=O)C1(c2ccc(-c3cnc(-c4cnn(C)c4NC(=O)OC(C)(C)C)cn3)cc2)CC1]

Add bis(tri-tert-butylphosphine)palladium(0) (0.0276 g, 0.0530 mmol) to the suspensions of methyl 1-[4-(5-tributylstannylpyrazin-2-yl)phenyl]cyclopropanecarboxylate (288 mg, 0.530 mmol) and tert-butyl N-(4-iodo-2-methyl-pyrazol-3-yl)carbamate (0.256 g, 0.795 mmol) in 1,4-dioxane (4 mL) under N₂. The mixture is stirred at 80° C. for 16 hours. The solid is filtered off. The mixture is diluted with sat. KF (20 mL) and extracted with EtOAc (30 mL×3). The combined organic layers are washed with brine (30 mL), dried over anhydrous Na₂SO₄, filtered and evaporated to afford the crude product. The crude product is purified by flash chromatography eluting with petroleum ether:EtOAc (1:3) to afford title compound (67.0 mg, 28.3%) as a brown solid, LCMS (m/z): 450.2 [M+H]⁺.

4. Synthesis of methyl 1-[4-[5-(5-amino-1-methyl-pyrazol-4-yl)pyrazin-2-yl]phenyl]cyclopropanecarboxylate

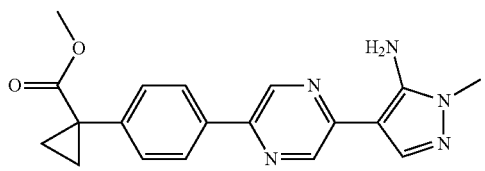

Add trifluoroacetic acid (1 mL) to a solution of methyl 1-[4-[5-[5-(tert-butoxycarbonylamino)-1-methyl-pyrazol-4-yl]pyrazin-2-yl]phenyl]cyclopropanecarboxylate (67.0 mg, 0.150 mmol) in dichloromethane (3 mL). The solution is stirred at 25° C. for 2 hours. The reaction is concentrated under reduced pressure. The residue is added into sat. Na₂CO₃ solution (10 mL) and extracted with CH₂Cl₂ (15 mL×3). The combined organic layers are washed with brine (30 mL), dried over sodium sulfate, filtered, concentrated to afford title compound (32.0 mg, 60.0%) as yellow solid. LCMS (m/z): 350.1 [M+H]⁺.

5. Synthesis of methyl 1-[4-[5-[5-[(6-isopropylpyrazin-2-yl)amino]-1-methyl-pyrazol-4-yl]pyrazin-2-yl]phenyl]cyclopropanecarboxylate

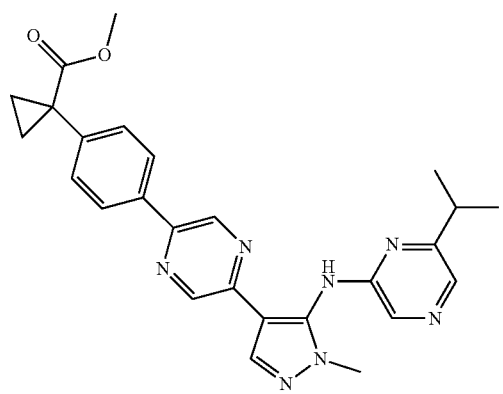 [SMILES: COC(=O)C1(c2ccc(-c3cnc(-c4cnn(C)c4Nc4cncc(C(C)C)n4)cn3)cc2)CC1]

Add tris(dibenzylideneacetone)dipalladium(0) (0.00730 g, 0.00773 mmol) and 4,5-bis(diphenylphosphino)-9,9-dimethylxanthene (0.00691 g, 0.0116 mmol) to the suspensions of methyl 1-[4-[5-(5-amino-1-methyl-pyrazol-4-yl)pyrazin-2-yl]phenyl]cyclopropanecarboxylate (27.0 mg, 0.0773 mmol), 2-chloro-6-isopropyl-pyrazine (0.0136 g, 0.0850 mmol) and cesium carbonate (0.0504 g, 0.155 mmol) in 1,4-dioxane (4 mL) under N₂. The mixture is stirred at 100° C. for 2 hours. The solid is filtered off. The mixture is diluted with water (20 mL) and extracted with EtOAc (30 mL×3). The combined organic layers are washed with brine (30 mL), dried over anhydrous Na₂SO₄, filtered and evaporated to afford the crude product. The crude product is purified by flash chromatography eluting with petroleum ether:EtOAc (1:3) to afford title compound (16.0 mg, 44.1%) as a brown solid, LCMS (m/z): 470.2 [M+H]⁺.

EXAMPLE 19B

1-[4-[5-[5-[(6-isopropylpyrazin-2-yl)amino]-1-methyl-pyrazol-4-yl]pyrazin-2-yl]phenyl]cyclopropanecarboxylic acid; hydrochloride

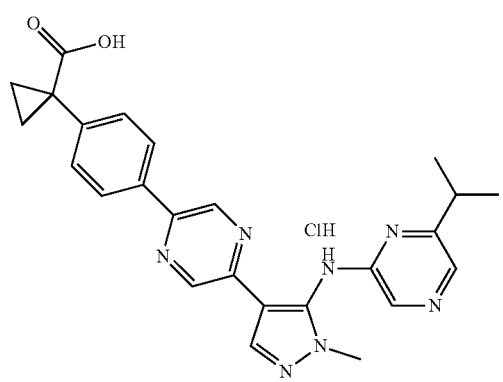 [SMILES: CC(C)c1cncc(Nc2c(-c3cnc(-c4ccc(C5(C(=O)O)CC5)cc4)cn3)cnn2C)n1 ; Cl]

Add lithium hydroxide hydrate (0.00433 g, 0.102 mmol) to a mixture of methyl 1-[4-[5-[5-[(6-isopropylpyrazin-2-yl)amino]-1-methyl-pyrazol-4-yl]pyrazin-2-yl]phenyl]cyclopropanecarboxylate (16 mg, 0.0341 mmol, 80 mass %) in THF (1 mL) and water (0.5 mL) is stirred at 60° C. for 4 hours. The mixture is adjusted pH to 5-6 with 1.0M HCl solution and the mixture is extracted with EtOAc (30 mL×3). The combined organic layers are washed with brine (30 mL), dried over anhydrous sodium sulfate and concentrated to afford the crude. The crude product is purified by prep-HPLC [Column:YMC-Actus Triart C18 150×30, 5 μm; Condition: 36-66% B (A=0.05% HCl, B=acetonitrile); FlowRate: 25 mL/min] to afford title compound (6.3 mg, 37%) as an off-white solid. LCMS (m/z): 456.0 [M+H]$^+$.

$^1$H NMR (METHANOL-d4, 400 MHz) δ=8.93 (s, 1H), 8.85 (s, 1H), 8.59-7.70 (m, 5H), 7.51 (d, J=8.4 Hz, 2H), 3.86 (s, 3H), 3.00-2.92 (m, 1H), 1.65-1.61 (m, 2H), 1.28-1.21 (m, 2H), 1.10 (d, J=6.8 Hz, 6H).

EXAMPLE 20A

Methyl 1-[4-[6-[5-[(6-isopropoxypyrazin-2-yl)amino]-1-methyl-pyrazol-4-yl]-3-pyridyl]phenyl]cyclopropanecarboxylate

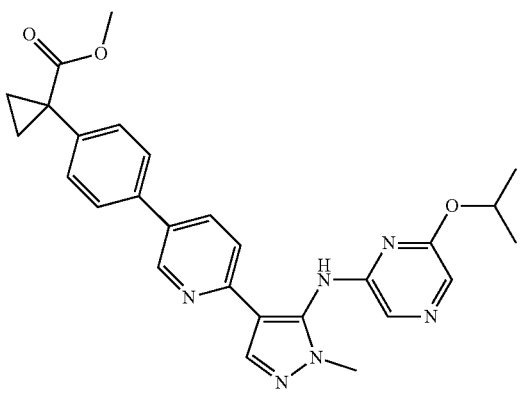 [SMILES: COC(=O)C1(c2ccc(-c3ccc(-c4cnn(C)c4Nc4cncc(OC(C)C)n4)nc3)cc2)CC1]

Add methyl 1-[4-[6-(5-amino-1-methyl-pyrazol-4-yl)-3-pyridyl]phenyl]cyclopropanecarboxylate (240 mg, 0.654 mmol) (prepared according to Example 1A), 2-chloro-6-isopropoxy-pyrazine (138 mg, 0.720 mmol) and cesium carbonate (427 mg, 1.31 mmol) in O$_2$-free 1,4-dioxane (10 mL) to tris(dibenzylideneacetone)dipalladium (61.8 mg, 0.0654 mmol) and 4,5-bis(diphenylphosphino)-9,9-dimethylxanthene (58.6 mg, 0.0982 mmol) at 25° C. The mixture is then stirred at 100° C. for 6 hours. The mixture is filtered through a pad of silica gel (200-300 mush) and the filtrate is concentrated. The residue is purified by flash chromatograph eluting with petroleum ether:EtOAc=1:1 to afford the title compound (200 mg, 59.3%) as brown oil. LCMS (m/z): 485.2 [M+H]$^+$.

EXAMPLE 20B

1-[4-[6-[5-[(6-isopropoxypyrazin-2-yl)amino]-1-methyl-pyrazol-4-yl]-3-pyridyl]phenyl]cyclopropanecarboxylic acid; hydrochloride

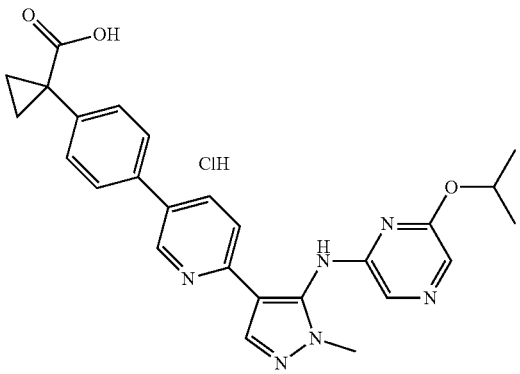 [SMILES: CC(C)Oc1cncc(Nc2c(-c3ccc(-c4ccc(C5(C(=O)O)CC5)cc4)cn3)cnn2C)n1 ; Cl]

Add methyl 1-[4-[6-[5-[(6-isopropoxypyrazin-2-yl)amino]-1-methyl-pyrazol-4-yl]-3-pyridyl]phenyl]cyclopropanecarboxylate (200 mg, 0.388 mmol) in THF (4 mL) and water (2 mL) to lithium hydroxide monohydrate (48.8 mg, 1.16 mmol). The resulting mixture is stirred for 12 hours at 25° C. The mixture is concentrated and diluted with water (5 mL). The mixture is acidified with HCl (1M) to pH=~6. The mixture is extracted with DCM (5 mL×5). The combined organic phases are washed with brine (10 mL), concentrated. The residue is purified by prep-HPLC [column: DYA-5 C18 150×25 mm×5 μm, condition: 18-48% B (A: water/0.05% HCl, B: acetonitrile), flow rate: 25 mL/min] to afford the title compound 1-[4-[6-[5-[(6-isopropoxypyrazin-2-yl)amino]-1-methyl-pyrazol-4-yl]-3-pyridyl]phenyl]cyclopropanecarboxylic acid (48.0 mg, 24.4%) as yellow solid. LCMS (m/z): 471.2 [M+H]$^+$.

$^1$H NMR (400 MHz, DMSO-d6) δ 9.75 (s, 1H), 8.87 (d, J=2.0 Hz, 1H), 8.45 (d, J=8.4 Hz, 1H), 8.31 (s, 1H), 7.86 (d, J=8.4 Hz, 1H), 7.83 (s, 1H), 7.71 (d, J=8.0 Hz, 2H), 7.54 (s, 1H), 7.47 (d, J=8.0 Hz, 2H), 4.73-4.59 (m, 1H), 3.76 (s, 3H), 1.54-1.45 (m, 2H), 1.23-1.14 (m, 2H), 1.05 (d, J=6.0 Hz, 6H).

EXAMPLE 21A

Methyl 1-[4-[6-[1-methyl-5-[[6-(trifluoromethyl)pyrazin-2-yl]amino]pyrazol-4-yl]-3-pyridyl]phenyl]cyclopropanecarboxylate

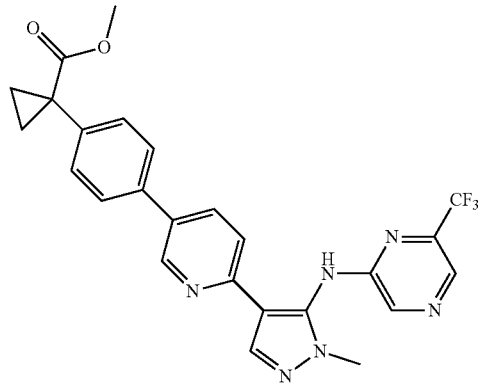 [SMILES: COC(=O)C1(c2ccc(-c3ccc(-c4cnn(C)c4Nc4cncc(C(F)(F)F)n4)nc3)cc2)CC1]

Add methyl 1-[4-[6-(5-amino-1-methyl-pyrazol-4-yl)-3-pyridyl]phenyl]cyclopropanecarboxylate (240 mg, 0.654 mmol) (prepared according to Example 1A), 2-chloro-6-(trifluoromethyl)pyrazine (131 mg, 0.720 mmol) and cesium carbonate (427 mg, 1.31 mmol) in $O_2$-free 1,4-dioxane (10 mL) to tris(dibenzylideneacetone)dipalladium(0) (61.8 mg, 0.0654 mmol) and 4,5-bis(diphenylphosphino)-9,9-dimethylxanthene (58.6 mg, 0.0982 mmol) at 25° C. The mixture is then stirred at 100° C. for 6 hr. The mixture is filtered through a pad of silica gel (200-300 mush) and the filtrate is concentrated. The residue is purified by flash chromatograph eluting with petroleum ether:EtOAc (1:1) to afford the title compound (280 mg, 65.8%) as light yellow oil. LCMS (m/z): 495.2 [M+H]$^+$.

EXAMPLE 21B

1-[4-[6-[1-methyl-5-[[6-(trifluoromethyl)pyrazin-2-yl]amino]pyrazol-4-yl]-3-pyridyl]phenyl]cyclopropanecarboxylic acid

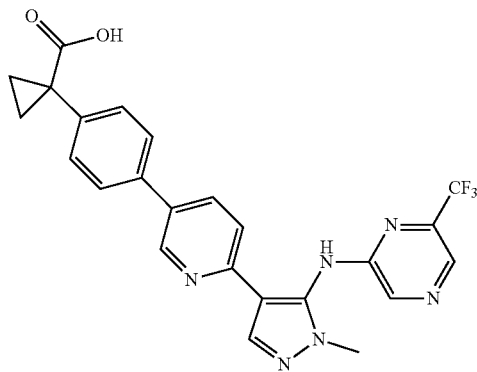 [SMILES: Cn1ncc(-c2ccc(-c3ccc(C4(C(=O)O)CC4)cc3)cn2)c1Nc1cncc(C(F)(F)F)n1]

Add methyl 1-[4-[6-[1-methyl-5-[[6-(trifluoromethyl)pyrazin-2-yl]amino]pyrazol-4-yl]-3-pyridyl]phenyl]cyclopropanecarboxylate (280 mg, 0.430 mmol) in THF (4 mL) and water (2 mL) to lithium hydroxide monohydrate (54.2 mg, 1.29 mmol). The resulting mixture is stirred for 12 hours at 25° C. The mixture is concentrated and diluted with water (5 mL). The mixture is acidified with HCl (1M) to pH=4-6. The mixture is extracted with DCM (5 mL×5). The combined organic phases are washed with brine (10 mL), concentrated, lyophilized to afford the title compound (92.0 mg, 42.1%) as yellow solid. LCMS (m/z): 481.2 [M+H]$^+$.

$^1$H NMR (400 MHz, DMSO-d6) δ 10.13 (br s, 1H), 8.70 (d, J=2.0 Hz, 1H), 8.49 (s, 1H), 8.40 (s, 1H), 8.10 (s, 1H), 8.04-7.93 (m, 1H), 7.70-7.58 (m, 3H), 7.41 (d, J=8.0 Hz, 2H), 3.71 (s, 3H), 1.51-1.43 (m, 2H), 1.20-1.13 (m, 2H).

EXAMPLE 22

1-[4-[6-[5-[(6-isopropylpyrazin-2-yl)amino]-1-methyl-pyrazol-4-yl]-3-pyridyl]-3-methyl-phenyl] cyclopropanecarboxylic acid; hydrochloride

1. Synthesis of 1-(4-bromo-3-methyl-phenyl)cyclopropanecarbonitrile

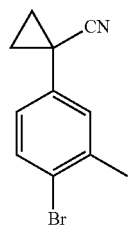

Add sodium hydride in paraffin oil (952 mg, 23.8 mmol, 60 mass %) to a solution of 2-(4-bromo-3-methyl-phenyl)acetonitrile (1.00 g, 4.76 mmol) in THF (5 mL) at 0° C. under $N_2$. The mixture is stirred at 20° C. for 1 hour. 1,2-dibromoethane (1.07 g, 5.71 mmol) is added to the above mixture. The mixture is stirred at 20° C. for 3 hours. The mixture is diluted with saturated NH$_4$Cl (30 mL) and extracted with EtOAc (40 mL×3). The combined organic layers are washed with brine (40 mL), dried over anhydrous Na$_2$SO$_4$, filtered and evaporated to afford the crude product. The crude product is purified by column chromatography on silica gel (0-8%, EtOAc in PE) to afford the title compound (576 mg, 51.2%) as a yellow solid.

$^1$H NMR (400 MHz, CDCl$_3$) δ=7.50 (d, J=8.0 Hz, 1H), 7.20 (d, J=2.0 Hz, 1H), 6.94 (dd, J=8.0, 2.0 Hz, 1H), 2.41 (s, 3H), 1.79-1.66 (m, 2H), 1.44-1.33 (m, 2H)

2. Synthesis of 1-[3-methyl-4-(4,4,5,5-tetramethyl-1,3,2-dioxaborolan-2-yl)phenyl]cyclopropanecarbonitrile

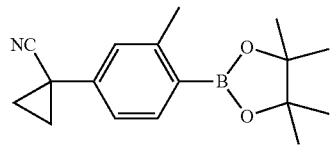 [SMILES: Cc1cc(C2(C#N)CC2)ccc1B1OC(C)(C)C(C)(C)O1]

Add Pd(dppf)Cl$_2$ (182 mg, 0.244 mmol) to a mixture of 1-(4-bromo-3-methyl-phenyl)cyclopropanecarbonitrile (576 mg, 2.44 mmol), 4,4,5,5-tetramethyl-2-(4,4,5,5-tetramethyl-1,3,2-dioxaborolan-2-yl)-1,3,2-dioxaborolane (650 mg, 2.56 mmol) and KOAc (479 mg, 4.88 mmol) in 1,4-dioxane (6 mL) under $N_2$. The mixture is stirred at 100° C. for 3 hours. The solid is filtered off. The mixture is diluted with water (20 mL) and extracted with EtOAc (40 mL×3). The combined organic layers are washed with brine (40 mL), dried over anhydrous Na$_2$SO$_4$, filtered and evaporated to afford the crude product. The crude product is purified by column chromatography on silica gel (0-8%, EtOAc in PE) to afford title product (700 mg, 70 mass %, 71%) as a yellow solid.

$^1$H NMR (400 MHz, CDCl$_3$)=7.74 (d, J=8.0 Hz, 1H), 7.11 (d, J=1.2 Hz, 1H), 7.04 (dd, J=8.0, 1.2 Hz, 1H), 2.54 (s, 3H), 1.78-1.68 (m, 2H), 1.45-1.39 (m, 2H), 1.34 (s, 12H)

3. Synthesis of 1-[4-[6-(5-amino-1-methyl-pyrazol-4-yl)-3-pyridyl]-3-methyl-phenyl]cyclopropanecarbonitrile

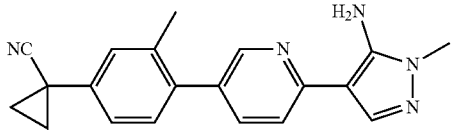 [SMILES: Cc1cc(C2(C#N)CC2)ccc1-c1ccc(-c2cnn(C)c2N)nc1]

Add Pd(dppf)Cl$_2$ (27.7 mg, 0.0371 mmol) to a mixture of 1-[3-methyl-4-(4,4,5,5-tetramethyl-1,3,2-dioxaborolan-2-yl)phenyl]cyclopropanecarbonitrile (300 mg, 0.742 mmol, 70 mass %), 4-(5-bromo-2-pyridyl)-2-methyl-pyrazol-3-amine (229 mg, 0.816 mmol, 90 mass %) and Na$_2$CO$_3$ (196 mg, 1.85 mmol) in water (1 mL) and 1,4-dioxane (4 mL) under N$_2$. The mixture is stirred at 100° C. for 5 hours. The solid is filtered off. The filtrate is diluted with water (20 mL) and extracted with EtOAc (40 mL×3). The combined organic layers are washed with brine (40 mL), dried over anhydrous Na$_2$SO$_4$, filtered and evaporated to afford the crude product. The crude product is purified by column chromatography on silica gel (0-70%, EtOAc in PE) to afford title product (200 mg, 85.2%) as a yellow solid. LCMS (m/z): 330.1 [M+H]$^+$.

$^1$H NMR (400 MHz, CDCl$_3$) δ=8.42 (d, J=1.6 Hz, 1H), 7.73 (s, 1H), 7.56 (dd, J=8.4, 2.4 Hz, 1H), 7.46 (d, J=8.4 Hz, 1H), 7.27-7.25 (m, 1H), 7.22 (d, J=7.6 Hz, 1H), 7.17 (dd, J=8.0, 1.6 Hz, 1H), 5.72-5.46 (m, 2H), 3.72 (s, 3H), 2.32 (s, 3H), 1.85-1.69 (m, 2H), 1.50-1.42 (m, 2H).

4. Synthesis of 1-[4-[6-(5-amino-1-methyl-pyrazol-4-yl)-3-pyridyl]-3-methyl-phenyl]cyclopropanecarboxylic acid

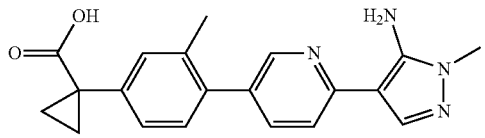 [SMILES: Cc1cc(C2(C(=O)O)CC2)ccc1-c1ccc(-c2cnn(C)c2N)nc1]

Add NaOH (300 mg) in water (3 mL) to a solution of 1-[4-[6-(5-amino-1-methyl-pyrazol-4-yl)-3-pyridyl]-3-methyl-phenyl]cyclopropanecarbonitrile (200 mg, 0.631 mmol) in ethanol (3 mL). The mixture is stirred at 80° C. for 3 hours. The mixture is neutralized with HCl (1M, 20 mL) and extracted with CH$_2$Cl$_2$ (40 mL×3). The combined organic layers are washed with brine (40 mL), dried over anhydrous Na$_2$SO$_4$, filtered and evaporated to afford title product (140 mg, 63.6%) as a yellow solid. LMCS (m/z): 349.0 [M+H]$^+$.

$^1$H NMR (400 MHz, DMSO-d$_6$) δ=12.34 (br s, 1H), 8.41 (d, J=1.6 Hz, 1H), 7.80 (s, 1H), 7.68 (dd, J=8.4, 2.4 Hz, 1H), 7.63-7.55 (m, 1H), 7.36-7.14 (m, 3H), 6.49 (s, 2H), 3.59 (s, 3H), 2.27 (s, 3H), 1.52-1.41 (m, 2H), 1.21-1.12 (m, 2H)

5. Synthesis of 1-[4-[6-[5-[(6-isopropylpyrazin-2-yl)amino]-1-methyl-pyrazol-4-yl]-3-pyridyl]-3-methyl-phenyl]cyclopropanecarboxylic acid; hydrochloride

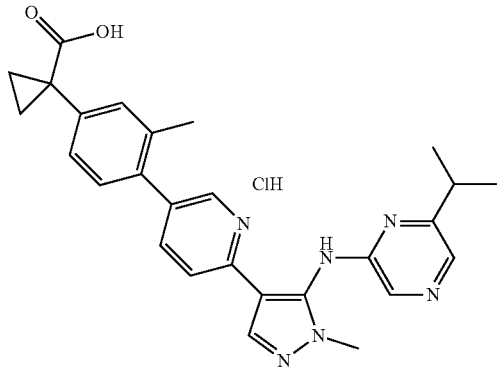 [SMILES: Cc1cc(C2(C(=O)O)CC2)ccc1-c1ccc(-c2cnn(C)c2Nc2cncc(C(C)C)n2)nc1 ; Cl]

Add sodium hydride in oil (92.0 mg, 2.3 mmol, 60 mass %) to a solution of 1-[4-[6-(5-amino-1-methyl-pyrazol-4-yl)-3-pyridyl]-3-methyl-phenyl]cyclopropanecarboxylic acid (200 mg, 0.46 mmol, 80 mass %) in DMF (4 mL) at 0° C. under N$_2$ and then the mixture is stirred at 50° C. for 10 min. A solution of 2-chloro-6-isopropyl-pyrazine (110 mg, 0.51 mmol, 70 mass %) in DMF (1 mL) is added to the above mixture. The mixture is stirred at 50° C. for 3 hours. The mixture is neutralized with HCl (1M) and extracted with CH$_2$Cl$_2$ (30 mL*3). The combined organic layers are washed with brine (30 mL), dried over anhydrous Na$_2$SO$_4$, filtered and evaporated to afford the crude product. The crude product is purified by pre-HPLC [column:YMC-Actus Triart C18 150*30, 5 μm, condition: 25-55% B, A: water (0.05% HCl), B:ACN, flow rate: 25 mL/min] to afford title product (24.8 mg, 99.1 mass %, 28.6%) as a yellow solid. LCMS (m/z): 469.1 [M+H]$^+$.

$^1$H NMR (400 MHz, DMSO-d6) δ=9.78 (br s, 1H), 8.59 (br s, 1H), 8.28-8.18 (m, 1H), 8.17-8.00 (m, 2H), 7.90 (s, 1H), 7.84-7.69 (m, 1H), 7.31 (s, 1H), 7.26 (d, J=8.0 Hz, 1H), 7.18 (d, J=7.6 Hz, 1H), 3.75 (s, 3H), 2.79-2.68 (m, 1H), 2.23 (s, 3H), 1.52-1.40 (m, 2H), 1.19-1.11 (m, 2H), 0.95 (d, J=6.8 Hz, 6H).

EXAMPLE 23

Ammonia; 1-[5-[6-[5-[(6-isopropylpyrazin-2-yl)amino]-1-methyl-pyrazol-4-yl]-3-pyridyl]-2-pyridyl]cyclopropanecarboxylic acid

1. Synthesis of 1-[5-[6-(5-amino-1-methyl-pyrazol-4-yl)-3-pyridyl]-2-pyridyl]cyclopropanecarbonitrile

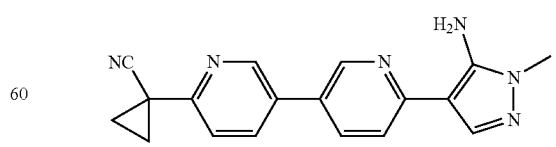

Add [1,1'-bis(diphenylphosphino)ferrocene]dichloropalladium (0.251 g, 0.336 mmol) to a solution of 4-(5-bromo-2-pyridyl)-2-methyl-pyrazol-3-amine (0.90 g, 3.53 mmol), 4,4,5,5-tetramethyl-2-(4,4,5,5-tetramethyl-1,3,2-dioxaborolan-2-yl)-1,3,2-dioxaborolane (0.915 g, 3.53 mmol), 1-(5-bromo-2-pyridyl)cyclopropanecarbonitrile (0.75 g, 3.36 mmol) and potassium acetate (0.842 g, 8.41 mmol) in 1,4-dioxane (8 mL) and water (1 mL) under $N_2$. Then the reaction mixture is stirred at 100° C. for 12 h under $N_2$. The reaction mixture is concentrated to give a black solid, which is purified by flash chromatography eluting with EtOAc:PE (3:1) to give title compound (150 mg, 13.4%) as a brown solid. LCMS (m/z): 317.0 $[M+H]^+$.

2. Synthesis of 1-[5-[6-(5-amino-1-methyl-pyrazol-4-yl)-3-pyridyl]-2-pyridyl]cyclopropanecarboxylic acid

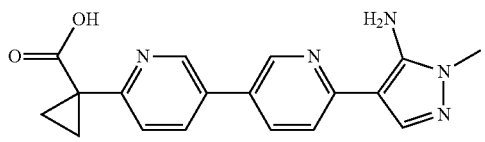 [SMILES: Cn1ncc(-c2ccc(-c3ccc(C4(C(=O)O)CC4)nc3)cn2)c1N]

Add sodium hydroxide (32.0 mass %) in water (3 mL) to a solution of 1-[5-[6-(5-amino-1-methyl-pyrazol-4-yl)-3-pyridyl]-2-pyridyl]cyclopropanecarbonitrile (150 mg, 0.450 mmol) in ethanol (3.00 mL) and water (1.00 mL). The reaction mixture is stirred at 80° C. for 12 hours. The mixture is adjusted to pH=6-7 with 1 N HCl and extracted with $CH_2Cl_2$ (30 mL×3). The combined organic layers are dried over anhydrous sodium sulfate and concentrated to afford title compound (68.0 mg, 40.6%) as a brown solid, LCMS (m/z): 336.0 $[M+H]^+$.

3. Synthesis of ammonia 1-[5-[6-[5-[(6-isopropylpyrazin-2-yl)amino]-1-methyl-pyrazol-4-yl]-3-pyridyl]-2-pyridyl]cyclopropanecarboxylate

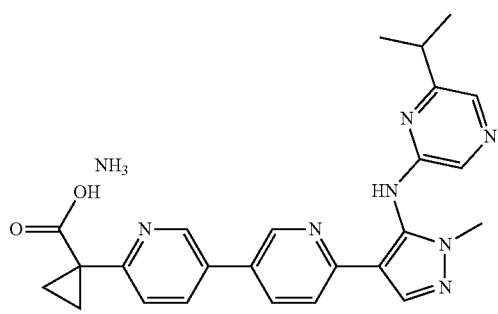

Add tris(dibenzylideneacetone)dipalladium (0.0173 g, 0.0183 mmol) and 4,5-bis(diphenylphosphino)-9,9-dimethylxanthene (0.0164 g, 0.0274 mmol) to a solution of 1-[5-[6-(5-amino-1-methyl-pyrazol-4-yl)-3-pyridyl]-2-pyridyl]cyclopropanecarboxylic acid; hydrochloride (68.0 mg, 0.183 mmol), 2-chloro-6-isopropyl-pyrazine (0.032 g, 0.201 mmol) and cesium carbonate (0.179 g, 0.549 mmol) in 1,4-dioxane (4 mL) under $N_2$. The mixture is stirred at 100° C. for 2 hours. The solid is filtered off. The mixture is acidified to pH=5-6, filtered and evaporated to afford the crude. It is purified by prep-HPLC [Column:YMC-Actus Triart C18 150×30, 5 μm; Condition: 36-66% B (A=0.05% HCl, B=acetonitrile); FlowRate: 25 mL/min] to afford the product (90 mg). Then it is purified by prep-HPLC [Column: YMC-Actus Triart C18 150×30, 5 μm; Condition: 36-66% B (A=0.05% $NH_3.H_2O$, B=acetonitrile); FlowRate: 25 mL/min] to afford title compound (30 mg, 34.9%) as a white solid, LCMS (m/z): 456.3 $[M+H]^+$.

$^1$H NMR (400 MHz, $CD_3OD$) δ=8.82-8.68 (m, 2H), 8.11-7.99 (m, 4H), 7.87 (s, 1H), 7.68 (d, J=8.0 Hz, 1H), 7.59 (d, J=8.0 Hz, 1H), 3.82 (s, 3H), 2.91-2.85 (m, 1H), 1.78-1.67 (m, 2H), 1.44-1.41 (m, 2H), 1.12 (d, J=6.8 Hz, 6H).

EXAMPLE 24

1-[6-[6-[5-[(6-isopropylpyrazin-2-yl)amino]-1-methyl-pyrazol-4-yl]-3-pyridyl]-3-pyridyl]cyclopropanecarboxylic acid; dihydrochloride 1. Synthesis of 1-(6-chloro-3-pyridyl)cyclopropanecarbonitrile

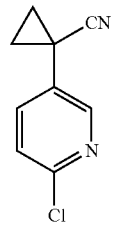 [SMILES: N#CC1(c2ccc(Cl)nc2)CC1]

Add sodium hydride (3.89 g, 97.3 mmol, 60 mass %) to the solution of 2-(6-chloro-3-pyridyl)acetonitrile (5.00 g, 32.4 mmol) in tetrahydrofuran (50 mL) at 0° C. The reaction is stirred at 20° C. for 20 min and then 1-bromo-2-chloroethane (5.64 g, 38.9 mmol) is added. The reaction is stirred at 10° C. for 3 hours. The mixture is added into aq. NaCl (20 mL). The mixture is extracted with EtOAc (20 mL×3). The combined organic layers are washed with brine (10 mL), dried over anhydrous sodium sulfate and concentrated to afford (4.20 g, 72.5%) as a yellow solid, LCMS (m/z): 178.9 $[M+H]^+$.

2. Synthesis of 1-(6-tributylstannyl-3-pyridyl)cyclopropanecarbonitrile

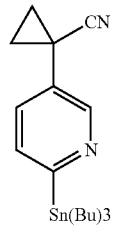

Add 1-(6-chloro-3-pyridyl)cyclopropanecarbonitrile (1.2.0 g, 6.72 mmol), lithium chloride (1.73 g, 40.3 mmol) and hexabutylditin (6.15 g, 10.1 mmol) in 1,4-dioxane (20 mL) to tris(dibenzylideneacetone)dipalladium (0.317 g, 0.336 mmol) and tricyclohexylphosphine (0.192 g, 0.672 mmol) under $N_2$. The mixture is stirred at 100° C. for 12 hours. The solid is filtered off. The mixture is diluted with sat. KF (20 mL) and extracted with EtOAc (30 mL×3). The combined organic layers are washed with brine (30 mL), dried over anhydrous $Na_2SO_4$, filtered and evaporated to afford the crude product. The crude product is purified by flash chromatography eluting with petroleum ether:EtOAc (3:1) to afford title compound (9.6 g, 33.0%) as a brown solid, LCMS (m/z): 435.1 $[M+H]^+$.

3. Synthesis of 1-[6-[6-(5-amino-1-methyl-pyrazol-4-yl)-3-pyridyl]-3-pyridyl]cyclopropanecarbonitrile; hydrochloride

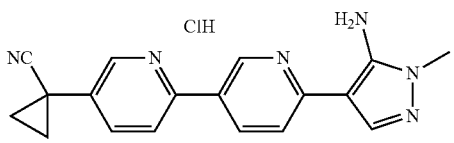

Add 1-(6-tributylstannyl-3-pyridyl)cyclopropanecarbonitrile (0.240 g, 0.560 mmol), lithium chloride (0.0685 g, 1.60 mmol) and 4-(5-bromo-2-pyridyl)-2-methyl-pyrazol-3-amine (135 mg, 0.533 mmol) in N, N-dimethylformamide (2 mL) to [1,1'-bis(diphenylphosphino)ferrocene]dichloropalladium (0.0398 g, 0.0533 mmol) and cuprous iodide (0.207 g, 1.07 mmol) under $N_2$. The mixture is stirred at 100° C. for 2 hours. The mixture is adjusted to pH=6-7 with 1 N HCl and extracted with EtOAc (20 mL×3). The aqueous phase is diluted with 10% EDTA solution (30 mL), and stirred at 20° C. for 1.5 h, filtered and extracted with EtOAc (30 mL×3). The combined organic layers are washed with brine (30 mL), dried over anhydrous sodium sulfate and concentrated to afford title compound (112 mg, 66.4%) as a brown solid, LCMS (m/z): 317.1 $[M+H]^+$.

4. Synthesis of 1-[6-[6-(5-amino-1-methyl-pyrazol-4-yl)-3-pyridyl]-3-pyridyl]cyclopropanecarboxylic acid

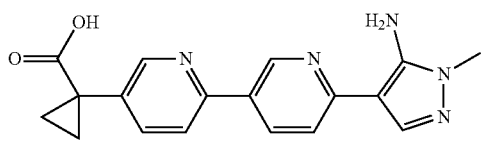

Add 1-[6-[6-(5-amino-1-methyl-pyrazol-4-yl)-3-pyridyl]-3-pyridyl]cyclopropane carbonitrile (112 mg, 0.354 mmol) in ethanol (3.00 mL) and water (1.00 mL) to sodium hydroxide (32.0 mass %) in $H_2O$ (3 mL). The reaction mixture is stirred at 100° C. for 12 hours. The mixture is adjusted to pH=6-7 with 1 N HCl and concentrated to afford the crude. It is purified by prep-HPLC [Column:YMC-Actus Triart C18 150*30, 5 μm; Condition: 36-66% B (A=0.05% HCl, B=acetonitrile); FlowRate: 25 mL/min] to afford the title compound (70.0 mg, 50.0%) as a white solid, LCMS (m/z): 336.0 $[M+H]^+$.

5. Synthesis of 1-[6-[6-[5-[(6-isopropylpyrazin-2-yl)amino]-1-methyl-pyrazol-4-yl]-3-pyridyl]-3-pyridyl]cyclopropanecarboxylic acid; dihydrochloride

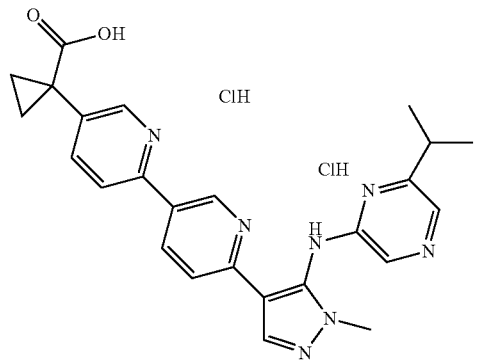 [SMILES: CC(C)c1cncc(Nc2c(-c3ccc(-c4ccc(C5(C(=O)O)CC5)cn4)cn3)cnn2C)n1 ; Cl ; Cl]

Add 1-[6-[6-(5-amino-1-methyl-pyrazol-4-yl)-3-pyridyl]-3-pyridyl]cyclopropanecarboxylic acid (70.0 mg, 0.177 mmol), 2-chloro-6-isopropyl-pyrazine (0.031 g, 0.195 mmol) and cesium carbonate (0.173 g, 0.531 mmol) in 1,4-dioxane (4 mL) to tris(dibenzylideneacetone)dipalladium (0.0167 g, 0.0177 mmol) and 4,5-bis(diphenylphosphino)-9,9-dimethylxanthene (0.0158 g, 0.0265 mmol) under $N_2$. The mixture is stirred at 100° C. for 5 hours. The solid is filtered off. The mixture is acidified to pH=5-6, filtered and evaporated to afford the crude. It is purified by prep-HPLC [Column:YMC-Actus Triart C18 150×30, 5 μm; Condition: 36-66% B (A=0.05% HCl, B=acetonitrile); FlowRate: 25 mL/min] to afford the title compound (14.8 mg, 15.2%) as a white solid, LCMS (m/z): 456.2 $[M+H]^+$.

$^1H$ NMR (400 MHz, DMSO-d6) δ=9.93 (br s, 1H), 9.15 (s, 1H), 8.73 (d, J=8.4 Hz, 1H), 8.69 (s, 1H), 8.32 (s, 1H), 8.19 (s, 1H), 8.09 (d, J=8.4 Hz, 1H), 7.97 (d, J=8.0 Hz, 1H), 7.91-7.84 (m, 2H), 3.75 (s, 3H), 2.71-2.63 (m, 1H), 1.54-1.50 (m, 2H), 1.28-1.25 (m, 2H), 0.89 (d, J=6.8 Hz, 5H).

EXAMPLE 25

Ammonium 1-[4-[4-[5-[(6-cyclopropylpyrazin-2-yl)amino]-1-methyl-pyrazol-4-yl]phenyl]phenyl]cyclopropanecarboxylate

1. Synthesis of 1-[4-[4-[5-[(6-chloropyrazin-2-yl)amino]-1-methyl-pyrazol-4-yl]phenyl]phenyl]cyclopropanecarboxylic acid

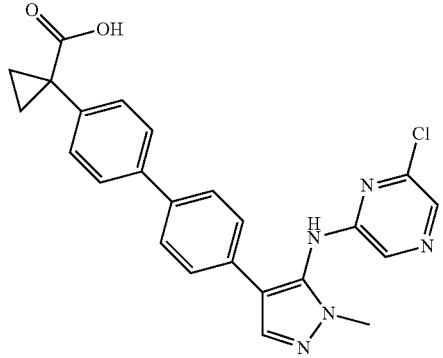 [SMILES: Cn1ncc(-c2ccc(-c3ccc(C4(C(=O)O)CC4)cc3)cc2)c1Nc1cncc(Cl)n1]

Add sodium hydride in paraffin oil (0.273 g, 6.84 mmol) to a solution of methyl 1-[4-[4-(5-amino-1-methyl-pyrazol-4-yl)phenyl]phenyl]cyclopropanecarboxylate (500 mg, 1.37 mmol) (prepared according to Example 17A) in DMF (5 mL) at 10° C. The reaction is stirred at 50° C. for 20 min and then 2,6-dichloropyrazine (0.247 g, 1.64 mmol) is added. The reaction is stirred at 50° C. for 3 hours. The mixture is added into aq. NH$_4$Cl (20 mL). The mixture is extracted with EtOAc (20 mL×3). Then the aqueous phase is acidified by 1 M HCl to pH=4-5. The mixture is extracted with CH$_2$Cl$_2$ (20 mL×3). The combined organic layers are washed with brine (30 mL), dried over anhydrous sodium sulfate and concentrated to afford (490 mg, 80.4%) as a yellow solid, LCMS (m/z): 446.1 [M+H]$^+$.

2. Synthesis of ammonia; 1-[4-[4-[5-[(6-cyclopropylpyrazin-2-yl)amino]-1-methyl-pyrazol-4-yl]phenyl]phenyl]cyclopropanecarboxylic acid

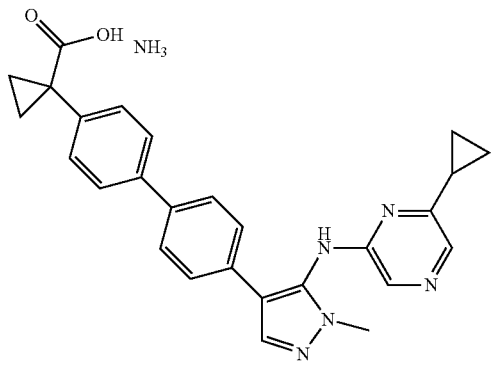

Add [1,1'-bis(diphenylphosphino)ferrocene]dichloropalladium(II) (0.0230 g, 0.0314 mmol) to a mixture of 1-[4-[4-[5-[(6-chloropyrazin-2-yl)amino]-1-methyl-pyrazol-4-yl]phenyl]phenyl]cyclopropanecarboxylic acid (200 mg, 0.314 mmol, 70 mass %), cyclopropylboronic acid (0.0327 g, 0.377 mmol) and cesium carbonate (0.205 g, 0.628 mmol) in water (0.5 mL) and 1,4-dioxane (5 mL) under nitrogen. The reaction is heated to 90° C. for 3 hours. The mixture is diluted with water (20 mL) and adjusted pH=5-6 with 1 M HCl, extracted with EtOAc (30 mL×3). The combined organic layers are washed with brine (30 mL), dried over anhydrous sodium sulfate and concentrated. The crude product is purified by prep-HPLC [Column: YMC-Actus Triart C18 150×30, 5 μm; Condition: 36-66% B (A=0.05% ammonia, B=acetonitrile); FlowRate: 25 mL/min] to afford title compound (18.5 mg, 12.3%) as a white solid. LCMS (m/z): 452.2 [M+H]$^+$.

$^1$H NMR (400 MHz, DMSO-d6) δ=7.89 (s, 1H), 7.86 (s, 1H), 7.76 (s, 1H), 7.59-7.53 (m, 2H), 7.52-7.45 (m, 4H), 7.29 (d, J=8.0 Hz, 2H), 6.08 (br s, 4H), 3.60 (s, 1H), 1.95-1.90 (m, 1H), 1.28-1.26 (m, 2H), 0.88-0.85 (m, 2H), 0.83-0.80 (m, 2H), 0.63-0.60 (m, 2H).

EXAMPLE 26A

Methyl 1-[4-[4-[5-[(6-isopropylpyrazin-2-yl)amino]-1-methyl-pyrazol-4-yl]phenyl]phenyl]cyclopropanecarboxylate 1. Synthesis of methyl 1-[4-[4-[5-[(6-chloropyrazin-2-yl)amino]-1-methyl-pyrazol-4-yl]phenyl]phenyl]cyclopropanecarboxylate

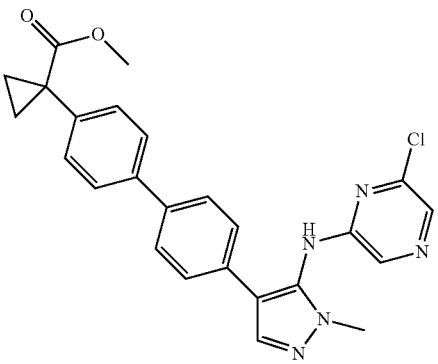 [SMILES: COC(=O)C1(c2ccc(-c3ccc(-c4cnn(C)c4Nc4cncc(Cl)n4)cc3)cc2)CC1]

Add sodium hydride (0.0709 g, 1.77 mmol, 60 mass %) to a solution of methyl 1-[4-[4-(5-amino-1-methyl-pyrazol-4-yl)phenyl]phenyl]cyclopropanecarboxylate (540 mg, 1.48 mmol) (prepared according to Example 17A) in DMF (10 mL) at 0° C. The reaction is stirred at 0° C. for 10 min and then 2,6-dichloropyrazine (0.267 g, 1.77 mmol) is added. The reaction is heated to 30° C. for 6 hours. The mixture is diluted with water (20 mL) and extracted with EtOAc (30 mL×3). Dried over anhydrous sodium sulfate, filtered and concentrated to give the residue and purified by flash chromatography eluting with petroleum ether:EtOAc (1:1) to afford the title compound (160 mg, 90 mass %) as a yellow solid. LCMS (m/z): 460.1 [M+H]$^+$.

2. Synthesis of methyl 1-[4-[4-[5-[(6-isopropenylpyrazin-2-yl)amino]-1-methyl-pyrazol-4-yl]phenyl]phenyl]cyclopropanecarboxylate

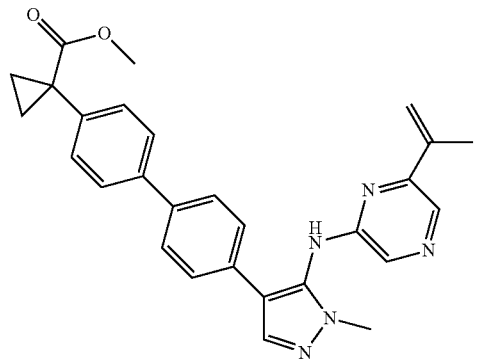 [SMILES: C=C(C)c1cncc(Nc2c(-c3ccc(-c4ccc(C5(C(=O)OC)CC5)cc4)cc3)cnn2C)n1]

Add Pd(dppf)Cl$_2$ (0.0487 g, 0.0665 mmol) and Cs$_2$CO$_3$ (0.651 g, 2.00 mmol) methyl 1-[4-[4-[5-[(6-chloropyrazin-2-yl)amino]-1-methyl-pyrazol-4-yl]phenyl]phenyl]cyclopropanecarboxylate (340 mg, 0.665 mmol, 90 mass %) and 2-isopropenyl-4,4,5,5-tetramethyl-1,3,2-dioxaborolane (0.169 g, 0.998 mmol) in water (0.5 mL) and 1,4-dioxane (5 mL) under nitrogen. The reaction is heated to 90° C. for 5 hours. The mixture is diluted with water (20 mL) and extracted with EtOAc (30 mL×3). The combined organic layers are washed with brine (30 mL), dried over anhydrous sodium sulfate and concentrated. The residue is purified by flash chromatography eluting with petroleum ether:EtOAc (1:1) to afford title compound (325 mg, 72.6%) as a yellow solid. LCMS (m/z): 466.2 [M+H]⁺.

3. Synthesis of methyl 1-[4-[4-[5-[(6-isopropylpyrazin-2-yl)amino]-1-methyl-pyrazol-4-yl]phenyl]phenyl]cyclopropanecarboxylate

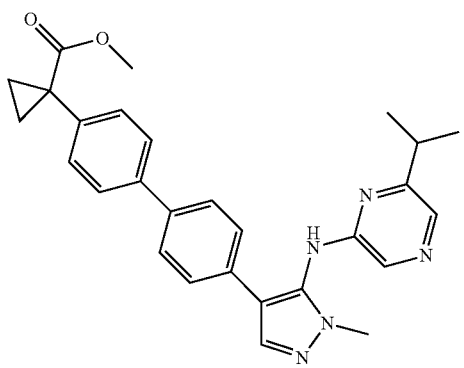 [SMILES: COC(=O)C1(c2ccc(-c3ccc(-c4cnn(C)c4Nc4cncc(C(C)C)n4)cc3)cc2)CC1]

Add methyl 1-[4-[4-[5-[(6-isopropenylpyrazin-2-yl)amino]-1-methyl-pyrazol-4-yl]phenyl]phenyl]cyclopropanecarboxylate (315 mg, 0.677 mmol, 90 mass %) in MeOH (10 mL) to Pd/C (20.0 mg, 10 mass %) and the mixture is stirred under hydrogen (15 psi) for 18 hours. The solid is filtered off and the filtrate is evaporated to afford the title compound (297 mg, 93.9%) as a yellow solid. LCMS (m/z): 468.1 [M+H]⁺.

EXAMPLE 26B

1-[4-[4-[5-[(6-isopropylpyrazin-2-yl)amino]-1-methyl-pyrazol-4-yl]phenyl]phenyl]cyclopropanecarboxylic acid

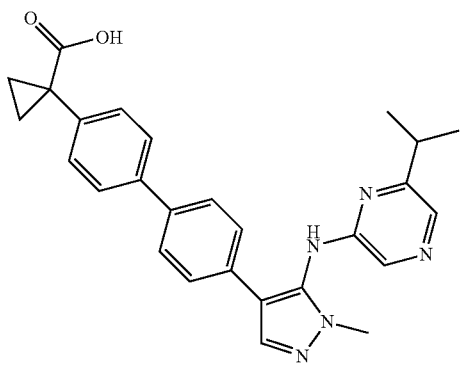 [SMILES: CC(C)c1cncc(Nc2c(-c3ccc(-c4ccc(C5(C(=O)O)CC5)cc4)cc3)cnn2C)n1]

Add methyl 1-[4-[4-[5-[(6-isopropylpyrazin-2-yl)amino]-1-methyl-pyrazol-4-yl]phenyl]phenyl]cyclopropanecarboxylate (295 mg, 0.635 mmol) in THF (5 mL) and water (0.5 mL) to lithium hydroxide hydrate (0.0808 g, 1.91 mmol), the mixture is stirred at 50° C. for 18 hours. Then the mixture's pH is adjusted to 5-6 with 1.0M HCl solution and the mixture is extracted with EtOAc (30 mL×3). The combined organic layers are washed with brine (30 mL), dried over anhydrous sodium sulfate and concentrated. The crude product is purified by prep-HPLC (column: Phenomenex Gemini 150×25 mm×10 m, Gradient: 50-80% B (A=water/0.05% HCl, B=acetonitrile), Flow rate: 25 mL/min). The desired fractions are lyophilized to afford the title compound (112.6 mg, 38.3%) as a yellow solid. LCMS (m/z): 454.2 [M+H]⁺.

¹H NMR (400 MHz, DMSO-d6) δ=9.19 (s, 1H), 7.91-7.83 (m, 3H), 7.61-7.51 (m, 6H), 7.36 (d, J=8.4 Hz, 2H), 3.65 (s, 3H), 2.84-2.74 (m, 1H), 1.48-1.43 (m, 2H), 1.17-1.13 (m, 2H), 1.07 (d, J=6.8 Hz, 6H).

EXAMPLE 27

1-[4-[6-[5-[(6-isopropylpyrazin-2-yl)amino]-1-methyl-pyrazol-4-yl]-3-pyridyl]phenyl]cyclopropanecarboxylic acid 1. Synthesis of 1-[4-[6-[5-[(6-chloropyrazin-2-yl)amino]-1-methyl-pyrazol-4-yl]-3-pyridyl]phenyl]cyclopropanecarboxylic acid

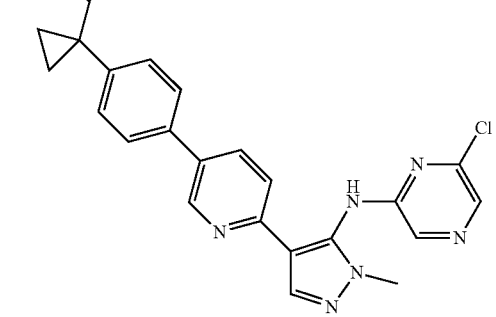

Add sodium hydride (0.293 g, 7.32 mmol, 60% in paraffin oil) to the solution of 1-[4-[6-(5-amino-1-methyl-pyrazol-4-yl)-3-pyridyl]phenyl]cyclopropanecarboxylic acid (0.600 g, 1.46 mmol, 85 mass %) (prepared according to Example 1A) in DMF (2 mL) at 20° C. The reaction is stirred at 50° C. for 20 minutes and then 2,6-dichloropyrazine (0.264 g, 1.76 mmol) is added. The reaction is stirred at 50° C. for 3 hours. The mixture is added into water (20 mL). The mixture is extracted with EtOAc (20 mL×3). Then the aqueous phase is acidified by 1 M HCl to pH=4-5. The mixture is extracted with EtOAc (20 mL×3). The combined organic layers are washed with brine (30 mL), dried over anhydrous sodium sulfate and concentrated, to afford title compound (495 mg, 75%) as a yellow solid. LCMS (m/z): 447.0 [M+H]⁺.

2. Synthesis of 1-[4-[6-[5-[(6-isopropenylpyrazin-2-yl)amino]-1-methyl-pyrazol-4-yl]-3-pyridyl]phenyl]cyclopropanecarboxylic acid

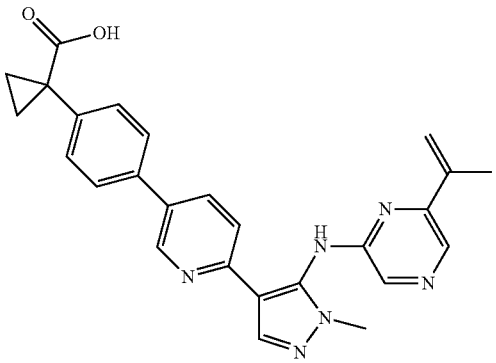 [SMILES: C=C(C)c1cncc(Nc2c(-c3ccc(-c4ccc(C5(C(=O)O)CC5)cc4)cn3)cnn2C)n1]

Add Pd(dppf)Cl$_2$ (0.081 g, 0.111 mmol) to the suspensions of 2-isopropenyl-4,4,5,5-tetramethyl-1,3,2-dioxaborolane (0.282 g, 1.66 mmol), 1-[4-[6-[5-[(6-chloropyrazin-2-yl)amino]-1-methyl-pyrazol-4-yl]-3-pyridyl]phenyl]cyclopropanecarboxylic acid (495 mg, 1.11 mmol) and sodium carbonate (352 mg, 3.32 mmol) in water (0.5 mL) and 1,4-dioxane (5 mL) under nitrogen. The reaction is heated to 90° C. for 3 hours. The mixture is diluted with water (20 mL) and adjusted pH=5-6 with 1 M HCl, extracted with EtOAc (30 mL×3). The combined organic layers are washed with brine (30 mL), dried over anhydrous sodium sulfate and concentrated. The residue is purified by flash chromatography on silica gel eluting with petroleum ether:EtOAc (2:1) to afford compound (293 mg, 58%) as a yellow solid. LCMS (m/z): 453.0 [M+H]$^+$.

3. Synthesis of 1-[4-[6-[5-[(6-isopropylpyrazin-2-yl)amino]-1-methyl-pyrazol-4-yl]-3-pyridyl]phenyl]cyclopropanecarboxylic acid

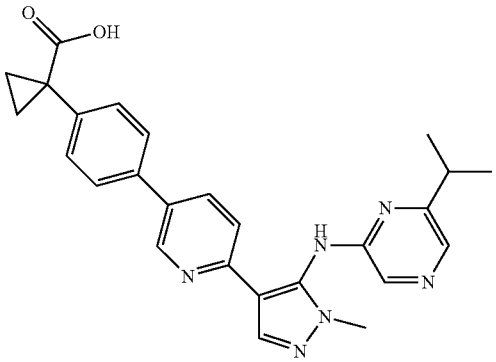 [SMILES: CC(C)c1cncc(Nc2c(-c3ccc(-c4ccc(C5(C(=O)O)CC5)cc4)cn3)cnn2C)n1]

Add 1-[4-[6-[5-[(6-isopropenylpyrazin-2-yl)amino]-1-methyl-pyrazol-4-yl]-3-pyridyl]phenyl]cyclopropanecarboxylic acid (400 mg, 0.575 mmol, 65 mass %) in methanol (10 mL) to palladium on activated carbon (120 mg, 10 mass %) at room temp. the mixture is stirred under molecular hydrogen (15 psi) at 10° C. for 18 hours. The solid is filtered off and the filtrate is evaporated to afford the crude. The crude product is purified by prep-HPLC [Column:YMC-Actus Triart C18 150*30, 5 µm; Condition: 36-66% B (A=0.05% HCl, B=acetonitrile); flow rate: 25 mL/min] to afford title compound (31.1 mg, 11%) as a white solid. LCMS (m/z): 455 0.0 [M+H]$^+$.

$^1$H NMR (400 MHz, DMSO-d6) δ=9.98 (s, 1H), 8.87 (d, J=2.0 Hz, 1H), 8.50 (d, J=8.0 Hz, 1H), 8.32 (s, 1H), 8.21 (s, 1H), 7.91 (s, 1H), 7.89-7.83 (m, 1H), 7.71 (d, J=8.4 Hz, 2H), 7.48 (d, J=8.4 Hz, 2H), 3.78 (s, 3H), 2.75-2.66 (m, 1H), 1.53-1.46 (m, 2H), 1.21-1.16 (m, 2H), 0.97-0.86 (m, 6H).

LPAR1 Calcium Flux Assays

A cDNA encoding the human LPAR1 receptor is synthesized and cloned into pDNA3 expression plasmid. The plasmid is transfected in U937 cells using Lipofectamine 2000 (Invitrogen Corp., USA). Clones stably expressing human LPAR1 are selected using puromycin and identified as cells that show Ca-influx in response to LPA.

U937 cells overexpressing human LPAR1 are seeded at 100,000 cells per well in a 96-well fibronectin (10 ug/ml) coated plate in 60 µl of assay buffer (HBSS containing 20 mM HEPES and 0.2% BSA) and then incubated for 60 minutes. Then 50 µl of a calcium indicator dye (Fluo-4 NW, Molecular Probes) are added to each well and incubation continued for 30 minutes at 37° C. and then 30 minutes at room temperature. 50 µl of test compounds in 4% DMSO are added to the cells and incubation continued at room temperature for 40 minutes. Cells are the stimulated by the addition of 50 µl of 128 nM LPA and intracellular calcium is measured using the FLIPR TETRA (Molecular Devices). IC50 values are determined using "Genedata Screener" analysis tool.

LPAR3 Calcium Flux Assays

A cDNA encoding the human LPAR3 receptor is synthesized and cloned into pDNA3 expression plasmid. The plasmid is transfected in U2OS cells using Lipofectamine 2000 (Invitrogen Corp., USA). Clones stably expressing human LPAR3 are selected using neomycin and identified as cells that show Ca-influx in response to LPA.

U2OS cells overexpressing human LPAR3 are seeded at 20,000-40,000 cells per well in a 96-well poly-D-lysine coated plate one day before the assay. Prior to the assay, the cells are washed once with assay buffer (HBSS containing 20 mM HEPES and 0.2% BSA) and then incubated in 50 µl of assay buffer for 60 minutes. Then 50 µl of a calcium indicator dye (Fluo-4 NW, Molecular Probes) are added to each well and incubation is continued for 30 minutes at 37° C. and then 30 minutes at room temperature. 50 µl of test compounds in 4% DMSO are added to the cells and incubation continued at room temperature for 40 minutes. Cells are stimulated by the addition of 50 µl of 128 nM LPA and intracellular calcium is measured using the FLIPR TETRA (Molecular Devices). IC50 values are determined using "Genedata Screener" analysis tool.

LPAR1 Membrane Binding Assay

The ability of a compound to inhibit binding of a ligand (1-(4'-(4-(((benzyloxy)carbonyl)amino)-3-methylisoxazol-5-yl)-[1,1'-biphenyl]-4-yl)cyclopropane-1-carboxylic acid) to LPAR1 is assessed via a membrane binding assay. Membrane containing LPAR1 was purchased from Cerep (Cat. No. 290312RB). Prior to the assay, membrane is thawed and homogenized for 15 seconds. 50 µl of test compounds and 50 µl of radio labeled ligand are added to the 96-well plates and then 50 of membrane (50-400 ug/ml) are added. Next, 50 µl of SPA PVT WGA beads are added (1-5 mg/ml) and the plates are sealed and incubated at room temperate for 5 minutes. Radio activity is measured by Beta Counter and IC50 values are determined using "Genedata Screener" analysis tool.

Calcium Influx of Human Hepatic Stellate Cells (LX-2)

Human hepatic stellate cell line LX-2 is purchased from EMD Millpore. LX-2 cells are seeded at 20,000-40,000 cells per well in a 96-well poly-D-lysine coated plate one day before the assay. Prior to the assay, the cells are washed once with assay buffer (HBSS containing 20 mM HEPES and 0.2% BSA) and then incubated in 50 µl of assay buffer for 60 minutes. Then 50 µl of a calcium indicator dye (Fluo-4 NW, Molecular Probes) are added to each well and incubation is continued for 30 minutes at 37° C. and then 30 minutes at room temperature. 50 µl of test compounds in 4% DMSO are added to the cells and incubation is continued at room temperature for 40 minutes. Cells are stimulated by the addition of 50 µl of 128 nM LPA and intracellular calcium is measured using the FLIPR TETRA (Molecular Devices). IC50 values are determined using "Genedata Screener" analysis tool.

LPAR1 Cytokine Release Assay

Human MG63 cells are seeded at 20,000 per well in 96-well plates and incubated in MEM medium. One day later, the cell culture medium is removed and 60 µl of test compounds are added to each well. 30 minutes later, 60 µl of LPA (10 µM) are added to each well. 24 hours later, 50 µl of supernatant from each well are taken and IL-6 levels are measure by using ELISA kit (R&D Systems, Cat. No. D6050). IC50 values are determined using "Genedata Screener" analysis tool.

Representative active compounds of the present invention ("B" Examples, as opposed to ester prodrugs, "A" Examples) were assayed essentially as described above and the results were summarized in Table 1 below:

TABLE 1

| Example No. | LPAR1 IC50 (nM) | LPAR3 IC50 (nM) | LPAR1 Binding ki (nM) | LX-2 (nM) | LPAR1 Cytokine Release Assay IC50 (nM) |
|---|---|---|---|---|---|
| 1 | 74.4 | 1330 | nt* | 37.2 | nt |
| 2 | 17.2 | 327 | nt | 9.22 | nt |
| 3 | 8.61 | 2480 | 44.2 | 3.8 | nt |
| 4 | 16.7 | 1590 | 80.5 | 8.67 | nt |
| 5 | 26.9 | 49.6 | 51.4 | 17.1 | nt |
| 6 | 122 | 5270 | 115 | 60.5 | nt |
| 7 | 27.1 | 1050 | 72.3 | 16.3 | nt |
| 8 | 22 | >10000 | nt | 7.13 | nt |
| 9 | 17.9 | >10000 | nt | 10.5 | nt |
| 10 | 9.86 | 4420 | 12.5 | 5.41 | nt |
| 11 | 11.1 | 495 | 34.6 | 10 | nt |
| 12 | 24.4 | 4280 | 40.9 | 14.4 | nt |
| 13 | 44 | 804 | 28 | 10.5 | nt |
| 14 | 45.8 | >10000 | nt | 13.2 | nt |
| 15 | 42.9 | >10000 | 94.8 | 19.4 | nt |
| 16 | 29.3 | 4620 | 53.8 | 18.2 | nt |
| 17 | 54.7 | 1830 | nt | 23.1 | 5.81 |
| 18 | 24 | 2360 | 24.5 | 7.94 | 6.67 |
| 19 | 88.1 | 2400 | nt | 16.3 | nt |
| 20 | 29.3 | 341 | 12.7 | 12 | 3.95 |
| 21 | 36.3 | 1610 | 27.6 | 14.1 | 8.81 |
| 22 | 30.9 | 1170 | nt | 10.4 | 11.2 |
| 23 | 111 | >10000 | nt | 21.5 | 183 |
| 24 | 48 | 2760 | 46.2 | 15.3 | nt |
| 25 | 52.9 | >10000 | 30.8 | 24.2 | nt |
| 26 | 23.6 | >10000 | 18.8 | 13.1 | 4.79 |
| 27 | 20.6 | 1980 | 15.3 | 8.88 | nt |

*nt: not tested.

Rodent Pharmacokinetics

The pharmacokinetics of compounds are determined in male Sprague-Dawley rats or C57 mice. The rats are administered a single 1 mg/kg intravenous (IV) and 10 mg/kg oral gavage (PO) dose. The vehicles are 20% Captisol w/v in 25 mM NaPO4 buffer, pH8 and 1% hydroxyethylcellulose/ 0.25% polysorbate 80 and 0.05% antifoam 1510-US in distilled water for the intravenous and oral dose, respectively. Blood samples are collected at predose (PO only), 0.08 (IV only), 0.25, 0.5, 1, 2, 4, 8, 12 and 24 h after initiation of compound administration. Blood samples are centrifuged to obtain plasma. The plasma samples are analyzed by LC-MS/MS to determine compound concentrations.

Representative active compounds (as opposed to ester prodrugs) of the present invention assayed essentially as described above and the results were summarized in Table 2A and 2B below:

TABLE 2A

| | Mouse PK | | | |
|---|---|---|---|---|
| Example No. | AUC (hr * nM, 10 mg/kg, PO) | CL (mL/min/kg) | Vdss (L/kg) | % F |
| 21 | 16333 | 4.99 | 1.46 | 24.8 |
| 26 | 9065 | 2.00 | 2.00 | 30.0 |
| 27 | 38385 | 3.50 | 0.953 | 40.8 |

TABLE 2B

| | Rat PK | | | |
|---|---|---|---|---|
| Example No. | AUC (hr * nM, 10 mg/kg, PO) | CL (mL/min/kg) | Vdss (L/kg) | % F |
| 20 | 70872 | 2.94 | 0.721 | 57.5 |
| 27 | 80123 | 4.23 | 0.799 | 93.6 |

Diet-Induced Liver Inflammation and Fibrosis

Male C57Bl/6 mice (7-8 weeks old) are given free access to food and water. Mice are fed with high fat, high sucrose and high cholesterol food for 196 days. Then animals will be administrated orally with vehicle or test compounds once daily for 77 days at a volume of 5 ml/kg. Body weight and food intake will be measured twice a week, after two weeks, BW and FI will be measured once a week. At the end of study, animals will be euthanized by CO2 suffocation. Liver samples of the animals are collected and fixed in 10% NBF. Liver samples are prepared after 20 to 24 hours of fixation in 10% NBF and prepared into FFPE blocks. Slide sections of FFPE blocks are processed with H&E and Masson's Trichrome staining. Histopathology interpretation and results will be provided by qualified pathologists. The data are plotted using Graphpad prism and statistical differences between groups determined.

Active compound Example no. 27 (as opposed to ester prodrug) was assayed P essentially as described above and the results were summarized in Table 3 below:

TABLE 3

|  | vehicle | Example No. 27 (10 mg/kg) | Example No. 27 (30 mg/kg) |
|---|---|---|---|
| Inflammation Score | 2.7 | 2.1* | 2.3# |
| Peri-sinusoidal Fibrosis Score | 1.37 | 1.30 | 1.07 $ |

*P < 0.001
P < 0.003
$ P < 0.014

Mouse Intravenous LPA-induced Histamine and Eicosanoids Release

A mouse intravenous LPA-induced histamine and eicosanoids release model is utilized to determine the in vivo potency of the compounds of the present invention. Male C57BL/6J mice weighing 20-25 grams are given free access to standard mouse chow and water. LPA is dissolved in 0.1% fatty acid-free bovine serum albumin to generate solution at 2 mg/mL. Test compounds are formulated in 0.5% methyl cellulose plus 0.25% Tween 80 to generate required concentrations one day before the experiment and stored in a refrigerator until use. Animals are dosed orally with test compounds at 10 ml/kg 2 hours before the intravenous LPA dosing (300 ug per mouse) with 30 gauge needles through tail vain. Two hours after LPA dosing the animals are euthanized by $CO_2$ suffocate. Blood will be collected by cardiac puncture. Blood samples are kept on ice for more than 5 minutes and centrifuged at 4000 rpm for 10 minutes at 4° C. to generate supernatant plasma. The plasma histamine, methylimidazol acetic acid and eicosanoids levels are measured by LC/MS.

Active compound Example Nos. 20 and 27 (as opposed to ester prodrug) were assayed essentially as described above and the results were summarized in Table 4 below:

TABLE 4

| Released factors | Example No. 20 (10 mg/kg) % of inhibition | Example No. 27 (10 mg/kg) % of inhibition |
|---|---|---|
| histamine | NA* | 89.5 ± 1.6 |
| methylimidazoleacetic acid | 103.5 ± 0.6 | 100.8 ± 3.4 |
| 12-hydroxy-eicosatetraenoic acid | 68.8 ± 6.0 | NA |
| 9,10-cis epoxide of linoleic acid | 83.4 ± 6.4 | NA |

*not available.

We claim:

1. A method for treating nonalcoholic steatohepatitis (NASH) comprising administering to a mammal in need thereof, an effective amount of a compound of the formula

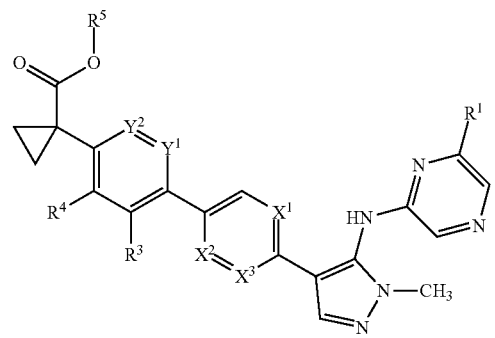

wherein,
X$^1$ and X$^2$ are each independently CH or N, and X$^3$ is C-R$^2$ or N, provided that when X$^1$ is CH, then X$^2$ is CH and X$^3$ is C-R$^2$, and provided that when X$^1$ is N, then only one of X$^2$ or X$^3$ may be N;
Y$^1$ and Y$^2$ are CH or N, provided that only one of Y$^1$ or Y$^2$ may be N;
R$^1$ is
  isopropyl,
  isobutyl,
  t-butyl,
  2-hydroxypropyl-2-yl,
  cyclopropyl,
  cyclopropyloxy,
  t-butyloxy,
  cyclobutyloxy,
  3,3-difluorocyclobutyloxy,
  2-fluoropropyl-2-yl,
  1,1-difluoroethyl,
  trifluoromethyl,
  isopropyloxy, or
  2-methoxypropyl-2-yl;
R$^2$ is H or fluoro;
R$^3$ is H, halogen, C$_1$-C$_3$ alkyl, C$_1$-C$_3$ alkoxy, C$_1$-C$_3$ alkoxymethyl, CF$_3$, or cyano;
R$^4$ is H, halogen, C$_1$-C$_3$ alkyl, or CF$_3$;
R$^5$ is H, methyl, ethyl, propyl, isopropyl, or cyclopropyl; or
a pharmaceutically acceptable salt thereof.

2. The method according to claim 1, wherein X$^1$ is N, or a pharmaceutically acceptable salt thereof.

3. The method according to claim 1, wherein X$^1$ is CH, or a pharmaceutically acceptable salt thereof.

4. The method according to claim 1, wherein Y$^1$ is CH, or a pharmaceutically acceptable salt thereof.

5. The method according to claim 1, wherein R$^1$ is isopropyl, or a pharmaceutically acceptable salt thereof.

6. The method according to claim 1, wherein R$^1$ is cyclopropyloxy, or a pharmaceutically acceptable salt thereof.

7. The method according to claim 1, wherein the compound is selected from:
  1-[4-[6-[5-[(6-tert-butoxypyrazin-2-yl)amino]-1-methyl-pyrazol-4-yl]-3-pyridyl]phenyl]cyclopropanecarboxylic acid,
  1-[4-[6-[5-[[6-(cyclobutoxy)pyrazin-2-yl]amino]-1-methyl-pyrazol-4-yl]-3-pyridyl]phenyl]cyclopropanecarboxylic acid,
  1-[4-[6-[5-[[6-(cyclopropoxy)pyrazin-2-yl]amino]-1-methyl-pyrazol-4-yl]-5-fluoro-3-pyridyl]phenyl]cyclopropanecarboxylic acid; hydrochloride, 1-[4-[5-fluoro-6-[5-[6-(1-fluoro-1-methyl-ethyl)pyrazin-2-yl]amino]-1-methyl-pyrazol-4-yl]-3-pyridyl]phenyl] cyclopropanecarboxylic acid; hydrochloride, 1-[4-[6-[5-[6-(3,3-difluorocyclobutoxy)pyrazin-2-yl] amino]-1-methyl-pyrazol-4-yl]-3-pyridyl]phenyl]cyclopropanecarboxylic acid, 1-[4-[6-[5-[[6-(1-methoxy-1-methyl-ethyl)pyrazin-2-yl] amino]-1-methyl-pyrazol-4-yl]-3-pyridyl]phenyl]cyclopropanecarboxylic acid; hydrochloride, 1-[4-[6-[5-[(6-isopropoxypyrazin-2-yl)amino]-1-methyl-pyrazol-4-yl]-3-pyridyl]-2-methyl-phenyl]cyclopropanecarboxylic acid; hydrochloride, 1-[4-[6-[5-[6-(cyclopropoxy)pyrazin-2-yl]amino]-1-methyl-pyrazol-4-yl]-3-pyridyl]-2-(trifluoromethyl) phenyl]cyclopropanecarboxylic acid; hydrochloride, 1-[4-[6-[5-[6-(cyclopropoxy)pyrazin-2-yl]amino]-1-methyl-pyrazol-4-yl]-3-pyridyl]phenyl]cyclopropanecarboxylic acid, 1-[4-[5-fluoro-6-[5-[(6-isopropoxypyrazin-2-yl)amino]-1-methyl-pyrazol-4-yl]-3-pyridyl]phenyl]cyclopropanecarboxylic acid; hydrochloride, 1-[4-[6-[5-[[6-(1,1-difluoroethyl)pyrazin-2-yl]amino]-1-methyl-pyrazol-4-yl]-3-pyridyl]phenyl]cyclopropanecarboxylic acid; hydrochloride, 1-[4-[6-[5-[[6-(1-fluoro-1-methyl-ethyl)pyrazin-2-yl] amino]-1-methyl-pyrazol-4-yl]-3-pyridyl]phenyl]cyclopropanecarboxylic acid; hydrochloride, 1-[4-[6-[5-[(6-isopropylpyrazin-2-yl)amino]-1-methyl-pyrazol-4-yl]-3-pyridyl]-3-(methoxymethyl)phenyl] cyclopropanecarboxylic acid; hydrochloride, 1-[3-cyano-4-[6-[5-[(6-isopropylpyrazin-2-yl)amino]-1-methyl-pyrazol-4-yl]-3-pyridyl]phenyl]cyclopropanecarboxylic acid; hydrochloride, 1-[4-[4-[5-[(6-isobutylpyrazin-2-yl)amino]-1-methyl-pyrazol-4-yl]phenyl]phenyl]cyclopropanecarboxylic acid, 1-[4-[2-[5-[(6-isopropylpyrazin-2-yl)amino]-1-methyl-pyrazol-4-yl]pyrimidin-5-yl]phenyl]cyclopropanecarboxylic acid, 1-[4-[5-[5-[(6-isopropylpyrazin-2-yl)amino]-1-methyl-pyrazol-4-yl]pyrazin-2-yl]phenyl]cyclopropanecarboxylic acid; hydrochloride, 1-[4-[6-[5-[(6-isopropoxypyrazin-2-yl)amino]-1-methyl-pyrazol-4-yl]-3-pyridyl]phenyl]cyclopropanecarboxylic acid; hydrochloride, 1-[4-[6-[1-methyl-5-[[6-(trifluoromethyl)pyrazin-2-yl] amino]pyrazol-4-yl]-3-pyridyl]phenyl]cyclopropanecarboxylic acid, 1-[4-[6-[5-[(6-isopropylpyrazin-2-yl)amino]-1-methyl-pyrazol-4-yl]-3-pyridyl]-3-methyl-phenyl]cyclopropanecarboxylic acid; hydrochloride, 1-[5-[6-[5-[(6-isopropylpyrazin-2-yl)amino]-1-methyl-pyrazol-4-yl]-3-pyridyl]-2-pyridyl]cyclopropanecarboxylic acid, 1-[6-[6-[5-[(6-isopropylpyrazin-2-yl)amino]-1-methyl-pyrazol-4-yl]-3-pyridyl]-3-pyridyl]cyclopropanecarboxylic acid; dihydrochloride, Ammonium 1-[4-[4-[5-[(6-cyclopropylpyrazin-2-yl) amino]-1-methyl-pyrazol-4-yl]phenyl]phenyl]cyclopropanecarboxylate, 1-[4-[4-[5-[(6-isopropylpyrazin-2-yl)amino]-1-methyl-pyrazol-4-yl]phenyl]phenyl]cyclopropanecarboxylic acid, or 1-[4-[6-[5-[(6-isopropylpyrazin-2-yl)amino]-1-methyl-pyrazol-4-yl]-3-pyridyl]phenyl]cyclopropanecarboxylic acid;

or a pharmaceutically acceptable salt thereof.

8. The method of claim 1, wherein the compound is 1-[4-[6-[5-[(6-isopropylpyrazin-2-yl)amino]-1-methyl-pyrazol-4-yl]-3-pyridyl]phenyl]cyclopropanecarboxylic acid, or a pharmaceutically acceptable salt thereof.

9. The method of claim 1, wherein the compound is 1-[4-[4-[5-[(6-isopropylpyrazin-2-yl)amino]-1-methyl-pyrazol-4-yl]phenyl]phenyl]cyclopropanecarboxylic acid, or a pharmaceutically acceptable salt thereof.

10. The method according to claim 1, wherein the mammal is a human.

* * * * *

UNITED STATES PATENT AND TRADEMARK OFFICE
CERTIFICATE OF CORRECTION

PATENT NO. : 12,145,924 B2
APPLICATION NO. : 17/747261
DATED : November 19, 2024
INVENTOR(S) : Tianwei Ma, Liang Wu and Xuejun Zhang It is certified that error appears in the above-identified patent and that said Letters Patent is hereby corrected as shown below:

In the Claims

Column 80; Line 35; In Claim 1, delete "1, 1-" and insert -- 1,1- --.

Column 81; Line 1; In Claim 7, delete "[6-" and insert -- [[6- --.

Column 81; Line 4; In Claim 7, delete "[6-" and insert -- [[6- --.

Column 81; Line 13; In Claim 7, delete "[6-" and insert -- [[6- --.

Column 81; Line 16; In Claim 7, delete "[6-" and insert -- [[6- --.

Column 81; Line 22; In Claim 7, delete "(1, 1-" and insert -- (1,1- --.

Signed and Sealed this
Fourth Day of March, 2025

Coke Morgan Stewart
*Acting Director of the United States Patent and Trademark Office*